(12) United States Patent
Edwards et al.

(10) Patent No.: US 6,818,391 B2
(45) Date of Patent: Nov. 16, 2004

(54) GLUTAMATE TRANSPORTERS

(75) Inventors: Robert H. Edwards, San Francisco, CA (US); Elizabeth E. Bellocchio, Walnut Creek, CA (US); Robert T. Fremeau, Jr., San Francisco, CA (US); Richard J. Reimer, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/915,181

(22) Filed: Jul. 24, 2001

(65) Prior Publication Data

US 2002/0098473 A1 Jul. 25, 2002

Related U.S. Application Data

(60) Provisional application No. 60/220,556, filed on Jul. 25, 2000.

(51) Int. Cl.[7] .............................. C12Q 1/00; C12Q 1/68; G01N 33/53; C12N 5/00
(52) U.S. Cl. ............................... 435/4; 435/6; 435/7.1; 435/7.2; 435/7.21; 435/325
(58) Field of Search .......................... 435/4, 6, 7.1, 7.2, 435/7.21, 325, 375, 320.1

(56) References Cited

U.S. PATENT DOCUMENTS 5,739,284 A    4/1998  Hediger et al.

FOREIGN PATENT DOCUMENTS

JP    10099083    *  4/1998
WO   WO 98/11222    3/1998

OTHER PUBLICATIONS

The identification of vesicular glutamate transporter 3 suggests novel modes of signaling by glutamate. Fremeau RT Jr et al. Proc Natl Acad Sci U S A. 99(22):14488–93, 2002.*

Molecular cloning and functional characterization of human vesicular glutamate transporter 3. Takamori et al. EMBO Rep. 3(8):798–803, 2002.*

McIntire et al. Nature 389:870–876, 1997.*

Conradt et al. J Neurochem. 1997, 68:1244–51 abstract only.*

Bellocchio et al. The Journal of Neuroscience 18:8648–8659, 1998.*

* cited by examiner

*Primary Examiner*—Ram R. Shukla
(74) *Attorney, Agent, or Firm*—Quine Intellectual Property Law Group, P.C.

(57) ABSTRACT

This invention pertains to the identification of a novel class of glutamate transporters. In particular, this invention pertains to the discovery that proteins originally considered to perform an entirely different function (BNPI, DNPI, etc.), in fact, transport glutamate into synaptic vesicles. Designated VGLUT glutamate transporters, the transporters provide good targets with which to screen for modulators of glutamate uptake into synaptic vesicles.

21 Claims, 24 Drawing Sheets

```
                BsiHKAI
                   |
        TGTGCTCTAAAGCCCCCATTCAAAATGCCATTTAACGCATTTGATACCTTCAAAGAAAAA
     1  ---------+---------+---------+---------+---------+---------+  60
        ACACGAGATTTCGGGGGTAAGTTTTACGGTAAATTGCGTAAACTATGGAAGTTTCTTTTT a         C  A  L  K  P  P  F  K  M  P  F  N  A  F  D  T  F  K  E  K  -

SmaI
               XmaI |                      BsmI
                 | |                        |
        ATTTTGAAACCCGGGAAGGAAGGAGTGAAGAATGCCGTAGGAGATTCGCTGGGGATCTTA
    61  ---------+---------+---------+---------+---------+---------+ 120
        TAAAACTTTGGGCCCTTCCTTCCTCACTTCTTACGGCATCCTCTAAGCGACCCCTAGAAT a         I  L  K  P  G  K  E  G  V  K  N  A  V  G  D  S  L  G  I  L  -

TaqI
                   |
        CAAAGAAAACTCGATGGGACCAACGAGGAGGGAGATGCCATTGAGCTGAGTGAGGAAGGA
   121  ---------+---------+---------+---------+---------+---------+ 180
        GTTTCTTTTGAGCTACCCTGGTTGCTCCTCCCTCTACGGTAACTCGACTCACTCCTTCCT a         Q  R  K  L  D  G  T  N  E  E  G  D  A  I  E  L  S  E  E  G  -

AlwNI
                                                      PvuII |
          StuI                      BsgI              PstI| |
            |                        |                 | | |
        AGGCCTGTGCAGACATCCAGAGCCCGAGCCCCTGTGTGCGACTGCAGCTGCTGTGGCATC
   181  ---------+---------+---------+---------+---------+---------+ 240
        TCCGGACACGTCTGTAGGTCTCGGGCTCGGGGACACACGCTGACGTCGACGACACCGTAG a         R  P  V  Q  T  S  R  A  R  A  P  V  C  D  C  S  C  C  G  I  -

BspHI
                             |
        CCCAAGCGGTACATCATCGCTGTCATGAGTGGCCTGGGATTCTGCATTTCCTTTGGGATT
   241  ---------+---------+---------+---------+---------+---------+ 300
        GGGTTCGCCATGTAGTAGCGACAGTACTCACCGGACCCTAAGACGTAAAGGAAACCCTAA a         P  K  R  Y  I  I  A  V  M  S  G  L  G  F  C  I  S  F  G  I  -

MscI   XcmI
                        |     |
        CGGTGCAACCTTGGAGTGGCCATTGTGGAAATGGTCAACAATAGCACTGTGTATGTGGAT
   301  ---------+---------+---------+---------+---------+---------+ 360
        GCCACGTTGGAACCTCACCGGTAACACCTTTACCAGTTGTTATCGTGACACATACACCTA a         R  C  N  L  G  V  A  I  V  E  M  V  N  N  S  T  V  Y  V  D  -
```

*Fig. 1*

```
                                      BsmBI
              BsaWI          BamHI|  BmrI          EcoRI
                |               | |    |              |
              GGGAAACCGGAAATCCAGACAGCACAGTTTAACTGGGATCCAGAGACGGTGGGAAGGGCG
       361    ---------+---------+---------+---------+---------+---------+    420
              CCCTTTGGCCTTTAGGTCTGTCGTGTCAAATTGACCCTAGGTCTCTGCCACCCTTCCCGC a             G  K  P  E  I  Q  T  A  Q  F  N  W  D  P  E  T  V  G  R  A    -

MaeIII
                   NcoI                         Tsp45I
                    |                              |
              AATTCTCTTATCCATGGATCTTTTTTCTGGGGTTATATTGTGACACAAATTCCCGGTGGC
       421    ---------+---------+---------+---------+---------+---------+    480
              TTAAGAGAATAGGTACCTAGAAAAAAGACCCCAATATAACACTGTGTTTAAGGGCCACCG a             N  S  L  I  H  G  S  F  F  W  G  Y  I  V  T  Q  I  P  G  G    -

AatII
                                                       BsaHI  |
                                                          |   |
              TTCATTTCAAACAAGTTTGCTGCTAACAGGGTCTTTGGAGCTGCCATCTTCTTGACGTCA
       481    ---------+---------+---------+---------+---------+---------+    540
              AAGTAAAGTTTGTTCAAACGACGATTGTCCCAGAAACCTCGACGGTAGAAGAACTGCAGT a             F  I  S  N  K  F  A  A  N  R  V  F  G  A  A  I  F  L  T  S    -

XmnI            SacII
                   PciI  |         BstUI|
                    |  |             | |
              ACCCTGAACATGTTCATCCCTTCCGCGGCCAGGGTGCATTACGGCTGTGTCATGTGTGTG
       541    ---------+---------+---------+---------+---------+---------+    600
              TGGGACTTGTACAAGTAGGGAAGGCGCCGGTCCCACGTAATGCCGACACAGTACACACAC a             T  L  N  M  F  I  P  S  A  A  R  V  H  Y  G  C  V  M  C  V    -

MaeIII
                         AlwNI    Tsp45I
                           |         |
              AGGATTTTGCAGGGTCTGGTGGAGGGTGTGACCTACCCAGCCTGCCACGGGATGTGGAGT
       601    ---------+---------+---------+---------+---------+---------+    660
              TCCTAAAACGTCCCAGACCACCTCCCACACTGGATGGGTCGGACGGTGCCCTACACCTCA a             R  I  L  Q  G  L  V  E  G  V  T  Y  P  A  C  H  G  M  W  S    -
                                                     BpmI
                                                       |
              AAGTGGGCACCTCCCCTGGAGAGAAGTCGTCTAGCCACAACCTCTTTTTGTGGTTCCTAT
       661    ---------+---------+---------+---------+---------+---------+    720
              TTCACCCGTGGAGGGGACCTCTCTTCAGCAGATCGGTGTTGGAGAAAAACACCAAGGATA a             K  W  A  P  P  L  E  R  S  R  L  A  T  T  S  F  C  G  S  Y    -
```

*Fig. 1 cont'd*

```
                BstAPI                              TatI
                  |                                   |
            GCCGGGGCAGTCGTTGCTATGCCCCTTGCAGGAGTATTGGTGCAGTACATTGGCTGGGCC
      721   ---------+---------+---------+---------+---------+---------+  780
            CGGCCCCGTCAGCAACGATACGGGGAACGTCCTCATAACCACGTCATGTAACCGACCCGG a           A  G  A  V  V  A  M  P  L  A  G  V  L  V  Q  Y  I  G  W  A   -

BsgI                                        PciI
           |                                            |
            TCTGCCTTTTATATTTACGGGATGTTTGGAATTATTTGGTACATGTTTTGGCTGCTGCTG
      781   ---------+---------+---------+---------+---------+---------+  840
            AGACGGAAAATATAAATGCCCTACAAACCTTAATAAACCATGTACAAAACCGACGACGAC a           S  A  F  Y  I  Y  G  M  F  G  I  I  W  Y  M  F  W  L  L  L   -

PstI       HphI
            |          |
            CAGGCTTATGAGTGTCCAGCAGTTCACCCAACAATATCCAATGAAGAACGGACCTACATA
      841   ---------+---------+---------+---------+---------+---------+  900
            GTCCGAATACTCACAGGTCGTCAAGTGGGTTGTTATAGGTTACTTCTTGCCTGGATGTAT a           Q  A  Y  E  C  P  A  V  H  P  T  I  S  N  E  E  R  T  Y  I   -

BbeI
                                       HaeII
                                       HhaI|
                                      SfoI||
                                    BsaHI|||
                                   HinP1I|||
                                     NarI|||      MscI
                                    KasI||||  BglI  |                NcoI
                                       ||||    |    |                   |
            GAGACAAGTATAGGAGAAGGCGCCAACTTGGCCAGTCTGAGCAAATTCAACACACCATGG
      901   ---------+---------+---------+---------+---------+---------+  960
            CTCTGTTCATATCCTCTTCCGCGGTTGAACCGGTCAGACTCGTTTAAGTTGTGTGGTACC a           E  T  S  I  G  E  G  A  N  L  A  S  L  S  K  F  N  T  P  W   -

BstXI
                                                     |
            AGAAGGTTTTTCACATCCTTGCCTGTCTATGCCATTATTGTGGCAAACTTTTGTAGAAGC
      961   ---------+---------+---------+---------+---------+---------+  1020
            TCTTCCAAAAAGTGTAGGAACGGACAGATACGGTAATAACACCGTTTGAAAACATCTTCG a           R  R  F  F  T  S  L  P  V  Y  A  I  I  V  A  N  F  C  R  S   -
```

*Fig. 1 cont'd*

```
            TGGACCTTCTATTTGCTCTTAATAAGTCAGCCTGCTTACTTTGAAGAGGTCTTTGGGTTT
    1021    ---------+---------+---------+---------+---------+---------+ 1080
            ACCTGGAAGATAAACGAGAATTATTCAGTCGGACGAATGAAACTTCTCCAGAAACCCAAA a         W  T  F  Y  L  L  I  S  Q  P  A  Y  F  E  E  V  F  G  F   -

BsaI PvuII          DraIII BsaBI HphI Acc65I
                         |    |              |      |    |     |
            GCAATAAGTAAGGTGGGTCTCTTGTCAGCTGTCCCACACATGGTGATGACAATCGTGGTA
    1081    ---------+---------+---------+---------+---------+---------+ 1140
            CGTTATTCATTCCACCCAGAGAACAGTCGACAGGGTGTGTACCACTACTGTTAGCACCAT a         A  I  S  K  V  G  L  L  S  A  V  P  H  M  V  M  T  I  V  V  -

KpnI
           |
            CCCATTGGAGGACAACTGGCTGATTATTTAAGAAGCCGAAAGATTTTGACCACAACTGCT
    1141    ---------+---------+---------+---------+---------+---------+ 1200
            GGGTAACCTCCTGTTGACCGACTAATAAATTCTTCGGCTTTCTAAAACTGGTGTTGACGA a         P  I  G  G  Q  L  A  D  Y  L  R  S  R  K  I  L  T  T  T  A  -

BspHI
                  |
            GTCAGAAAGATCATGAATTGTGGAGGCTTTGGCATGGAGGCAACCTTGCTCCTGGTGGTT
    1201    ---------+---------+---------+---------+---------+---------+ 1260
            CAGTCTTTCTAGTACTTAACACCTCCGAAACCGTACCTCCGTTGGAACGAGGACCACCAA a         V  R  K  I  M  N  C  G  G  F  G  M  E  A  T  L  L  L  V  V  -

BstXI
                        |
            GGGTTTTCCCATACCAAAGGAGTGGCTATCTCCTTCCTGGTGCTTGCTGTAGGATTTAGT
    1261    ---------+---------+---------+---------+---------+---------+ 1320
            CCCAAAAGGGTATGGTTTCCTCACCGATAGAGGAAGGACCACGAACGACATCCTAAATCA a         G  F  S  H  T  K  G  V  A  I  S  F  L  V  L  A  V  G  F  S  -

GGCTTTGCAATTTCAGGTTTCAATGTCAACCACCTGGACATTGCTCCACGATATGCCAGC
    1321    ---------+---------+---------+---------+---------+---------+ 1380
            CCGAAACGTTAAAGTCCAAAGTTACAGTTGGTGGACCTGTAACGAGGTGCTATACGGTCG a         G  F  A  I  S  G  F  N  V  N  H  L  D  I  A  P  R  Y  A  S  -

XcmI
           |
            ATCCTCATGGGGATCTCAAATGGCGTGGGAACCCTCTCTGGAATGGTTTGTCCCCTCATT
    1381    ---------+---------+---------+---------+---------+---------+ 1440
            TAGGAGTACCCCTAGAGTTTACCGCACCCTTGGGAGAGACCTTACCAAACAGGGGAGTAA a         I  L  M  G  I  S  N  G  V  G  T  L  S  G  M  V  C  P  L  I  -
```

Fig. 1 cont'd

```
                              SmaI
                        XmaI  |             XmnI
                         |    |              |
              GTTGGTGCAATGACAAAGCACAAGACCCGGGAAGAATGGCAGAATGTGTTCCTCATAGCA
       1441   ---------+---------+---------+---------+---------+---------+  1500
              CAACCACGTTACTGTTTCGTGTTCTGGGCCCTTCTTACCGTCTTACACAAGGAGTATCGT a           V  G  A  M  T  K  H  K  T  R  E  E  W  Q  N  V  F  L  I  A   -

BsiHKAI             MlyI
                 ApaLI   |                 PleI|
                   |     |                  | |
              GCCCTGGTGCACTACAGTGGAGTCATCTTCTACGGGGTCTTTGCTTCTGGGGAAAAACAG
       1501   ---------+---------+---------+---------+---------+---------+  1560
              CGGGACCACGTGATGTCACCTCAGTAGAAGATGCCCCAGAAACGAAGACCCCTTTTTGTC a           A  L  V  H  Y  S  G  V  I  F  Y  G  V  F  A  S  G  E  K  Q   -

BmrI                          BplI
                       |                             |
              GACTGGGCTGATCCAGAGAATCTCTCTGAGGAGAAATGTGGAATCATTGACCAAGATGAA
       1561   ---------+---------+---------+---------+---------+---------+  1620
              CTGACCCGACTAGGTCTCTTAGAGAGACTCCTCTTTACACCTTAGTAACTGGTTCTACTT a           D  W  A  D  P  E  N  L  S  E  E  K  C  G  I  I  D  Q  D  E   -

BsssI
                               |
              TTAGCCGAGGAAACAGAACTCAACCACGAGGCTTTCGTAAGTCCCAGAAAGAAGATGTCT
       1621   ---------+---------+---------+---------+---------+---------+  1680
              AATCGGCTCCTTTGTCTTGAGTTGGTGCTCCGAAAGCATTCAGGGTCTTTCTTCTACAGA a           L  A  E  E  T  E  L  N  H  E  A  F  V  S  P  R  K  K  M  S   -

BbsI         EciI
                                             |            |
              TATGGAGCCACCACCCAGAATTGTGAGGTCCAGAAGACGGATCGGAGACAACAGAGAGAA
       1681   ---------+---------+---------+---------+---------+---------+  1740
              ATACCTCGGTGGTGGGTCTTAACACTCCAGGTCTTCTGCCTAGCCTCTGTTGTCTCTCTT a           Y  G  A  T  T  Q  N  C  E  V  Q  K  T  D  R  R  Q  Q  R  E   -

TaqI
                   |
              TCCGCCTTCGAGGGGGAGGAGCCATTATCCTACCAGAATGAAGAGGACTTTTCAGAAACA
       1741   ---------+---------+---------+---------+---------+---------+  1800
              AGGCGGAAGCTCCCCCTCCTCGGTAATAGGATGGTCTTACTTCTCCTGAAAAGTCTTTGT a           S  A  F  E  G  E  E  P  L  S  Y  Q  N  E  E  D  F  S  E  T   -
```

*Fig. 1 cont'd*

```
                          BbvCI
                          Bpu10I
                            |
           TCTTAACGTGCATCTTCCCCTCAGCTTACAACCAGAAGTCTCCACACCCATTGCTTTTCC
      1801 ---------+---------+---------+---------+---------+---------+ 1860
           AGAATTGCACGTAGAAGGGGAGTCGAATGTTGGTCTTCAGAGGTGTGGGTAACGAAAAGG a          S  *  R  A  S  S  P  Q  L  T  T  R  S  L  H  T  H  C  F  S   -

PflMI
                |
           CATACCTTGGCCTTCCAGGGGGCCAAATCACAGGAAAGGGGGAGACTAAATCAACAACAG
      1861 ---------+---------+---------+---------+---------+---------+ 1920
           GTATGGAACCGGAAGGTCCCCCGGTTTAGTGTCCTTTCCCCCTCTGATTTAGTTGTTGTC a          H  T  L  A  F  Q  G  A  K  S  Q  E  R  G  R  L  N  Q  Q  Q   -

BsaI
                                                                |
           AGAAGAAAAATGCCTTCTTACAAAGATGGGCGTATGGATCTTGGTCTCAGTTAATTAGAT
      1921 ---------+---------+---------+---------+---------+---------+ 1980
           TCTTCTTTTTACGGAAGAATGTTTCTACCCGCATACCTAGAACCAGAGTCAATTAATCTA a          R  R  K  M  P  S  Y  K  D  G  R  M  D  L  G  L  S  *  L  D   -

BclI                        MfeI
             |                           |
           AGTTGATCATATTTTTTTTGGGGGGGGCAATTGGGCATTGGCTGTTGAGCCTTCTCTCAA
      1981 ---------+---------+---------+---------+---------+---------+ 2040
           TCAACTAGTATAAAAAAAACCCCCCCCGTTAACCCGTAACCGACAACTCGGAAGAGAGTT a          S  *  S  Y  F  F  W  G  G  Q  L  G  I  G  C  *  A  F  S  Q   -

AAGAACAATTTATTCAGGAAGAAATGGCTAGAAGAATAAGGAGTGGCTTGTTGCTCAAAT
      2041 ---------+---------+---------+---------+---------+---------+ 2100
           TTCTTGTTAAATAAGTCCTTCTTTACCGATCTTCTTATTCCTCACCGAACAACGAGTTTA a          K  N  N  L  F  R  K  K  W  L  E  E  *  G  V  A  C  C  S  N   -

Eco57I      TatI         BpmI
                         |           |            |
           AAACACTGAAGAAATCCCTCTTTGGTCTGGAGAAGAGTACATGGTGGTTGCCACCCCATC
      2101 ---------+---------+---------+---------+---------+---------+ 2160
           TTTGTGACTTCTTTAGGGAGAAACCAGACCTCTTCTCATGTACCACCAACGGTGGGGTAG a          K  H  *  R  N  P  S  L  V  W  R  R  V  H  G  G  C  H  P  I   -
```

*Fig. 1 cont'd*

```
                                                                EcoO109I
           EcoRV                       EcoNI                     PspOMI
             |                           |                         |
           TCCAAGGATATCCATGTAGAGGACAATCTCTGCAACCTAATGAAGGGAATCACTCATGGG
    2161   ---------+---------+---------+---------+---------+---------+   2220
           AGGTTCCTATAGGTACATCTCCTGTTAGAGACGTTGGATTACTTCCCTTAGTGAGTACCC a           S  K  D  I  H  V  E  D  N  L  C  N  L  M  K  G  I  T  H  G   -

ApaI
     EcoO109I    |
          | |   |
           GGCCCCTTGGTTGTGCCAGGTGCTTTATGAACATTCTTATTTAACTCCCACACCCTAATAT
    2221   ---------+---------+---------+---------+---------+---------+   2280
           CCGGGGAACCAACACGGTCCACGAAATACTTGTAAGAATAAATTGAGGGTGTGGGATTATA a           G  P  W  L  C  Q  V  L  Y  E  H  S  Y  L  T  P  T  P  *  Y   -

AGTTATTGTACCCATTTTACAACTAAGAACATTAAATGACTAGGTTGGCCCACCCAAGGT
    2281   ---------+---------+---------+---------+---------+---------+   2340
           TCAATAACATGGGTAAAATGTTGATTCTTGTAATTTACTGATCCAACCGGGTGGGTTCCA a           S  Y  C  T  H  F  T  T  K  N  I  K  *  L  G  W  P  T  Q  G   -

TGTCCTCTCAGAGCCAAAGCTGAGACTGGCAGATGACCAGGAGTTTTAGGAAGGAAGGAA
    2341   ---------+---------+---------+---------+---------+---------+   2400
           ACAGGAGAGTCTCGGTTTCGACTCTGACCGTCTACTGGTCCTCAAAATCCTTCCTTCCTT a           C  P  L  R  A  K  A  E  T  G  R  *  P  G  V  L  G  R  K  E   -

GGAAGGAAGGAAGGAAGGAAGGAAGGAAGGAAGGAAGGAAGGAAGGGTTCAGTTGAGTGT
    2401   ---------+---------+---------+---------+---------+---------+   2460
           CCTTCCTTCCTTCCTTCCTTCCTTCCTTCCTTCCTTCCTTCCTTCCCAAGTCAACTCACA a           G  R  K  E  G  R  K  E  G  R  K  E  G  R  K  G  S  V  E  C   -

AGGGTCATTTTCAATGACAAAAACAAAAACTGGAATCAGTTGGTTTGTGGGTAATTCCAT
    2461   ---------+---------+---------+---------+---------+---------+   2520
           TCCCAGTAAAAGTTACTGTTTTTGTTTTTGACCTTAGTCAACCAAACACCCATTAAGGTA a           R  V  I  F  N  D  K  N  K  N  W  N  Q  L  V  C  G  *  F  H   -

SphI
                              |
           GTTTGGTCAAGGGTGTGTGCATGCAAACGTGTATGTGCGTGTGTGTGTGTTTGTGTGTTT
    2521   ---------+---------+---------+---------+---------+---------+   2580
           CAAACCAGTTCCCACACACGTACGTTTGCACATACACGCACACACACACAAACACACAAA a           V  W  S  R  V  C  A  C  K  R  V  C  A  C  V  C  V  C  V  F   -
```

Fig. 1 cont'd

```
           GNGTGTNAGNNNGNATNANAANAAAAN
2581  ------------+------------+------- 2607
           CNCACANTCNNNCNTANTNTTNTTTTN
```

Fig. 1 cont'd

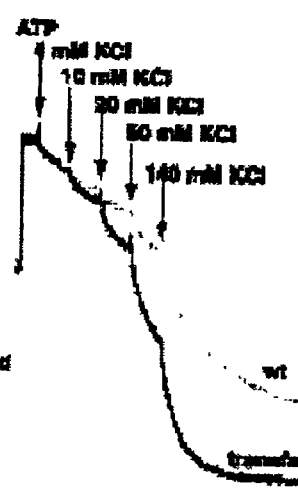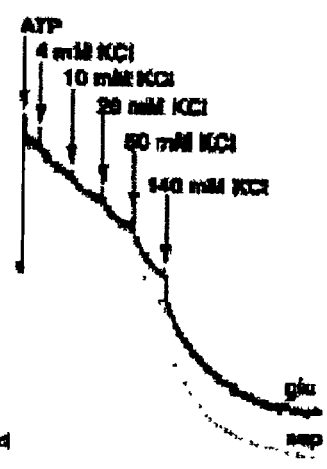
*Fig. 5A*  *Fig. 5B*  *Fig. 5C*
*Fig. 5A, 5B, and 5C*

Fig. 6A

VGLUT2     VGLUT1

Fig. 13A
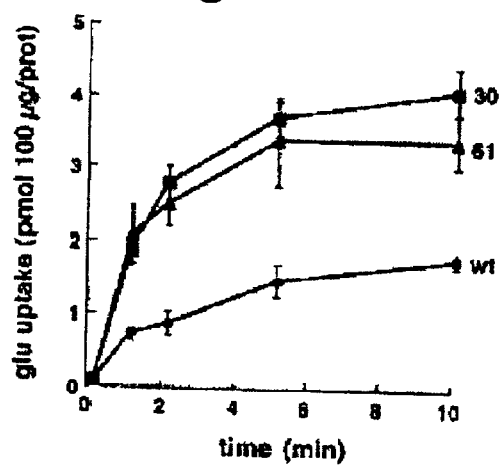
Fig. 13B
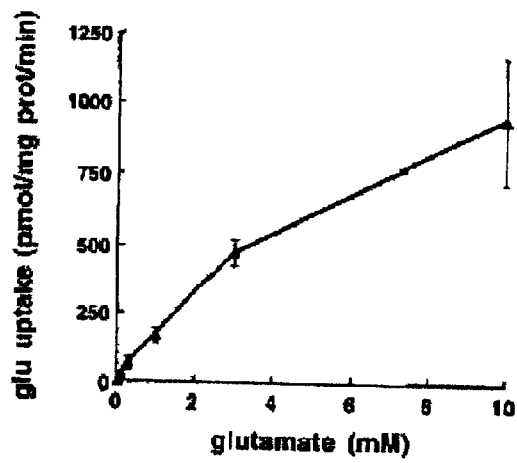
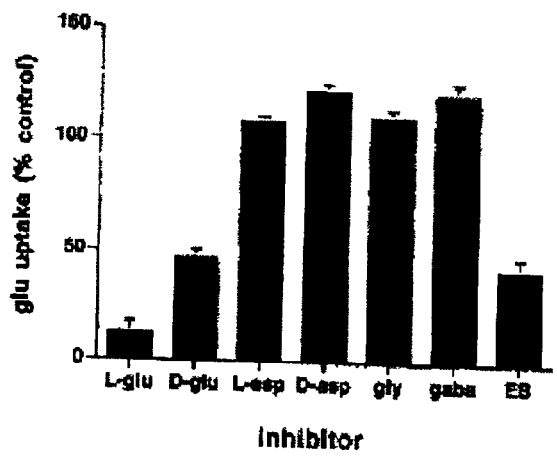
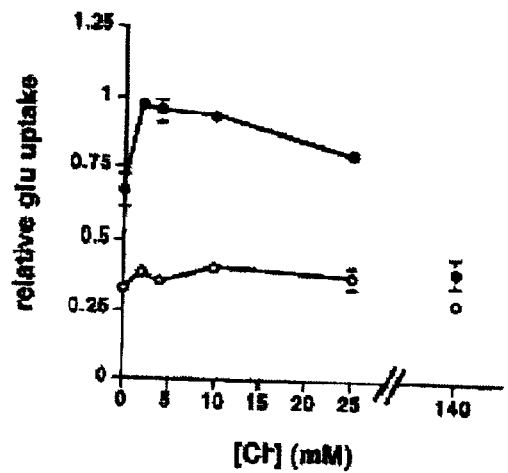
Fig. 13C
Fig. 13D
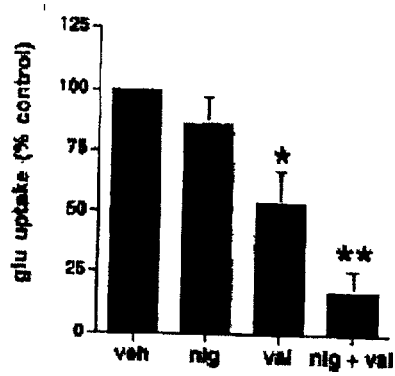
Fig. 13E

GLUTAMATE TRANSPORTERS

CROSS-REFERENCE TO RELATED APPLICATIONS

This application claims priority to and benefit of U.S. Patent Application No: 60/220,556, filed on Jul. 25, 2000, which is incorporated herein by reference in its entirety for all purposes.

STATEMENT AS TO RIGHTS TO INVENTIONS MADE UNDER FEDERALLY SPONSORED RESEARCH AND DEVELOPMENT

This work was supported by National Institutes of Health Grants NS16033, MH01365, and NS02034. the Government of the United States of America may have certain rights in this invention.

FIELD OF THE INVENTION

This invention relates to the field of neurobiology. In particular this invention pertains to the identification of a number of novel glutamate transporters.

BACKGROUND OF THE INVENTION

Excitatory neurotransmission involves the exocytotic release of synaptic vesicles filled with glutamate. Glutamate is synthesized in the cytoplasm, and undergoes transport into synaptic vesicles for quantal release. Like the uptake of other classical transmitters, vesicular glutamate transport depends on a proton electrochemical gradient ($\Delta\mu_{H+}$) generated by the vacuolar H$^+$-ATPase (Disbrow et al. (1982) *Biochemical and Biophysical Res. Commun.*, 108: 1221–1227; Naito and Ueda (1983) *J. Biol. Chem.* 258: 696–6990). However, unlike the uptake of monoamines and acetylcholine, vesicular glutamate transport relies predominantly on the electrical component of this gradient ($\Delta\Psi$) rather than the chemical component ($\Delta$pH) (Carlson et al. (1989) *J. Biol. Chem.* 264: 7369–7376; Maycox et al. (1988) *J. Biol. Chem.* 263: 15423–15428). Consistent with this different mechanism, the two protein families responsible for vesicular uptake of monoamines, ACh and γ-aminobutyric acid (GABA) (Liu and Edwards (1997) *Ann. Rev. Neurosci.* 20: 125–156; Reimer et al. (1998) *Curr. Opin. Neurobiol.* 8: 405–412; Schuldiner et al. (1995) *Physiol. Rev.* 75, 369–392; Varoqui et al., (1994) *FEBS Lett.* 342: 97–102) have not been found to include a glutamate transporter.

SUMMARY OF THE INVENTION

This invention pertains to the identification of a family of novel glutamate transporters. In particular, certain brain-specific Na+-dependent phosphate transporter are shown to be glutamate transporters. Designated herein as VGLUT glutamate transporters, members of this family include, but are not limited to VGLUT1 (formerly BNPI), VGLUT2 (formerly DNPI), and VGLUT3.

The VGLUT transporters of this invention provide good targets to screen for agents that modulate (e.g. upregulate or downregulate) glutamate uptake by a cell (e.g. by a neuron). Thus, in one embodiment, this invention provides a method of screening for an agent that modulates the uptake of glutamate into a cell (e.g. into a synaptic vesicle). The method preferably involves contacting a cell comprising a nucleic acid selected from the group consisting of VGLUT1, VGLUT2, and VGLUT3 with a test agent; and detecting expression or activity of VGLUT1, VGLUT2, or VGLUT3 where an increase or decrease in the expression or activity of VGLUT1, VGLUT2, or VGLUT3 as compared to a control indicates that the test agent modulates the uptake of glutamate into a cell. The control can be a positive or a negative control. In certain embodiments, the control is a negative control comprising contacting a cell at a lower concentration or in the absence concentration of the test agent. Preferred cells include somatic cells or oocytes. Particularly preferred cells include vertebrate cells, more preferably mammalian (e.g. human, rabbit, mouse, goat, equine, porcine, feline, canine, etc.) cells.

In certain preferred embodiments, the detecting comprises detecting a VGLUT (e.g. VGLUT1 and/or VGLUT2, and/or VGLUT3, etc.) nucleic acid and/or a (VGLUT) polyeptide (e.g. VGLUT1 polypeptide and/or VGLUT2 polypeptide, and/or VGLUT3 polypeptide, etc.) VGLUT1 polypeptide, a VGLUT2 polypeptide, or a VGLUT3 polypeptide. In certain embodiments, the VGLUT nucleic acid is detected via a nucleic acid hybridization (e.g., a Northern blot, a Southern blot using DNA derived from the VGLUT1, VGLUT2, or VGLUT3 mRNA, an array hybridization, an affinity chromatography, an in situ hybridization, etc.) and/or a nucleic acid amplification (e.g. PCR, LCR, etc.).

In preferred embodiments, the VGLUT polypeptide is detected via a method such as capillary electrophoresis, Western blot, mass spectroscopy, ELISA, immunochromatography, immunohistochemistry, thin layer chromatography (TLC), and the like. In preferred embodiments, the VGLUT polypeptide activity involves detecting glutamate transport in a cell expressing an endogenous or a heterologous VGLUT polypeptide (e.g., VGLUT1, VGLUT2, VGLUT3, etc.). In certain embodiments, the test agent is not one or more of the following: an antibody, a nucleic acid, a protein, and an agent that alters $\Delta$pH or $\Delta\Psi$. In particularly embodiments the test agent is a small organic molecule. In certain embodiments, the methods further comprise comparing the level of expression or activity of VGLUT1 with the level of expression or activity of VGLUT2 and/or VGLUT3.

In another embodiment, this invention provides a method of prescreening for a potential modulator of glutamate transporter activity (e.g. glutamate uptake into a synaptic vesicle). The method preferably involves contacting a VGLUT glutamate transporter polypeptide (e.g. VGLUT1, VGLUT2, VGLUT3, etc.) or a nucleic acid encoding a VGLUT glutamate transporter polypeptide with a test agent; and detecting binding (e.g. specific binding) of the test agent to the VGLUT glutamate transporter polypeptide or to the nucleic acid encoding a VGLUT glutamate transporter polypeptide where specific binding of said test agent to the VGLUT glutamate transporter polypeptide or VGLUT nucleic acid indicates that the test agent is a potential modulator of glutamate transporter activity. The method can, optionally, further involve recording test agents that specifically bind to the VGLUT glutamate transporter polypeptide or to the nucleic acid encoding a VGLUT glutamate transporter polypeptide in a database of candidate modulators of glutamate transporter activity. In certain embodiments, the test agent is not one or more of the following: an antibody, a nucleic acid, a protein, and an agent that alters $\Delta$pH or $\Delta\Psi$. In particularly embodiments the test agent is a small organic molecule. The detecting can involve detecting specific binding of the test agent to the VGLUT nucleic acid (e.g. via Northern blot, a Southern blot using DNA derived from the VGLUT mRNA, array hybridization, affinity chromatography, in situ hybridization, etc.). The detecting can also involve detecting specific binding of the test agent to the VGLUT glutamate transporter polypeptide (e.g. via capillary electrophoresis, Western blot, mass spectroscopy, ELISA, immunochromatography, thin layer chromatography, and immunohistochemistry). In certain embodiments, the test agent is contacted directly to the VGLUT glutamate transporter polypeptide or to the nucleic acid encoding a VGLUT glutamate transporter polypeptide. in certain embodiments, the test agent is contacted to a cell containing the VGLUT glutamate transporter polypeptide or to said nucleic acid encoding a VGLUT glutamate transporter polypeptide. The cell can be a cell cultured ex vivo.

In still another embodiment, this invention provides a cell comprising a heterologous nucleic acid encoding a glutamate transporter wherein said glutamate transporter is selected from the group consisting of VGLUT1, VGLUT2, and VGLUT3. Preferred cells include somatic cells (e.g. nerve cells), or oocytes. Particularly preferred cells include vertebrate cells, more preferably mammalian (e.g. human, rabbit, mouse, goat, equine, porcine, feline, canine, etc.) cells. In a particularly preferred embodiment, the cell transports glutamate via the heterologous VGLUT glutamate transporter. In one embodiment, the cell is a pheochromocytoma PC12 cell.

In yet another embodiment, this invention provides a method of increasing glutamate transport by a mammalian cell. The method can involve transfecting the cell with a nucleic acid encoding a VGLUT polypeptide selected from the group consisting of VGLUT1, VGLUT2, and VGLUT3. The VGLUT nucleic acid is preferably operably linked to a constitutive, tissue-specific or inducible promoter.

This invention also provides a method of decreasing glutamate uptake into a cell. The method involves down-regulating expression or activity of a VGLUT polypeptide in the cell. In certain embodiments, the inhibiting comprises a method selected from the group consisting of contacting a VGLUT nucleic acid with a ribozyme that specifically cleaves said VGLUT nucleic acid, contacting a VGLUT nucleic acid with a catalytic DNA that specifically cleaves said VGLUT nucleic acid, transfecting a cell comprising an VGLUT gene with a nucleic acid that inactivates the VGLUT gene by homologous recombination with the VGLUT gene, transfecting a cell comprising a with a nucleic acid encoding an intrabody that specifically binds a VGLUT polypeptide, and transfecting the cell with a VGLUT antisense molecule.

This invention also provides a kit for screening for compounds that modulate glutamate transport. Preferred kits include a cell that expresses a VGLUT glutamate transporter selected from the group consisting of VGLUT1, VGLUT2, and VGLUT3; and a detection moiety selected from the group consisting of an antibody that specifically binds to the VGLUT glutamate transporter, a nucleic acid that specifically binds to a nucleic acid encoding the VGLUT glutamate transporter, a primer that specifically amplifies a nucleic acid encoding said VGLUT glutamate transporter or a fragment thereof, and a labeled glutamate. The cell is preferably a cell comprising a heterologous nucleic acid encoding the glutamate transporter. The kit can also include instructional materials providing protocols for screening for modulators of a VGLUT glutamate transporter and teaching that such modulators alter glutamate transport.

This invention also provides VGLUT knockout animals. Preferred knockouts include a mammal (e.g., an equine, a bovine, a rodent, a porcine, a lagomorph, a feline, a canine, a murine, a caprine, an ovine, a non-human primate, etc.) comprising a disruption in an endogenous glutamate transporter gene selected from the group consisting of VGLUT1, VGLUT2, and VGLUT3, where the disruption results in the knockout mammal exhibiting decreased expression of a VGLUT glutamate transporter as compared to a wild-type animal. In certain embodiments, the disruption an insertion, a deletion, a frameshift mutation, a substitution, or a stop codon. In certain embodiments, the disruption comprises an insertion of an expression cassette into said endogenous glutamate transporter gene. The expression cassette can comprise a selectable marker. The expression cassette can comprise a neomycin phosphotransferase gene operably linked to at least one regulatory element. The disruption can be in a somatic cell and/or in a germ cell. The mammal can be heterozygous or homozygous for the disrupted glutamate transporter gene.

This invention also provides a method of inhibiting glutamate uptake into a cell. The method can comprise contacting a cell comprising a synaptic vesicle with an agent that inhibits expression or activity of a VGLUT polypeptide. In certain embodiments, the agent is not one or more of the following: an antibody, a nucleic acid, a protein, and an agent that alters $\Delta pH$ or $\Delta \Psi$. In particularly embodiments the test agent is a small organic molecule, a VGLUT antisense molecule, a VGLUT ribozyme, a VGLUT catalytic DNA, an anti-VGLUT antibody, and a nucleic acid that disrupts a VGLUT gene by homologous recombination.

Also provided is a method of increasing glutamate uptake into a cell where the method comprises contacting the cell comprising with an agent that increases VGLUT glutamate transporter expression or activity (e.g. an vector encoding a heterologous VGLUT glutamate transporter).

DEFINITIONS

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10):1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 1419), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111 :2321, O-methylphophoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature*, 365: 566; Carlsson et al. (1996) *Nature* 380: 207). Other analog nucleic acids include those with positive backbones (Denpcy et al. (1995)

Proc. Natl. Acad. Sci. USA 92: 6097; non-ionic backbones (U.S. Pat. Nos. 5,386,023, 5,637,684, 5,602,240, 5,216,141 and 4,469,863; Angew (1991) Chem. Intl. Ed. English 30: 423; Letsinger et al. (1988) J. Am. Chem. Soc. 110:4470; Letsinger et al. (1994) Nucleoside & Nucleotide 13:1597; Chapters 2 and 3, ASC Symposium Series 580, "Carbohydrate Modifications in Antisense Research", Ed. Sanghui and Cook; Mesmaeker et al. (1994), Bioorganic & Medicinal Chem. Lett. 4: 395; Jeffs et al. (1994) J. Biomolecular NMR 34:17; Tetrahedron Lett. 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Sanghui and Cook. Nucleic acids containing one or more carbocyclic sugars are also included within the definition of nucleic acids (see Jenkins et al. (1995), Chem. Soc. Rev. pp169–176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

A "VGLUT transporter" refers to a member of a glutamate transporter family characterized by VGLUT1, VGLUT2, and VGLUT3. The VGLUT glutamate transporters belong to a larger family known as the type I phosphate transporters. However, particularly in view of the teachings provided herein, it is demonstrated that members of this family transport organic anions (such as sialic acid and glutamate) rather than inorganic phosphate. Within this family, the VGLUTs show much stronger sequence similarity (>50% amino acid identity to each other from C. elegans to mammals and >80% within mammals) than to other type I phosphate transporters such as sialin and NaPi-1 (35–45% amino acid identity). Thus, preferred VGLUT glutamate transporters of this invention show 50% or greater amino acid sequence identity, preferably 65% or greater amino acid sequence identity, more preferably 80% or greater amino acid sequence identity, still more preferably 90% or greater amino acid sequence identity, and most preferably 95% or greater amino acid sequence identity, to VGLUT1 and/or to VGLUT2 and/or to VGLUT3.

The term "VGLUT nucleic acid" refers to a nucleic acid encoding a VGLUT polypeptide (glutamate transporter) or to a nucleic acid derived therefrom. Thus, VGLUT nucleic acids include, but are not limited, to various VGLUT genes (e.g. VGLUT1, VGLUT2, and VGLUT3), a VGLUT RNA (e.g. VGLUT1 RNA, VGLUT2 RNA, and VGLUT3 RNA), a VGLUT cDNA, a VGLUT cRNA, and the like.

A "VGLUT1 nucleic" is a nucleic acid that encodes a polypeptide encoded by VGLUT1 (GenBank Accession No: AB032436) and homologs and orthologues thereof or to a nucleic acid derived therefrom. Thus, VGLUT1 nucleic acids include, but are not limited, to a VGLUT1 gene, a VGLUT1 cDNA, a VGLUT1 RNA, a VGLUT1 cRNA, an amplification produce produced from a VGLUT1 nucleic acid template, and the like. Similarly, a "VGLUT2 nucleic" is a nucleic acid that encodes a polypeptide encoded by VGLUT2 (GenBank Accession Nos: rat VGLUT2: AF271235; human VGLUT2: AB032435) and homologs and orthologues thereof or to a nucleic acid derived therefrom. A "VGLUT3 nucleic" is a nucleic acid that encodes a polypeptide encoded by VGLUT3 (GenBank Accession No: AL157942) and homologs and orthologues thereof or to a nucleic acid derived therefrom.

A "VGLUT protein or polypeptide" is a glutamate transporter protein encoded by a VGLUT nucleic acid. Similarly, a "VGLUT1, VGLUT2, or VGLUT3 protein or polypeptide" is a glutamate transporter protein encoded by a VGLUT1, VGLUT2, or VGLUT3 nucleic acid, respectively.

"BNPI" refers to a brain-specific inorganic phosphate transporter (see, e.g., Rosteck et al. (1994) Proc. Natl. Acad. Sci., USA, 91: 5607–5611; Glinn and Paul (1995) J. Neurochem, 65: 2358–2365 (1995); and Glinn et al.(1998) J. Neurochem., 70: 1850–1858). See also, GenBank accession number AB032436. BNPI is used herein synonymously with VGLUT1.

The phrase "detecting expression or activity of VGLUT" refers to detecting expression of a VGLUT nucleic acid (e.g. VGLUT1, and/or VGLUT2, and/or VGLUT3), detecting expression of a VGLUT protein (e.g. a VGLUT1 polypeptide, and/or a VGLUT2 polypeptide, and/or VGLUT3 polypeptide), or detecting activity of a VGLUT polypeptide.

The term "inhibit expression" when used with reference to inhibition of VGLUT (e.g. VGLUT1 and/or VGLUT2 and/or VGLUT3) refers to a reduction or blocking of VGLUT transcription, and/or translation, and/or formation or availability or activity of a VGLUT protein (e.g. VGLUT1 and/or VGLUT2 and/or VGLUT3).

The term "detecting a VGLUT mRNA or cDNA" refers to detecting and/or quantifying a VGLUT nucleic acid or a nucleic acid derived therefrom the quantification of which provides an indication of the expression level of the VGLUT nucleic acid. The term thus includes, but is not limited to detection of VGLUT mRNA, cDNA, VGLUT amplification products, and fragments of any of these.

The terms "binding partner", or "capture agent", or a member of a "binding pair" refers to molecules that specifically bind other molecules to form a binding complex such as antibody-antigen, lectin-carbohydrate, nucleic acid-nucleic acid, biotin-avidin, etc.

The term "specifically binds", as used herein, when referring to a biomolecule (e.g., protein, nucleic acid, antibody, etc.), refers to a binding reaction which is determinative of the presence biomolecule in heterogeneous population of molecules (e.g., proteins and other biologics). Thus, under designated conditions (e.g. immunoassay conditions in the case of an antibody or stringent hybridization conditions in the case of a nucleic acid), the specified ligand or antibody binds to its particular "target" molecule and does not bind in a significant amount to other molecules present in the sample.

The phrase "transport of glutamate into a cell" refers to the uptake of glutamate into a synaptic vesicle (e.g. of a nerve cell), or the uptake of glutamate into other kinds of cells, as well. Thus, for example, transport of glutamate into a cell can refer to the transport of glutamate into an oocyte (e.g. an oocytes expressing a heterologous VGLUT transporter) in which case, uptake is across the plasma membrane. In certain preferred embodiments, uptake is uptake by a mammalian cell.

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences. Stringent hybridization and stringent hybridization wash conditions in the context of nucleic acid hybridization are sequence dependent, and are different under different environmental parameters. An extensive guide to the hybridization of nucleic acids is found in, e.g., Tijssen (1993) *Laboratory Techniques in Biochemistry and Molecular Biology— Hybridization with Nucleic Acid Probes part I, chapt 2, Overview of principles of hybridization and the strategy of nucleic acid probe assays*, Elsevier, N.Y. (Tijssen ). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$. for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook (1989) *Molecular Cloning: A Laboratory Manual* (2nd ed.) Vol. 1–3, Cold Spring Harbor Laboratory, Cold Spring Harbor Press, NY, and detailed discussion, below), with the hybridization being carried out overnight. An example of highly stringent wash conditions is 0.15 M NaCl at 72° C. for about 15 minutes. An example of stringent wash conditions is a 0.2× SSC wash at 65° C. for 15 minutes (see, e.g., Sambrook supra.) for a description of SSC buffer). Often, a high stringency wash is preceded by a low stringency wash to remove background probe signal. An example medium stringency wash for a duplex of, e.g., more than 100 nucleotides, is 1× SSC at 45° C. for 15 minutes. An example of a low stringency wash for a duplex of, e.g., more than 100 nucleotides, is 4× to 6× SSC at 40° C. for 15 minutes.

The term "test agent" refers to an agent that is to be screened in one or more of the assays described herein. The agent can be virtually any chemical compound. It can exist as a single isolated compound or can be a member of a chemical (e.g. combinatorial) library. In a particularly preferred embodiment, the test agent will be a small organic molecule.

The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

The term database refers to a means for recording and retrieving information. In preferred embodiments the database also provides means for sorting and/or searching the stored information. The database can comprise any convenient media including, but not limited to, paper systems, card systems, mechanical systems, electronic systems, optical systems, magnetic systems or combinations thereof. Preferred databases include electronic (e.g. computer-based) databases. Computer systems for use in storage and manipulation of databases are well known to those of skill in the art and include, but are not limited to "personal computer systems", mainframe systems, distributed nodes on an inter- or intranet, data or databases stored in specialized hardware (e.g. in microchips), and the like.

The term "heterologous" as it relates to nucleic acid sequences such as coding sequences and control sequences, denotes sequences that are not normally associated with a region of a recombinant construct, and/or are not normally associated with a particular cell. Thus, a "heterologous" region of a nucleic acid construct is an identifiable segment of nucleic acid within or attached to another nucleic acid molecule that is not found in association with the other molecule in nature. For example, a heterologous region of a construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a host cell transformed with a construct which is not normally present in the host cell would be considered heterologous for purposes of this invention.

The term "recombinant" or "recombinantly expressed" when used with reference to a cell indicates that the cell replicates or expresses a nucleic acid, or expresses a peptide or protein encoded by a nucleic acid whose origin is exogenous to the cell. Recombinant cells can express genes that are not found within the native (non-recombinant) form of the cell. Recombinant cells can also express genes found in the native form of the cell wherein the genes are re-introduced into the cell by artificial means, for example under the control of a heterologous promoter.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. With respect to the peptides of this invention sequence identity is determined over the full length of the peptide.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman (1988) *Proc. Natl. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle (1987) *J. Mol. Evol.* 35:351–360. The method used is similar to the method described by Higgins & Sharp (1989) *CABIOS* 5: 151–153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al. (1990) *J. Mol. Biol.* 215: 403–410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Natl. Acad. Sci. USA*, 90: 5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

The term "operably linked" as used herein refers to linkage of a promoter to a nucleic acid sequence such that the promoter mediates/controls transcription of the nucleic acid sequence.

The term "induce" expression refers to an increase in the transcription and/or translation of a gene or cDNA.

BRIEF DESCRIPTION OF THE DRAWINGS

FIG. 1 shows a VGLUT3 nucleic acid (SEQ ID NO:1), its complement (SEQ ID NO:2), and a VGLUT3 amino acid sequence (SEQ ID NO:3).

FIG. 2A: Membranes prepared from transfected PC12 cells (lines 2, 16, and 45, solid symbols) accumulate two to four times the $^3$H-glutamate (glu) that membranes from untransfected cells accumulate [wild type (wt), open squares; prot, protein].

FIG. 2B: The initial maximal rate of transport by BNPI at 1 min (Vo) saturates with increasing concentrations of $^3$H-glutamate. The uptake by untransfected cell membranes was subtracted as background uptake. (Inset) Lineweaver-Burke analysis indicates a Km of ~2 mM

FIG. 4A: Transport of $^3$H-glutamate at 5 min by membranes expressing BNPI shows a strong dependence on chloride concentration, with an optimum of ~2 to 4 mM. The experiments were performed with varying proportions of 0.14 M potassium gluconate and 0.14 M KCl in the standard reaction buffer, as described herein, without sucrose to produce the different concentrations of chloride and to maintain constant osmolarity. The uptake by untransfected as well as transfected cells was normalized to maximal uptake by the transfected cells. FIG. 4B: With membranes preloaded with 4 mM KCl, the proton ionophore nigericin (5 μM) increases the uptake of $^3$H-glutamate by membranes from transfected cells, whereas valinomycin (20 μM), which eliminates the membrane potential (ΔΨ), reduces uptake; the combination essentially eliminates transport mediated by BNPI. The results are presented as a percentage of uptake by transfected cells in the absence of ionophore and represent the average of at least two experiments performed in duplicate on different membrane preparations. The error bars indicate the standard deviation.

FIGS. 5A through 5D illustrate the role of BNPI in acidification by glutamate and chloride. FIG. 5A: The quenching of acridine orange fluorescence shows that glutamate (10 mM) acidifies membranes expressing BNPI (black traces) but not membranes from untransfected cells (wt, gray traces). A high concentration of chloride (90 mM) also produces more acidification of BNPI-expressing vesicles than control vesicles. Arrows indicate the times of addition of ATP to a final concentration of 4 mM and of KCl to the final concentrations shown. FIG. 5B: Membranes expressing BNPI (black traces) show more acidification with increasing concentrations of chloride than do control membranes (gray traces). BNPI-containing membranes also reach a steady-state pH early in the course of the experiment, whereas control membranes show a declining pH, even at late times. Arrows indicate the addition of ATP and KCl as described in (5A). FIG. 5C: Glutamate (10 mM) (black traces), but not aspartate (10 mM) (gray traces), reduces the acidification of BNPI-expressing membranes by chloride. Arrows indicate the additions, as in (5A). FIG. 5D: Quantitation of the chloride conductance. Acridine orange fluorescence quenching shows that transfected cell membranes (open bars, right) exhibit a substantially greater rate of chloride-dependent acidification than untransfected cell membranes exhibit (open bars, left) at higher concentrations of KCl (20, 50, and 140 mM). Glutamate (10 mM) (black bars) reduces the rate of acidification in transfected cell membranes (right) but not in untransfected cell membranes (left). In contrast, the nontransported aspartate (10 mM) (gray bars) has little effect on the acidification of membranes expressing BNPI (right). The rate of fluorescence quenching was determined by averaging the change in fluorescence units over 12 consecutive 5-s intervals beginning 15 s after each addition of KCl. Error bars indicate the standard error of the mean.

FIGS. 6A and 6B show that DNPI belongs to a subfamily of type I phosphate transporters. FIG. 6A shows that the predicted amino acid sequence of rat DNPI/VGLUT2 (SEQ ID NO:4) exhibits more similarity to rat VGLUT1 (SEQ ID NO:5) and C. elegans EAT-4 (SEQ ID NO:6) than to other type I phosphate transporters including human sialin (SEQ ID NO:7) and rat NaPi-1 (SEQ ID NO:8). The sequences were aligned using PILEUP (GCG). Black boxes indicate identical residues and gray boxes conservative substitutions. The solid lines above rat DNPI/VGLUT2 reflect the location of putative transmembrane domains (predicted by Kyte-Doolittle analysis of hydropathy). The dashed lines indicate hydrophobic segments too short to span the membrane that might form re-entrant loops. The asterisk indicates a putative glycosylation site. FIG. 6B shows a dendrogram showing the amino acid sequence relationship between rat VGLUT2 and rat VOLUTI, C. elegans EAT4, human sialin and rabbit NaPi-1. The percentage shown in parentheses indicates the percent identity to rat VGLUT2.

FIG. 10A: After differential centrifugation of rat brain extracts prepared by the hypotonic lysis of synaptosomes (Huttner et al. (1983) *J. Cell Biol.* 96: 1374–1388), equal amounts of protein from each fraction were analyzed by Western blotting. Like VGLUT1, DNPI/VGLUT2 cosediments with the synaptic vesicle protein synaptophysin (syp), the plasma membrane t-SNARE syntaxin (stx) and the NMDA receptor subunit NR1 in the washed synaptosome fraction P2'. After hypotonic lysis, both DNPI and VGLUT1 appear enriched in a population of light membranes (LP2) along with synaptophysin whereas syntaxin and NR1 fractionate with heavier membranes (including the plasma membrane) in LP1. However, DNPI and VGLUT1 also appear at higher levels in LP1 than synaptophysin, suggesting localization on the plasma membrane as well as synaptic vesicles. In addition, DNPI appears at higher levels than VGLUT1 on a population of crude membranes lighter than synaptosomes (S2). FIG. 10B: Fractions 1–16 were collected from the top of a 5–25% glycerol velocity gradient used to fractionate P2' (Clift-O'Grady et al. (1990) *J. Cell Biol.* 110: 1693–1703). Western analysis of equal volumes from each fraction shows that DNPI cofractionates with VGLUT1 and synaptophysin in fractions 3–7. In contrast, the plasma membrane protein syntaxin occurs predominantly at the bottom of the gradient. However, DNPI and VGLUT1 show proportionally more immunoreactivity at the bottom of the gradient than synaptophysin, suggesting expression on membranes in addition to synaptic vesicles.

FIG. 11A: Immunogold localization in the molecular layer of the cerebellar cortex shows DNPI/VGLUT2 on synaptic vesicles in climbing fiber boutons (Cf), but not in parallel fiber boutons (Pf). Several of the gold particles are indicated (arrows). There is no apparent selectivity of labeling among vesicles depending on their localization. Note the lack of particles over other tissue elements, including postsynaptic dendritic spines of Purkinje cells. Inset: high magnification view of a square in the main panel more clearly shows the small gold particles. FIG. 11B: VGLUT1 localizes to synaptic vesicles in parallel fiber boutons (left panel), but not in climbing fiber boutons (right panel). Scale bars: 200 nm.

FIGS. 13A through 13E show that DNPI catalyzes vesicular glutamate transport. FIG. 13A: Membranes prepared from two stable PC 12 transformants expressing DNPI/VGLUT2 (lines 30 and 61) accumulate substantially more $^3$H-L-glutamate than membranes from untransfected cells (wt). The results represent the average from three experiments performed in duplicate using membranes from different vesicle preparations. The error bars represent the standard error of the mean. FIG. 13B: The initial rate of uptake ($V_0$) (at 1 minute) saturates with increasing concentrations of L-glutamate (0.03–10 mM). Specific uptake was determined at each glutamate concentration by subtracting the background uptake by untransfected cell membranes from total uptake by membranes expressing DNPI. Lineweaver-Burke analysis indicates a Km 4.7±0.7 mM. The results represent the average of three experiments each performed in triplicate, and the error bars the standard error of the mean. FIG. 13C: L-Glutamate (L-glu), but not L-aspartate (L-asp), D-aspartate (D-asp), glycine (gly) or γ-aminobutyric acid (gaba) (all at 10 mM) markedly inhibits specific DNPI-mediated uptake of $^3$H-L-glutamate at 5 minutes. D-Glutamate (D-glu) (10 mM) and Evans Blue (EB) (4.5 μM) also significantly inhibit DNPI-mediated $^3$H-L-glutamate uptake. The results are expressed as a percentage of specific $^3$H-L-glutamate accumulated in the absence of inhibitor and represent the average +/− SEM of at least four independent determinations. FIG. 13D: The uptake of $^3$H-L-glutamate at 5 minutes by membranes expressing DNPI (closed circles) exhibits a biphasic dependence on chloride concentration. Untransfected cells (open circles) show no chloride dependence. Although specific uptake can be detected in the absence of added chloride, maximal uptake occurs at a chloride concentration of ~2 mM. In contrast, little or no specific uptake is detectable at 140 mM chloride. Activity was normalized to maximal uptake by the transfected cell membranes. Data represent the average +/− SEM of three experiments each performed in triplicate, with several of the smaller error bars obscured by the symbol indicating the mean. FIG. 13E: Uptake of $^3$H-glutamate by membranes expressing DNPI depends more on membrane potential than on the pH gradient. Membranes were preloaded with 4 mM KCl and specific uptake at 5 minutes was determined in the presence of either 1% ethanol (veh), 5 $\mu$M nigericin (nig), 20 $\mu$M valinomycin (val), or 5 $\mu$M nigericin and 20 $\mu$M valinomycin (nig+val). The uptake by membranes from untransfected cells was subtracted from uptake by membranes expressing DNPI. The results indicate the percentage of specific uptake obtained in the absence of ionophore (veh) and represent the average +/− SEM of three experiments each performed in triplicate. *$p<0.05$ compared to vehicle; **$p<0.01$ compared to valinomycin alone (two-tailed, paired Student's t test).

DETAILED DESCRIPTION

Figure 2A:
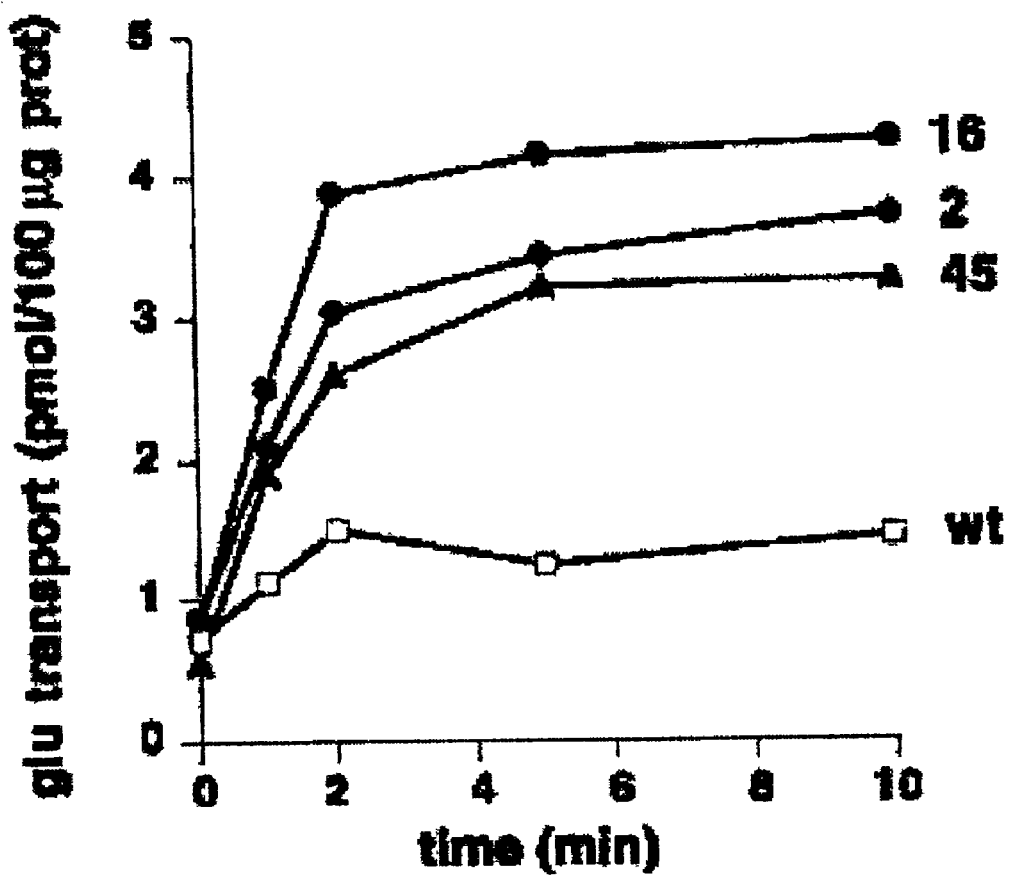
FIGS. 2A and 2B show that BNPI expression confers saturable glutamate uptake in PC12 cell membranes.

This invention pertains to the identification of a novel class of glutamate transporters. In particular, we have shown that proteins originally considered to perform an entirely different function, in fact, transport glutamate into synaptic vesicles. The brain-specific Na$^+$-dependent phosphate transporter (BNPI) was initially identified as a sequence upregulated in neurons by subtoxic concentrations of N-methyl-D-aspartate (Ni et al. (1994) *Proc. Natl. Acad. Sci., USA*, 91: 5607–5611). Expressed in Xenopus oocytes, BNPI confers Na$^+$-dependent uptake of inorganic phosphate (Pi), and was suggested to have a role in the maintenance of energy stores (Glinn et al. (1998) *J. Neurochem.* 70: 1850–1858; Glinn and Paul (1997) *Brain Res.* 757, 85–92) However, the selective expression of BNPI by only glutamate neurons (Ni et al. supra) raised the possibility of a more specific role in excitatory transmission. Genetic studies in *C. elegans* supported a role for the BNPI orthologue eat-4 in glutamate release (Avery (1993) *Genetics* 133: 897–917; Lee et al. (1999) *J. Neurosci.* 19: 159–67). The eat-4 mutant has a specific defect in glutamatergic transmission (Raizen and Avery, (1994) *Neuron* 12, 483–495), but shows normal sensitivity to iontophoretically applied glutamate (Dent et al. (1997) *EM BO J.*, 16: 5867–5879), further indicating a presynaptic defect. Consistent with a role in glutamate release, rat BNPI localizes to excitatory nerve terminals and specifically to synaptic vesicles (Bellocchio et al. (1998) *J. Neurosci.* 18: 8648–8659).

Although Pi uptake may have a specific role in glutamate production and release (Bellocchio et al. supra), BNPI belongs to the type I class of Pi transporters that appear to have functions in addition to Pi transport. In particular, other type I Pi transporters recognize organic anions with higher affinity than Pi (Bröer et al. (1998). *J. Memb. Biol.* 164: 71–77; Busch et al. (1996) *Proc. Natl. Acad. Sci., USA*, 93: 5347–5351; Mancini et al. (1989) *J. Biol. Chem.* 264: 15247–15254; Verheijen et al. (1999) *Nature Genetics* 23: 462–465). These observations suggested that BNPI might also have a function distinct from Pi uptake.

It was a discovery of this invention that BNPI transports glutamate into secretory vesicles with all of the properties previously demonstrated for glutamate uptake by native synaptic vesicles (see also, Bellocchio et al. (2000) *Science* 289: 957–960; Takamori et al. (2000) *Nature* 407: 189–194). In addition, heterologous expression of BNPI converts inhibitory GABAergic neurons to an excitatory phenotype. We therefore renamed BNPI vesicular glutamate transporter 1 (VGLUT1). It was also a discovery of this invention, however, that VGLUT1 is expressed by only a subset of glutamate neurons in the cortex, hippocampus and cerebellum, raising questions about the mechanism by which excitatory neurons in the thalamus, brainstem and elsewhere accumulate glutamate in synaptic vesicles.

In another embodiment, this invention provides a second protein that is a novel type I Pi transporter that also transports glutamate into synaptic vesicles. Induced during the differentiation of exocrine pancreas AR42J cells into neuroendocrine cells capable of insulin secretion, this differentiation-associated Na$^+$-dependent Pi transporter (DNPI) shows strong sequence similarity to VGLUT1 (see, e.g., Aihara (2000) *J. Neurochem.* 74: 2622–2625). Like VGLUT1, its expression is restricted to the nervous system and it confers Na$^+$-dependent Pi uptake when expressed in Xenopus oocytes (Aihara (2000) *J. Neurochem.* 74: 2622–2625). We demonstrate by in situ hybridization that DNPI is expressed by essentially all glutamate neurons not expressing VGLUT1, and in particular by neurons in the thalamus, hypothalamus and brainstem. Using an antibody that we raised to the protein, immunocytochemistry supports the localization of DNPI to synapses that appear largely distinct from those labeled for VGLUT1. In addition, we establish the localization of DNPI to synaptic vesicles by differential centrifugation, velocity gradient fractionation and immuno-electron microscopy. Further, heterologous expression of DNPI in PC12 cells confers vesicular glutamate transport with properties very similar to native synaptic vesicles and VGLUT1. We have thus renamed DNPI vesicular glutamate transporter 2 (VGLUT2). The expression of distinct VGLUT isoforms by complementary populations of excitatory neurons suggests that they define distinct modes of glutamate release.

In still another embodiment, this invention pertains to the identification of a third glutamate transporter, designated herein as VGLUT3 (see, e.g., FIG. 1). VGLUT1 (rat VGLUT1 Accession No: U07609, human VGLUT1 Accession No: NM_020309, AB032436), VGLUT2 (rat VGLUT2 accession No: AF271235, human Accession No: NM_020346.1, AB032435), and VGLUT3 (Accession No: AL157942), together identify a family of glutamate transporters, as described above. The VGLUT glutamate transporters of this invention are proteins that belong to a larger family known as the type I phosphate transporters. Within this family, the VGLUTs show much stronger sequence similarity (>50% amino acid identity to each other from *C. elegans* to mammals and >80% within mammals) than to other type I phosphate transporters such as sialin and NaPi-1 (35–45% amino acid identity).

The VGLUT glutamate transporters identified herein are useful in a wide variety of contexts. The excitatory neurotransmitter glutamate (Glu) is one of the most important in the brain, but in excess it can cause cell death or overexcitation resulting in epilepsy. The concentration of Glu in extracellular spaces is determined by the aggregate contributions of synthesis and release offset by metabolism and uptake back into neurons and glia by glutamate.

Deficient functioning of glutamate transporters has been implicated in a variety of neurological diseases. Thus, for example studies have shown that deficient functioning of glutamate transporters (GTs) in Alzheimer disease (AD) can lead to neurodegeneration. Similarly, recent evidence in rat limbic system indicates that seizure activity can selectively downregulate the expression of glutamate transport in the hippocampus. Evidence in human epileptic temporal lobe indicates that defective glutamate transport can play a critical role in the death of neurons in the human epileptic hippocampus. (Sutherland et al. (2001) Activity-dependent decrease in glutamate transporter mRNA expression: a mechanism for excitotoxic cell death following seizures. *Soc. Neurosci. Abstr.* In press; Yoshor et al. (2001) *Selective loss of EAAT2, a glial glutamate transporter, in CA1 and CA4 hippocampal subfields in Ammon's Horn Sclerosis. Epilepsia,* In press; Sutherland et al. (1995) *J. Neurosci.*, 16: 2191–2207; Sutherland et al. (1995) *Gene,* 27: 131–141; Tanaka et al. (1997) *Science,* 276: 1).

Without being bound by a particular theory, it is believed that the release of too much glutamate causes excessive excitation in the nervous system that leads to seizures, contributes to injury after stroke, the perception of pain and even the destruction of nerve cells associated with neurodegenerative diseases, including Alzheimer's disease, Parkinson's disease and amyotrophic lateral sclerosis (Lou Gehrig's disease).

An agent that inhibits a VGLUT glutamate transporter will prevent the transporter from loading glutamate, thus reducing the release of glutamate, in these, and other conditions, and presumably could be used to treat these illnesses.

In addition, inhibition of glutamate transport has been shown to enhance the therapeutic efficacy of doxirubicin (Sadzuka and Sonobe (2001) *Toxicol. Lett.,* 121(2): 89–96) and it is expected that specific glutamate transporter inhibition can be advantageous in a course of chemotherapy, particularly in the treatment of various brain tumors.

Inhibition of glutamate can also be useful in anesthesia and the management of pain (e.g. neuropathic pain).

Conversely, it is expected that, in certain conditions, selective increase in glutamate transport (e.g. by upregulating glutamate transporter expression) can depress extracellular glutamate levels and thereby reduce and/or eliminate the neurodegenerative effects of inhibited glutamate transport in these and other pathologies.

In addition, increasing the amount of glutamate released from certain nerve cells could improve learning, memory skills and overall cognitive function. In this case, therapy might simply involve taking a drug that increases the expression of the gene that produces the protein transporter. The resulting increased expression of the protein would enable nerve cells to store and release more glutamate.

Conversely, in certain circumstances, inhibition of glutamate transporters has been shown to have beneficial effects. Thus, for example, Inhibition of glutamate can also be useful in anesthesia.

In view of this modulators (e.g. upregulators and downregulators) of glutamate transporter expression or activity are of great interest. In certain embodiments, the glutamate transporters of this invention provide good targets to screen for modulators of glutamate transporter expression and/or activity and it is expected that such modulators provide good lead compounds for pharmaceutical development.

Moreover, it is demonstrated herein, that the various glutamate transporters of this invention are present on different neuronal subpopulations. Identification of agents that modulate glutamate transport by one transporter (e.g. VGLUT1) as compared to another (e.g. VGLUT2) will provide therapeutic lead compounds of unprecedented specificity.

In addition, having identified the VGLUT glutamate transporters it is possible to produce knockout animals heterozygous or homozygous for a knocked-out VGLUT1, and/or VGLUT2, and/or VGLUT3. Such animals provide good model systems in which to investigate the effects of glutamate transporter inhibition.

I. Assays for Modulators of VGLUT Expression and/or Activity

As indicated above, in one aspect, this invention is premised, in part, on the discovery of new class of glutamate transporters (VGLUT). It is believed that activity these transporters are critical for healthy neurological activity and upregulation of such receptors can mitigate adverse effects of a variety of neuropathologies (e.g. ALS, epilepsy, Parkinsons disease, Alzheimer's disease, etc.). Conversely, inhibition of the VGLUT transporters can have beneficial effects in certain circumstances.

Thus, in certain embodiments, this invention provides methods of screening for agents that modulate expression and/or activity of VGLUT transporters (e.g. VGLUT1, VGLUT2, VGLUT3). In certain embodiments, the methods involve contacting a cell comprising a VGLUT transporter nucleic acid (e.g. VGLUT1, VGLUT2, VGLUT3 nucleic acids) with a test agent; and detecting the expression or activity of the VGLUT transporter(s) wherein a difference in the expression of the VGLUT transporter(s) of the cell as compared to the activity the VGLUT transporter(s) of a control cell (e.g. a cell of the same type that is contacted with a lower concentration of test agent or no test agent) indicates that the test agent alters VGLUT transporter expression and/or activity.

Detection of changes in metabolic activity can involve detecting the expression level and/or activity level of VGLUT genes or gene products or VGLUT polypeptides or polypeptide activity.

In certain instances, it is desired to identify agents that specifically modulate particular subsets of VGLUT glutamate transporters. Thus in certain embodiments, test agents are screened for a differential effect on expression and/or activity of VGLUT1 and/or VGLUT2, and/or VGLUT3. Thus, for example, agents are screened and selected where they show different effects on VGLUT1 as compared to VGLUT2 and/or VGLUT3, or on VGLUT2 as compared to VGLUT1 and/or VGLUT3, or on VGLUT3 as compared to VGLUT1 and/or VGLUT2. Such differential effects can include, but are not limited to no effect on one transporter (e.g. VGLUT1) and a significant effect on VGLUT2 and/or VGLUT3, a significant effect on VGLUT1 and no significant effect on VGLUT2 and/or VGLUT3, upregulation of VGLUT1 and downregulation of VGLUT2 and/or VGLUT3, downregulation of VGLUT1 and upregulation of VGLUT2 and/or VGLUT3, and the like.

Expression levels of a gene can be altered by changes in the transcription of the gene product (i.e. transcription of mRNA), and/or by changes in translation of the gene product (i.e. translation of the protein), and/or by post-translational modification(s) (e.g. protein folding, glycosylation, etc.). Thus preferred assays of this invention include assaying for level of transcribed niRNA (or other nucleic acids derived from the subject genes), level of translated protein, activity of translated protein, etc. Examples of such approaches are described below.

A) Nucleic-acid Based Assays

1) Target Molecules.

Changes in expression level can be detected by measuring changes in genomic DNA or a nucleic acid derived from the genomic DNA (e.g. VGLUT). In order to measure the expression level it is desirable to provide a nucleic acid sample for such analysis. In preferred embodiments the nucleic acid is found in or derived from a biological sample. The term "biological sample", as used herein, refers to a sample obtained from an organism or from components (e.g., cells) of an organism. The sample may be of any biological tissue or fluid. Biological samples may also include organs or sections of tissues such as frozen sections taken for histological purposes. Biological samples also include cells in culture and the cells can be native cells or recombinantly modified cells (e.g. modified to express a heterologous VGLUT transporter).

The nucleic acid (e.g., VGLUT mRNA or a nucleic acid derived from a VGLUT mRNA) is, in certain preferred embodiments, isolated from the sample according to any of a number of methods well known to those of skill in the art. Methods of isolating mRNA are well known to those of skill in the art. For example, methods of isolation and purification of nucleic acids are described in detail in by Tijssen ed., (1993) Chapter 3 of *Laboratory Techniques in Biochemistry and Molecular Biology: Hybridization With Nucleic Acid Probes, Part I. Theory and Nucleic Acid Preparation*, Elsevier, N.Y. and Tijssen ed.

In a preferred embodiment, the "total" nucleic acid is isolated from a given sample using, for example, an acid guanidinium-phenol-chloroform extraction method and polyA+mRNA is isolated by oligo dT column chromatography or by using (dT)n magnetic beads (see, e.g., Sambrook et al., *Molecular Cloning: A Laboratory Manual* (2nd ed.), Vols. 1–3, Cold Spring Harbor Laboratory, (1989), or *Current Protocols in Molecular Biology*, F. Ausubel et al., ed. (1987) Greene Publishing and Wiley-Interscience, New York).

Frequently, it is desirable to amplify the nucleic acid sample prior to assaying for expression level. Methods of amplifying nucleic acids are well known to those of skill in the art and include, but are not limited to polymerase chain reaction (PCR, see. e.g., Innis, et al., (1990) *PCR Protocols. A guide to Methods and Application*. Academic Press, Inc. San Diego,), ligase chain reaction (LCR) (see Wu and Wallace (1989) *Genomics* 4: 560, Landegren et al. (1988) *Science* 241: 1077, and Barringer et al. (1990) *Gene* 89: 117, transcription amplification (Kwoh et al. (1989) *Proc. Natl. Acad. Sci. USA* 86: 1173), self-sustained sequence replication (Guatelli et al. (1990) *Proc. Nat. Acad. Sci. USA* 87: 1874), dot PCR, and linker adapter PCR, etc.).

In a particularly preferred embodiment, where it is desired to quantify the transcription level (and thereby expression) (e.g. of a VGLUT transporter such as VGLUT1, VGLUT2, and/or VGLUT3) in a sample, the nucleic acid sample is one in which the concentration of the VGLUT mRNA transcript (s), or the concentration of the nucleic acids derived from the mRNA transcript(s), is proportional to the transcription level (and therefore expression level) of that gene. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear. Thus, for example, an assay where a 5 fold difference in concentration of the target mRNA results in a 3 to 6 fold difference in hybridization intensity is sufficient for most purposes.

Where more precise quantification is required appropriate controls can be run to correct for variations introduced in sample preparation and hybridization as described herein. In addition, serial dilutions of "standard" target nucleic acids (e.g., mRNAs) can be used to prepare calibration curves according to methods well known to those of skill in the art. Of course, where simple detection of the presence or absence of a transcript or large differences of changes in nucleic acid concentration is desired, no elaborate control or calibration is required.

In the simplest embodiment, the sample nucleic acid sample is the total mRNA or a total cDNA isolated and/or otherwise derived from a biological sample. The nucleic acid may be isolated from the sample according to any of a number of methods well known to those of skill in the art as indicated above.

2) Hybridization-based Assays.

The expression of particular genes (e.g. VGLUT genes such as VGLUT1, VGLUT2, and VGLUT3)) can be routinely detected and/or quantitated using nucleic acid hybridization techniques (see, e.g., Sambrook et al. supra). For example, one method for evaluating the presence, absence, or quantity of a particular genomic DNA or reverse-transcribed cDNA involves a "Southern Blot". In a Southern Blot, the DNA sample is typically fragmented and separated on an electrophoretic gel and hybridized to a probe specific for the nucleic acid(s) of interest. Comparison of the intensity of the hybridization signal from the probe with a "control" probe (e.g. a probe for a "housekeeping gene) provides an estimate of the relative expression level of the target nucleic acid (e.g. a VGLUT nucleic acid).

Alternatively, the VGLUT mRNA can be directly quantified in a Northern blot. In brief, the mRNA is isolated from a given cell sample using, for example, an acid guanidinium-phenol-chloroform extraction method. The mRNA is then electrophoresed to separate the mRNA species and the mRNA is then transferred from the gel to a membrane (e.g. a nitrocellulose membrane). As with the Southern blots, labeled probes are used to identify and/or quantify the target (VGLUT) mRNA. Appropriate controls (e.g. probes to housekeeping genes) provide a reference for evaluating relative VGLUT expression level.

An alternative means for determining the particular nucleic acid expression levels is in situ hybridization. In situ hybridization assays are well known (e.g., Angerer (1987) *Meth. Enzymol* 152: 649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application.

In some applications it is necessary to block the hybridization capacity of repetitive sequences. Thus, in some embodiments, tRNA, human genomic DNA, or Cot-1 DNA is used to block non-specific hybridization.

3) Amplification-based Assays.

In another embodiment, amplification-based assays can be used to measure expression (transcription) level of particular genes (e.g. VGLUT genes such as VGLUT1, VGLUT2, VGLUT3, etc.). In such amplification-based assays, the target nucleic acid sequences act as template(s) in amplification reaction(s) (e.g. Polymerase Chain Reaction (PCR) or reverse-transcription PCR (RT-PCR)). In a quantitative amplification, the amount of amplification product will be proportional to the amount of template in the original sample. Comparison to appropriate controls (e.g. tissue or cells exposed to the test agent at a different concentration or not exposed to the test agent) provides a measure of the target transcript level.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis et al. (1990) *PCR Protocols, A Guide to Methods and Applications*, Academic Press, Inc. N.Y.). One approach, for example, involves simultaneously co-amplifying a known quantity of a control sequence using the same primers as those used to amplify the target. This provides an internal standard that may be used to calibrate the PCR reaction.

4) Hybridization Formats and Optimization of Hybridization Conditions a) Array-based Hybridization Formats.

In one embodiment, the methods of this invention can be utilized in array-based hybridization formats. Arrays are a multiplicity of different "probe" or "target" nucleic acids (or other compounds) attached to one or more surfaces (e.g., solid, membrane, or gel). In a preferred embodiment, the multiplicity of nucleic acids (or other moieties) is attached to a single contiguous surface or to a multiplicity of surfaces juxtaposed to each other.

In an array format a large number of different hybridization reactions can be run essentially "in parallel." This provides rapid, essentially simultaneous, evaluation of a number of hybridizations in a single "experiment". Methods of performing hybridization reactions in array-based formats are well known to those of skill in the art (see, e.g., Pastinen (1997) *Genome Res.* 7: 606–614; Jackson (1996) *Nature Biotechnology* 14:1685; Chee (1995) *Science* 274: 610; WO 96/17958, Pinkel et al. (1998) *Nature Genetics* 20: 207–211).

Arrays, particularly nucleic acid arrays can be produced according to a wide variety of methods well known to those of skill in the art. For example, in a simple embodiment, "low density" arrays can simply be produced by spotting (e.g. by hand using a pipette) different nucleic acids at different locations on a solid support (e.g. a glass surface, a membrane, etc.).

This simple spotting, approach has been automated to produce high density spotted arrays (see, e.g., U.S. Pat. No. 5,807,522). This patent describes the use of an automated system that taps a microcapillary against a surface to deposit a small volume of a biological sample. The process is repeated to generate high-density arrays.

Arrays can also be produced using oligonucleotide synthesis technology. Thus, for example, U.S. Pat. No. 5,143,854 and PCT Patent Publication Nos. WO 90/15070 and 92/10092 teach the use of light-directed combinatorial synthesis of high density oligonucleotide arrays. Synthesis of high density arrays is also described in U.S. Pat. Nos. 5,744,305, 5,800,992 and 5,445,934.

b) Other Hybridization Formats.

A wide variety of nucleic acid hybridization formats are known to those skilled in the art. For example, common formats include sandwich assays and competition or displacement assays. Such assay formats are generally described in Hames and Higgins (1985) *Nucleic Acid Hybridization, A Practical Approach*, IRL Press; Gall and Pardue (1969) *Proc. Natl. Acad. Sci. USA* 63: 378–383; and John et al. (1969) *Nature* 223: 582–587.

Sandwich assays are commercially useful hybridization assays for detecting or isolating nucleic acid sequences. Such assays utilize a "capture" nucleic acid covalently immobilized to a solid support and a labeled "signal" nucleic acid in solution. The sample will provide the target nucleic acid. The "capture" nucleic acid and "signal" nucleic acid probe hybridize with the target nucleic acid to form a "sandwich" hybridization complex. To be most effective, the signal nucleic acid should not hybridize with the capture nucleic acid.

Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^3$H, $^{125}$I, $^{35}$S, $^{14}$C, or $^{32}$P-labelled probes or the like. Other labels include ligands that bind to labeled antibodies, fluorophores, chemiluminescent agents, enzymes, and antibodies which can serve as specific binding pair members for a labeled ligand.

Detection of a hybridization complex may involve the binding of a signal generating complex to a duplex of target and probe polynucleotides or nucleic acids. Typically, such binding occurs through ligand and anti-ligand interactions as between a ligand-conjugated probe and an anti-ligand conjugated with a signal.

The sensitivity of the hybridization assays may be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBAO, Cangene, Mississauga, Ontario) and Q Beta Replicase systems.

c) Optimization of Hybridization Conditions.

Nucleic acid hybridization simply involves providing a denatured probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids, or in the addition of chemical agents, or the raising of the pH. Under low stringency conditions (e.g., low temperature and/or high salt and/or high target concentration) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency to ensure hybridization and then subsequent washes are performed at higher stringency to eliminate mismatched hybrid duplexes. Successive washes may be performed at increasingly higher stringency (e.g., down to as low as 0.25× SSPE at 37° C. to 70° C.) until a desired level of hybridization specificity is obtained. Stringency can also be increased by addition of agents such as formamide. Hybridization specificity may be evaluated by comparison of hybridization to the test probes with hybridization to the various controls that can be present.

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular probes of interest.

In a preferred embodiment, background signal is reduced by the use of a blocking reagent (e.g., tRNA, sperm DNA, cot-1 DNA, etc.) during the hybridization to reduce non-specific binding. The use of blocking agents in hybridization is well known to those of skill in the art (see, e.g., Chapter 8 in P. Tijssen, supra.).

Methods of optimizing hybridization conditions are well known to those of skill in the art (see, e.g., Tijssen (1993) *Laboratory Techniques in Biochemistry and Molecular Biology, Vol. 24: Hybridization With Nucleic Acid Probes*, Elsevier, N.Y.).

Optimal conditions are also a function of the sensitivity of label (e.g., fluorescence) detection for different combinations of substrate type, fluorochrome, excitation and emission bands, spot size and the like. Low fluorescence background surfaces can be used (see, e.g., Chu (1992) *Electrophoresis* 13:105–114). The sensitivity for detection of spots ("target elements") of various diameters on the candidate surfaces can be readily determined by, e.g., spotting a dilution series of fluorescently end labeled DNA fragments. These spots are then imaged using conventional fluorescence microscopy. The sensitivity, linearity, and dynamic range achievable from the various combinations of fluorochrome and solid surfaces (e.g., glass, fused silica, etc.) can thus be determined. Serial dilutions of pairs of fluorochrome in known relative proportions can also be analyzed. This determines the accuracy with which fluorescence ratio measurements reflect actual fluorochrome ratios over the dynamic range permitted by the detectors and fluorescence of the substrate upon which the probe has been fixed.

d) Labeling and Detection of Nucleic Acids.

The probes used herein for detection of VGLUT expression levels can be full length or less than the full length of the VGLUT (e.g. VGLUT1, VGLUT2, or VGLUT3) mRNA. Shorter probes are empirically tested for specificity. Preferred probes are sufficiently long so as to specifically hybridize with the VGLUT target nucleic acid(s) under stringent conditions. The preferred size range is from about 20 bases to the length of the VGLUT mRNA, more preferably from about 30 bases to the length of the VGLUT mRNA, and most preferably from about 40 bases to the length of the VGLUT mRNA.

The probes are typically labeled, with a detectable label. Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like, see, e.g., Molecular Probes, Eugene, Oreg., USA), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold (e.g., gold particles in the 40–80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

A fluorescent label is preferred because it provides a very strong signal with low background. It is also optically detectable at high resolution and sensitivity through a quick scanning procedure. The nucleic acid samples can all be labeled with a single label, e.g., a single fluorescent label. Alternatively, in another embodiment, different nucleic acid samples can be simultaneously hybridized where each nucleic acid sample has a different label. For instance, one target could have a green fluorescent label and a second target could have a red fluorescent label. The scanning step will distinguish sites of binding of the red label from those binding the green fluorescent label. Each nucleic acid sample (target nucleic acid) can be analyzed independently from one another.

Suitable chromogens which can be employed include those molecules and compounds which absorb light in a distinctive range of wavelengths so that a color can be observed or, alternatively, that emit light when irradiated with radiation of a particular wave length or wave length range, e.g., fluorescent molecules.

Desirably, fluorescent labels should absorb light above about 300 nm, preferably about 350 nm, and more preferably above about 400 nm, usually emitting at wavelengths greater than about 10 nm higher than the wavelength of the light absorbed.

Detectable signal can also be provided by chemiluminescent and bioluminescent sources. Chemiluminescent sources include compounds that become electronically excited by a chemical reaction and can then emit light that serves as the detectable signal or donates energy to a fluorescent acceptor. Alternatively, luciferins can be used in conjunction with luciferase or lucigenins to provide bioluminescence.

Spin labels are provided by reporter molecules with an unpaired electron spin which can be detected by electron spin resonance (ESR) spectroscopy. Exemplary spin labels include organic free radicals, transitional metal complexes, particularly vanadium, copper, iron, and manganese, and the like. Exemplary spin labels include nitroxide free radicals.

The label can be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see *Laboratory Techniques in Biochemistry and Molecular Biology, Vol. 24: Hybridization With Nucleic Acid Probes*, P. Tijssen, ed. Elsevier, N.Y., (1993)).

Fluorescent labels are easily added during an in vitro transcription reaction. Thus, for example, fluorescein labeled UTP and CTP can be incorporated into the RNA produced in an in vitro transcription.

The labels can be attached directly or through a linker moiety. In general, the site of label or linker-label attachment is not limited to any specific position. For example, a label may be attached to a nucleoside, nucleotide, or analogue thereof at any position that does not interfere with detection or hybridization as desired. For example, certain Label-On Reagents from Clontech (Palo Alto, Calif.) provide for labeling interspersed throughout the phosphate backbone of an oligonucleotide and for terminal labeling at the 3' and 5' ends. As shown for example herein, labels can be attached at positions on the ribose ring or the ribose can be modified and even eliminated as desired. The base moieties of useful labeling reagents can include those that are naturally occurring or modified in a manner that does not interfere with the purpose to which they are put. Modified bases include but are not limited to 7-deaza A and G, 7-deaza-8-aza A and G, and other heterocyclic moieties.

It will be recognized that fluorescent labels are not to be limited to single species of organic molecules, but include inorganic molecules, multi-molecular mixtures of organic and/or inorganic molecules, crystals, heteropolymers, and the like. Thus, for example, CdSe-CdS core-shell nanocrystals enclosed in a silica shell can be easily derivatized for coupling to a biological molecule (Bruchez et al. (1998) *Science*, 281: 2013–2016). Similarly, highly fluorescent quantum dots (zinc sulfide-capped cadmium selenide) have been covalently coupled to biomolecules for use in ultrasensitive biological detection (Warren and Nie (1998) *Science*, 281: 2016–2018).

B) VGLUT Polypeptide-based Assays—Polypeptide Expression

1) Assay Formats.

In addition to, or in alternative to, the detection of nucleic acid expression level(s), alterations in expression of VGLUT transporters can be detected and/or quantified by detecting and/or quantifying the amount and/or activity of translated VGLUT polypeptide or fragments thereof.

2) Detection of expressed protein.

The VGLUT polypeptides to be assayed can be detected and quantified by any of a number of methods well known to those of skill in the art. These include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting, and the like.

In one preferred embodiment, the VGLUT polypeptide(s) are detected/quantified in an electrophoretic protein separation (e.g. a 1- or 2-dimensional electrophoresis). Means of detecting proteins using electrophoretic techniques are well known to those of skill in the art (see generally, R. Scopes (1982) *Protein Purfication*, Springer-Verlag, N.Y.; Deutscher, (1990) *Methods in Enzymology Vol. 182: Guide to Protein Purification*, Academic Press, Inc., N.Y.).

In another preferred embodiment, Western blot (immunoblot) analysis is used to detect and quantify the presence of polypeptide(s) of this invention in the sample. This technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the target polypeptide(s).

The antibodies specifically bind to the target VGLUT polypeptide(s) and can be directly labeled or alternatively may be subsequently detected using labeled antibodies (e.g., labeled sheep anti-mouse antibodies) that specifically bind to the a domain of the antibody.

In preferred embodiments, the VGLUT polypeptide(s) (e.g. VGLUT1, VGLUT2 and VGLUT3 polypeptides) are detected using an immunoassay. As used herein, an immunoassay is an assay that utilizes an antibody to specifically bind to the analyte (e.g., the target polypeptide(s)). The immunoassay is thus characterized by detection of specific binding of a polypeptide of this invention to an antibody as opposed to the use of other physical or chemical properties to isolate, target, and quantify the analyte.

Any of a number of well recognized immunological binding assays (see, e.g., U.S. Pat. Nos. 4,366,241; 4,376, 110; 4,517,288; and 4,837,168) are well suited to detection or quantification of the polypeptide(s) identified herein. For a review of the general immunoassays, see also Asai (1993) *Methods in Cell Biology Volume* 37: *Antibodies in Cell Biology*, Academic Press, Inc. New York; Stites & Terr (1991) *Basic and Clinical Immunology 7th Edition.*

Immunological binding assays (or immunoassays) typically utilize a "capture agent" to specifically bind to and often immobilize the analyte. In preferred embodiments, the capture agent is an antibody.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled polypeptide or a labeled antibody that specifically recognizes the already bound target polypeptide. Alternatively, the labeling agent may be a third moiety, such as another antibody, that specifically binds to the capture agent/polypeptide complex.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see, generally Kronval, et al. (1973) *J. Immunol.*, 111: 1401–1406, and Akerstrom (1985) *J. Immunol.*, 135: 2589–2542).

Preferred immunoassays for detecting the target polypeptide(s) are either competitive or noncompetitive. Noncompetitive immunoassays are assays in which the amount of captured analyte is directly measured. In one preferred "sandwich" assay, for example, the capture agents (antibodies) can be bound directly to a solid substrate where they are immobilized. These immobilized antibodies then capture the target polypeptide present in the test sample. The target polypeptide thus immobilized is then bound by a labeling agent, such as a second antibody bearing a label.

In competitive assays, the amount of analyte (e.g. VGLUT transporter) present in the sample is measured indirectly by measuring the amount of an added (exogenous) analyte displaced (or competed away) from a capture agent (antibody) by the analyte present in the sample. For example, in one competitive assay, a known amount of, labeled VGLUT transporter polypeptide is added to the sample and the sample is then contacted with a capture agent. The amount of labeled polypeptide bound to the antibody is inversely proportional to the concentration of target polypeptide present in the sample.

In one particularly preferred embodiment, the antibody is immobilized on a solid substrate. The amount of target polypeptide bound to the antibody may be determined either by measuring the amount of target polypeptide present in a polypeptide/antibody complex, or alternatively by measuring the amount of remaining uncomplexed polypeptide.

The immunoassay methods of the present invention include an enzyme immunoassay (EIA) which utilizes, depending on the particular protocol employed, unlabeled or labeled (e.g., enzyme-labeled) derivatives of polyclonal or monoclonal antibodies or antibody fragments or single-chain antibodies. In certain embodiments the antibodies are antibodies that bind to a VGLUT transporter polypeptide. Any of the known modifications of EIA, for example, enzyme-linked immunoabsorbent assay (ELISA), may also be employed. As indicated above, also contemplated by the present invention are immunoblotting immunoassay techniques such as western blotting employing an enzymatic detection system.

The immunoassay methods of the present invention may also include other known immunoassay methods, for example, fluorescent immunoassays using antibody conjugates or antigen conjugates of fluorescent substances such as fluorescein or rhodamine, latex agglutination with antibody-coated or antigen-coated latex particles, haemagglutination with antibody-coated or antigen-coated red blood corpuscles, and immunoassays employing an avidin-biotin or streptavidin-biotin detection systems, and the like.

The particular parameters employed in the immunoassays of the present invention can vary widely depending on various factors such as the concentration of antigen in the sample, the nature of the sample, the type of immunoassay employed and the like. Optimal conditions can be readily established by those of ordinary skill in the art. In certain embodiments, the amount of antibody that binds the VGLUT transporter polypeptide is typically selected to give 50% binding of detectable marker in the absence of sample. If purified antibody is used as the antibody source, the amount of antibody used per assay will generally range from about 1 ng to about 100 ng. Typical assay conditions include a temperature range of about 4° C. to about 45° C., preferably about 25° C. to about 37° C., and most preferably about 25° C., a pH value range of about 5 to 9, preferably about 7, and an ionic strength varying from that of distilled water to that of about 0.2M sodium chloride, preferably about that of 0.15M sodium chloride. Times will vary widely depending upon the nature of the assay, and generally range from about 0.1 minute to about 24 hours. A wide variety of buffers, for example PBS, may be employed, and other reagents such as salt to enhance ionic strength, proteins such as serum albumins, stabilizers, biocides and nonionic detergents may also be included.

The assays of this invention are scored (as positive or negative or quantity of target VGLUT polypeptide) according to standard methods well known to those of skill in the art. The particular method of scoring will depend on the assay format and choice of label. For example, a Western Blot assay can be scored by visualizing the colored product produced by the enzymatic label. A clearly visible colored band or spot at the correct molecular weight is scored as a positive result, while the absence of a clearly visible spot or band is scored as a negative. The intensity of the band or spot can provide a quantitative measure of target polypeptide concentration.

Antibodies for use in the various immunoassays described herein, are commercially available or can be produced as described below.

3) Antibodies to VGLUT Transporter Polypeptides.

Either polyclonal or monoclonal antibodies (e.g., anti-VGLUT transporter antibodies) can be used in the immunoassays of the invention described herein. Polyclonal antibodies are preferably raised by multiple injections (e.g. subcutaneous or intramuscular injections) of substantially pure polypeptides (e.g. VGLUT1, and/or VGLUT2, and/or VGLUT3 or fragments thereof) into a suitable non-human mammal. The antigenicity of the target peptides can be determined by conventional techniques to determine the magnitude of the antibody response of an animal that has been immunized with the peptide. Generally, the peptides that are used to raise antibodies for use in the methods of this invention should generally be those that induce production of high titers of antibody with relatively high affinity for target polypeptide.

If desired, the immunizing VGLUT peptide can be coupled to a carrier protein, e.g., by conjugation using techniques that are well-known in the art. Commonly used carriers that can be chemically coupled to the peptide include keyhole limpet hemocyanin (KLH), thyroglobulin, bovine serum albumin (BSA), tetanus toxoid, and the like. The coupled peptide is used to immunize the animal (e.g. a mouse or a rabbit).

The antibodies are then obtained from blood samples taken from the mammal. The techniques used to develop polyclonal antibodies are known in the art (see, e.g., *Methods of Enzymology*, "Production of Antisera With Small Doses of Immunogen: Multiple Intradermal Injections", Langone, et al. eds. (Acad. Press, 1981)). Polyclonal antibodies produced by the animals can be further purified, for example, by binding to and elution from a matrix to which the peptide to which the antibodies were raised is bound. Those of skill in the art will know of various techniques common in the immunology arts for purification and/or concentration of polyclonal antibodies, as well as monoclonal antibodies see, for example, Coligan, et al. (1991) Unit 9, *Current Protocols in Immunology*, Wiley Interscience).

Preferably, however, the anti-VGLUT antibodies produced are monoclonal antibodies ("mAb's"). For preparation of monoclonal antibodies, immunization of a mouse or rat is preferred. The term "antibody" as used in this invention includes intact molecules as well as fragments thereof, such as, Fab and F(ab')$_2$, and/or single-chain antibodies (e.g. scFv) that are capable of binding an epitopic determinant.

The general method used for production of hybridomas secreting mAbs is well known (Kohler and Milstein (1975) *Nature*, 256:495). Briefly, as described by Kohler and Milstein the technique comprises fusing an antibody-secreting cell (e.g. a splenocyte) with an immortalized cell (e.g. a myeloma cell). Hybridomas are then screened for production of antibodies that bind to a VGLUT polypeptide or a fragment thereof. Confirmation of specificity among mAb's can be accomplished using relatively routine screening techniques (such as the enzyme-linked immunosorbent assay, or "ELISA", BiaCore, etc.) to determine the binding specificity and/or avidity of the mAb of interest.

Antibodies fragments, e.g. single chain antibodies (scFv or others), can also be produced/selected using phage display technology. The ability to express antibody fragments on the surface of viruses that infect bacteria (bacteriophage or phage) makes it possible to isolate a single binding antibody fragment, e.g., from a library of greater than $10^{10}$ nonbinding clones. To express antibody fragments on the surface of phage (phage display), an antibody fragment gene is inserted into the gene encoding a phage surface protein (e.g., pIII) and the antibody fragment-pIII fusion protein is displayed on the phage surface (McCafferty et al. (1990) *Nature*, 348: 552–554; Hoogenboom et al. (1991) *Nucleic Acids Res*. 19: 4133–4137).

Since the antibody fragments on the surface of the phage are functional, phage bearing antigen binding antibody fragments can be separated from non-binding phage by antigen affinity chromatography (McCafferty et al. (1990) Nature, 348: 552–554). Depending on the affinity of the antibody fragment, enrichment factors of 20 fold 1,000,000 fold are obtained for a single round of affinity selection. By infecting bacteria with the eluted phage, however, more phage can be grown and subjected to another round of selection. In this way, an enrichment of 1000 fold in one round can become 1,000,000 fold in two rounds of selection (McCafferty et al. (1990) Nature, 348: 552–554). Thus even when enrichments are low (Marks et al. (1991) J. Mol. Biol. 222: 581–597), multiple rounds of affinity selection can lead to the isolation of rare phage. Since selection of the phage antibody library on antigen results in enrichment, the majority of clones bind antigen after as few as three to four rounds of selection. Thus only a relatively small number of clones (several hundred) need to be analyzed for binding to antigen.

Human antibodies can be produced without prior immunization by displaying very large and diverse V-gene repertoires on phage (Marks et al. (1991) J. Mol. Biol. 222: 581–597). In one embodiment natural $V_H$ and $V_L$ repertoires present in human peripheral blood lymphocytes are were isolated from unimmunized donors by PCR. The V-gene repertoires were spliced together at random using PCR to create a scFv gene repertoire which is was cloned into a phage vector to create a library of 30 million phage antibodies (ld.). From this single "naive" phage antibody library, binding antibody fragments have been isolated against more than 17 different antigens, including haptens, polysaccharides and proteins (Marks et al. (1991) J. Mol. Biol. 222: 581–597; Marks et al. (1993). Bio/Technology. 10: 779–783; Griffiths et al. (1993) EMBO J. 12: 725–734; Clackson et al. (1991) Nature. 352: 624–628). Antibodies have been produced against self proteins, including human thyroglobulin, immunoglobulin, tumor necrosis factor and CEA (Griffiths et al. (1993) EMBO J. 12: 725–734). It is also possible to isolate antibodies against cell surface antigens by selecting directly on intact cells. The antibody fragments are highly specific for the antigen used for selection and have affinities in the 1:M to 100 nM range (Marks et al. (1991) J. Mol. Biol. 222: 581–597; Griffiths et al. (1993) EMBO J. 12: 725–734). Larger phage antibody libraries result in the isolation of more antibodies of higher binding affinity to a greater proportion of antigens.

It will also be recognized that antibodies can be prepared by any of a number of commercial services (e.g., Berkeley antibody laboratories, Bethyl Laboratories, Anawa, Eurogenetec, etc.).

C) Polypeptide-based Assays—Polypeptide Activity

In addition to, or as an alternative to, the assays described above, it is also possible to assay for glutamate transporter activity. As explained above, the VGLUT family polypeptides are glutamate transporters. Thus, VGLUT activity in a cell can be readily measured by providing a suitable ligand (e.g. labeled glutamate) and measuring the VGLUT transporter-mediated uptake of the ligand.

Having identified VGLUT polypeptides as glutamate transporters, methods of transfecting cells with a nucleic acid that encodes a functional VGLUT transporter, can be routinely accomplished. Preferred cells are cells that do not normally express the VGLUT transporter whose activity is to be assayed. Such cells include, but are not limited to oocytes (e.g. Xenopus laevis oocytes).

One such activity assay is illustrated herein in Example 2. In this example, the ability of VGLUT2 (DNPI) to transport glutamate into secretory vesicles was assayed using heterologous expressed VGLUT2 in rat pheochromocytoma PC12 cells, that exhibit no endogenous VGLUT2 (DNPI) mRNA or immunoreactivity.

A series of transfected clones stably expressing DNPI was derived, a population of light membranes including synaptic-like microvesicles was prepared, and assayed their ability to accumulate $^3$H-glutamate.

Assays for activity of other VGLUT polypeptides can be similarly accomplished.

D) Pre-Screening for Agents that Bind VGLUT Nucleic Acids or Polypeptides

In certain embodiments it is desired to pre-screen test agents for the ability to interact with (e.g. specifically bind to) a VGLUT nucleic acid or polypeptide. Specifically, binding test agents are more likely to interact with and thereby modulate VGLUT transporter expression and/or activity. Thus, in some preferred embodiments, the test agent(s) are pre-screened for binding VGLUT nucleic acids or to VGLUT transporters before performing the more complex assays described above.

In one embodiment, such pre-screening is accomplished with simple binding assays. Means of assaying for specific binding or the binding affinity of a particular ligand for a nucleic acid or for a protein are well known to those of skill in the art. In preferred binding assays, the VGLUT transporter protein or protein fragment, or nucleic acid is immobilized and exposed to a test agent (which can be labeled), or alternatively, the test agent(s) are immobilized and exposed to a VGLUT polypeptide (or fragment) or to a VGLUT nucleic acid or fragment thereof (which can be labeled). The immobilized moiety is then washed to remove any unbound material and the bound test agent or bound VGLUT nucleic acid or protein is detected (e.g. by detection of a label attached to the bound molecule). The amount of immobilized label is proportional to the degree of binding between the VGLUT protein or nucleic acid and the test agent.

II. Modulator Databases

In certain embodiments, the agents that score positively in the assays described herein (e.g. show an ability to modulate VGLUT transporter expression or activity) can be entered into a database of putative and/or actual modulators of glutamate transport. The term database refers to a means for recording and retrieving information. In preferred embodiments the database also provides means for sorting and/or searching the stored information. The database can comprise any convenient media including, but not limited to, paper systems, card systems, mechanical systems, electronic systems, optical systems, magnetic systems or combinations thereof. Preferred databases include electronic (e.g. computer-based) databases. Computer systems for use in storage and manipulation of databases are well known to those of skill in the art and include, but are not limited to "personal computer systems", mainframe systems, distributed nodes on an inter- or intra-net, data or databases stored in specialized hardware (e.g. in microchips), and the like.

III. High throughput Screening for Agents that Modulate VGLUT Expression and/or Activity The assays for modulators of VGLUT expression and/or activity or VGLUT ligands are also amenable to "high-throughput" modalities. Conventionally, new chemical entities with useful properties (e.g., modulation of VGLUT transporter activity and/or expression) are generated by identifying a chemical compound (called a "lead compound") with some desirable property or activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of compounds (candidate compounds) potentially having the desired activity. Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used directly in the desired application.

A) Combinatorial Chemical Libraries for Modulators of VGLUT Expression or Activity The likelihood of an assay identifying an agent that modulates VGLUT transporter activity and/or expression is increased when the number and types of test agents used in the screening system is increased. Recently, attention has focused on the use of combinatorial chemical libraries to assist in the generation of new chemical compound leads. A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al. (1994) 37(9): 1233–1250).

Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) Int. J. Pept. Prot. Res., 37: 487–493, Houghton et al. (1991) Nature, 354: 84–88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, Dec. 26, 1991), encoded peptides (PCT Publication WO 93/20242, Oct. 14, 1993), random bio-oligomers (PCT Publication WO 92/00091, Jan. 9, 1992), benzodiazepines (U.S. Pat. No. 5,288,514), diversomers such as hydantoins, benzodiazepines and dipeptides (Hobbs et al., (1993) Proc. Nat. Acad. Sci. USA 90: 6909–6913), vinylogous polypeptides (Hagihara et al. (1992) J. Amer. Chem. Soc. 114: 6568), nonpeptidal peptidomimetics with a Beta-D-Glucose scaffolding (Hirschmann et al., (1992) J. Amer. Chem. Soc. 114: 9217–9218), analogous organic syntheses of small compound libraries (Chen et al. (1994) J. Amer. Chem. Soc. 116: 2661), oligocarbamates (Cho, et al., (1993) Science 261:1303), and/or peptidyl phosphonates (Campbell et al., (1994) J. Org. Chem. 59: 658). See, generally, Gordon et al., (1994) J. Med. Chem. 37:1385, nucleic acid libraries (see, e.g., Strategene, Corp.), peptide nucleic acid libraries (see, e.g., U.S. Pat. No. 5,539,083) antibody libraries (see, e.g., Vaughn et al. (1996) Nature Biotechnology, 14(3): 309–314), and PCT/US96/10287), carbohydrate libraries (see, e.g., Liang et al. (1996) Science, 274: 1520–1522, and U.S. Pat. No. 5,593,853), and small organic molecule libraries (see, e.g., benzodiazepines, Baum (1993) C&EN, Jan 18, page 33, isoprenoids U.S. Pat. No. 5,569,588, thiazolidinones and metathiazanones U.S. Pat. No. 5,549,974, pyrrolidines U.S. Pat. Nos. 5,525,735 and 5,519,134, morpholino compounds U.S. Pat. No. 5,506,337, benzodiazepines 5,288, 514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

B) High throughput Assays of Chemical Libraries for Modulators of VGLUT Transporter Expression and/or Activity Any of the assays for agents that modulate VGLUT transporter expression or activity are amenable to high throughput screening. As described above likely modulators either inhibit expression of the gene product, or inhibit the activity of the receptor. Preferred assays thus detect inhibition of transcription (i.e., inhibition of mRNA production) by the test compound(s), inhibition of protein expression by the test compound(s), binding to the gene (e.g., gDNA, or cDNA) or gene product (e.g., mRNA or expressed protein) by the test compound(s). High throughput assays for the presence, absence, or quantification of particular nucleic acids or protein products are well known to those of skill in the art. Similarly, binding assays are similarly well known. Thus, for example, U.S. Pat. No. 5,559,410 discloses high throughput screening methods for proteins, U.S. Pat. No. 5,585,639 discloses high throughput screening methods for nucleic acid binding (i.e., in arrays), while U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

IV. Providing Cells that Transport Lutamate

Certain embodiments of this invention provide cells that are modified to alter their glutamate transporter activity. Such cells can include cells that have no endogenous glutamate transporter activity, cells that have normally comprise glutamate transporters other than VGLUT transporters and/or cells that normally express VGLUT transporters (e.g. VGLUT1, and/or VGLUT2, and/or VGLUT3).

In certain embodiments the cells are convenient for assaying for glutamate transporter activity. In other embodiments, the cells are modified to increase VGLUT transporter activity to treat or mitigate a pathological state. Thus, for example, where a subject (e.g. human or non-human mammal) suffers from an affliction associated with depressed glutamate transporter activity (e.g. ALS, Alzheimers disease, Parkinson's disease, etc.), cells in the organism can be transfected with a nucleic acid expressing a one or more heterologous VGLUT transporter(s) thereby increasing the ability of the cell to transport glutamate (e.g. into synaptic vesicles).

Methods of transiently or stably expressing heterologous nucleic acids in cells are well known to those of skill in the art. Using the sequence information provided herein and in publicly available databases, DNA encoding the VGLUT proteins described herein can be prepared by any suitable method as described above, including, for example, cloning and restriction of appropriate sequences or direct chemical synthesis by methods such as the phosphotriester method of Narang et al. (1979) *Meth. Enzymol.* 68–90–99; the phosphodiester method of Brown et al.(1979) *Meth. Enzymol.* 68: 109–151; the diethylphosphoramidite method of Beaucage et al. (1981) *Tetra. Lett.*, 22: 1859–1862; and the solid support method of U.S. Pat. No. 4,458,066.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Alternatively, subsequences may be cloned and the appropriate subsequences cleaved using appropriate restriction enzymes. The fragments may then be ligated to produce the desired DNA sequence.

In one embodiment, the VGLUT nucleic acids of this invention can be cloned using DNA amplification methods such as polymerase chain reaction (PCR) (see, e.g., Example 2). Thus, for example, the nucleic acid sequence or subsequence is PCR amplified, using a sense primer containing one restriction site (e.g., NdeI) and an antisense primer containing another restriction site (e.g., HindIII). This will produce a nucleic acid encoding the desired VGLUT sequence or subsequence and having terminal restriction sites. This nucleic acid can then be easily ligated into a vector containing a nucleic acid encoding the second molecule and having the appropriate corresponding restriction sites. Suitable PCR primers can be determined by one of skill in the art using the sequence information provided herein. Appropriate restriction sites can also be added to the nucleic acid encoding the VGLUT protein or protein subsequence by site-directed mutagenesis. The plasmid containing the VGLUT sequence or subsequence is cleaved with the appropriate restriction endonuclease and then ligated into the vector encoding the second molecule according to standard methods.

The nucleic acid sequences encoding VGLUT proteins or protein subsequences may be expressed in a variety of host cells, including *E. coli*, other bacterial hosts, yeast, and various higher eukaryotic cells such as the COS, CHO and HeLa cells lines and myeloma cell lines. In preferred embodiments, the VGLUT proteins are expressed in mammalian cells, e.g. rat pheochromocytoma PC12 cells. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and often an enhancer (e.g., an enhancer derived from immunoglobulin genes, SV40, cytomegalovirus, etc.), and a polyadenylation sequence, and may include splice donor and acceptor sequences.

The plasmids of the invention can be transferred into the chosen host cell by well-known methods such as calcium chloride transformation for *E. coli* and calcium phosphate treatment or electroporation for mammalian cells. In certain embodiments, cells are transfected in vivo using vectors commonly used in gene therapy applications.

One of skill would recognize that modifications can be made to the VGLUT proteins without diminishing their biological activity. Some modifications can be made to facilitate the cloning, expression, or incorporation of the targeting molecule into a fusion protein. Such modifications are well known to those of skill in the art and include, for example, a methionine added at the amino terminus to provide an initiation site, altered codon usage to facilitate expression, and the like.

As indicated above, nucleic acids encoding a heterologous VGLUT glutamate transporter can be delivered in vivo to supplement cells in which such glutamate transport is deficient. Thus, in certain preferred embodiments, the nucleic acids encoding VGLUT glutamate transporters are cloned into gene therapy vectors that are competent to transfect cells (such as human or other mammalian cells) in vitro and/or in vivo.

Many approaches for introducing nucleic acids into cells in vivo, ex vivo and in vitro are known. These include lipid or liposome based gene delivery (WO 96/18372; WO 93/24640; Mannino and Gould-Fogerite (1988) *BioTechniques* 6(7): 682–691; Rose U.S. Pat No. 5,279,833; WO 91/06309; and Felgner et al. (1987) *Proc. Natl. Acad. Sci. USA* 84: 7413–7414) and replication-defective retroviral vectors harboring a therapeutic polynucleotide sequence as part of the retroviral genome (see, e.g., Miller et al. (1990) *Mol. Cell. Biol.* 10:4239 (1990); Kolberg (1992) *J. NIH Res.* 4: 43, and Cometta et al. (1991) *Hum. Gene Ther.* 2: 215). "Gene therapy" procedures are discussed in greater detail below.

V. Altering VGLUT Expression/Activity

In certain embodiments, this invention provides methods of inhibiting glutamate transport (e.g. uptake into synaptic vesicles) by a cell. Such methods preferably involve inhibiting expression or activity of a VGLUT glutamate transporter (e.g. VGLUT1, VGLUT2, VGLUT3, etc.). In other embodimens, VGLUT expression or activity is upregulated (e.g. by transfecting cells with a construct that expresses a heterologous VGLUT glutamate transporter, by altering the VGLUT promoter, and the like).

VGLUT expression can upregulated or inhibited using a wide variety of approaches known to those of skill in the art. For example, methods of inhibiting VGLUT expression include, but are not limited to antisense molecules, VGLUT specific ribozymes, VGLUT specific catalytic DNAs, intrabodies directed against VGLUT proteins, RNAi, gene therapy approaches that knock out VGLUTs, and small organic molecules that inhibit VGLUT expression/overexpression or block receptor that is required to induce VGLUT expression. VGLUT expression and/or activity can be up-regulated by introducing constructs expressing VGLUT into the cell (e.g. using gene therapy approaches) or upregulating endogenous expression of VGLUT (e.g. using agents identified in the screening assays of this invention). It will be appreciated that the methods used to alter VGLUT expression/activity can generally also be used to alter expression/activity of VGLUT homologues.

A) Antisense Approaches

VGLUT (e.g. VGLUT1, and/or VGLUT2, and/or VGLUT3) gene expression can be downregulated or entirely inhibited by the use of antisense molecules. An "antisense sequence or antisense nucleic acid" is a nucleic acid that is complementary to the coding VGLUT mRNA nucleic acid sequence or a subsequence thereof. Binding of the antisense molecule to the VGLUT mRNA interferes with normal translation of the VGLUT polypeptide.

Thus, in accordance with preferred embodiments of this invention, preferred antisense molecules include oligonucleotides and oligonucleotide analogs that are hybridizable with VGLUT messenger RNA. This relationship is commonly denominated as "antisense." The oligonucleotides and oligonucleotide analogs are able to inhibit the function of the RNA, either its translation into protein, its translocation into the cytoplasm, or any other activity necessary to its overall biological function. The failure of the messenger RNA to perform all or part of its function results in a reduction or complete inhibition of expression of VGLUT polypeptides.

In the context of this invention, the term "oligonucleotide" refers to a polynucleotide formed from naturally-occurring bases and/or cyclofuranosyl groups joined by native phosphodiester bonds. This term effectively refers to naturally-occurring species or synthetic species formed from naturally-occurring subunits or their close homologs. The term "oligonucleotide" may also refer to moieties which function similarly to oligonucleotides, but which have non naturally-occurring portions. Thus, oligonucleotides may have altered sugar moieties or inter-sugar linkages. Exemplary among these are the phosphorothioate and other sulfur containing species that are known for use in the art. In accordance with some preferred embodiments, at least one of the phosphodiester bonds of the oligonucleotide has been substituted with a structure which functions to enhance the ability of the compositions to penetrate into the region of cells where the RNA whose activity is to be modulated is located. It is preferred that such substitutions comprise phosphorothioate bonds, methyl phosphonate bonds, or short chain alkyl or cycloalkyl structures. In accordance with other preferred embodiments, the phosphodiester bonds are substituted with structures which are, at once, substantially non-ionic and non-chiral, or with structures which are chiral and enantiomerically specific. Persons of ordinary skill in the art will be able to select other linkages for use in the practice of the invention.

In one particularly preferred embodiment, the internucleotide phosphodiester linkage is replaced with a peptide linkage. Such peptide nucleic acids tend to show improved stability, penetrate the cell more easily, and show enhances affinity for their target. Methods of making peptide nucleic acids are known to those of skill in the art (see, e.g., U.S. Pat. Nos. 6,015,887, 6,015,710, 5,986,053, 5,977,296, 5,902,786, 5,864,010, 5,786,461, 5,773,571, 5,766,855, 5,736,336, 5,719,262, and 5,714,331).

Oligonucleotides may also include species that contain at least some modified base forms. Thus, purines and pyrimidines other than those normally found in nature may be so employed. Similarly, modifications on the furanosyl portions of the nucleotide subunits may also be effected, as long as the essential tenets of this invention are adhered to. Examples of such modifications are 2'-O-alkyl- and 2'-halogen-substituted nucleotides. Some specific examples of modifications at the 2' position of sugar moieties which are useful in the present invention are OH, SH, $SCH_3$, F, $OCH_3$, OCN, $O(CH_2)[n]NH_2$ or $O(CH_2)[n]CH_3$, where n is from 1 to about 10, and other substituents having similar properties.

Such oligonucleotides are best described as being functionally interchangeable with natural oligonucleotides or synthesized oligonucleotides along natural lines, but which have one or more differences from natural structure. All such analogs are comprehended by this invention so long as they function effectively to hybridize with messenger RNA of VGLUT to inhibit the function of that RNA.

The oligonucleotides in accordance with this invention preferably comprise from about 3 to about 50 subunits. It is more preferred that such oligonucleotides and analogs comprise from about 8 to about 25 subunits and still more preferred to have from about 12 to about 20 subunits. As will be appreciated, a subunit is a base and sugar combination suitably bound to adjacent subunits through phosphodiester or other bonds. The oligonucleotides used in accordance with this invention may be conveniently and routinely made through the well-known technique of solid phase synthesis. Equipment for such synthesis is sold by several vendors, including Applied Biosystems. Any other means for such synthesis may also be employed, however, the actual synthesis of the oligonucleotides is well within the talents of the routineer. It is also will known to prepare other oligonucleotide such as phosphorothioates and alkylated derivatives.

Using the known sequence of the VGLUT gene(s)/cDNA(s) identified herein, appropriate and effective antisense oligonucleotide sequences can be readily determined.

B) Catalytic RNAs and DNAs

1) Ribozymes.

In another approach, VGLUT expression can be inhibited by the use of ribozymes. As used herein, "ribozymes" are include RNA molecules that contain anti-sense sequences for specific recognition, and an RNA-cleaving enzymatic activity. The catalytic strand cleaves a specific site in a target (VGLUT) RNA, preferably at greater than stoichiometric concentration. Two "types" of ribozymes are particularly useful in this invention, the hammerhead ribozyme (Rossi et al. (1991) *Pharmac. Ther.* 50: 245–254) and the hairpin ribozyme (Hampel et al. (1990) *Nucl. Acids Res.* 18: 299–304, and U.S. Pat. No. 5,254,678).

Because both hammerhead and hairpin ribozymes are catalytic molecules having antisense and endoribonucleotidase activity, ribozyme technology has emerged as a powerful extension of the antisense approach to gene inactivation. The ribozymes of the invention typically consist of RNA, but such ribozymes may also be composed of nucleic acid molecules comprising chimeric nucleic acid sequences (such as DNA/RNA sequences) and/or nucleic acid analogs (e.g., phosphorothioates).

Accordingly, within one aspect of the present invention ribozymes are provided which have the ability to inhibit VGLUT expression. Such ribozymes can be in the form of a "hammerhead" (for example, as described by Forster and Symons (1987) *Cell* 48: 211–220,; Haseloff and Gerlach (1988) *Nature* 328: 596–600; Walbot and Bruening (1988)

*Nature* 334: 196; Haseloff and Gerlach (1988) *Nature* 334: 585) or a "hairpin" (see, e.g. U.S. Pat. No. 5,254,678 and Hampel et al., European Patent Publication No. 0 360 257, published Mar. 26, 1990), and have the ability to specifically target, cleave and VGLUT nucleic acids.

The sequence requirement for the hairpin ribozyme is any RNA sequence consisting of NNNBN*GUCNNNNNN (where N*G is the cleavage site, where B is any of G, C, or U, and where N is any of Q, U, C, or A) (SEQ ID NO:9). Suitable VGLUT of recognition or target sequences for hairpin ribozymes can be readily determined from the VGLUT sequence(s) identified herein.

The preferred sequence at the cleavage site for the hammerhead ribozyme is any RNA sequence consisting of NUX (where N is any of G, U, C, or A and X represents C, U, or A) can be targeted. Accordingly, the same target within the hairpin leader sequence, GUC, is useful for the hammerhead ribozyme. The additional nucleotides of the hammerhead ribozyme or hairpin ribozyme is determined by the target flanking nucleotides and the hammerhead consensus sequence (see Ruffner et al. (1990) *Biochemistry* 29: 10695–10702).

Cech et al. (U.S. Pat. No. 4,987,071,) has disclosed the preparation and use of certain synthetic ribozymes which have endoribonuclease activity. These ribozymes are based on the properties of the Tetrahymena ribosomal RNA self-splicing reaction and require an eight base pair target site. A temperature optimum of 50° C. is reported for the endoribonuclease activity. The fragments that arise from cleavage contain 5' phosphate and 3' hydroxyl groups and a free guanosine nucleotide added to the 5' end of the cleaved RNA. The preferred ribozymes of this invention hybridize efficiently to target sequences at physiological temperatures, making them particularly well suited for use in vivo.

The ribozymes of this invention, as well as DNA encoding such ribozymes and other suitable nucleic acid molecules can be chemically synthesized using methods well known in the art for the synthesis of nucleic acid molecules. Alternatively, Promega, Madison, Wis., USA, provides a series of protocols suitable for the production of RNA molecules such as ribozymes. The ribozymes also can be prepared from a DNA molecule or other nucleic acid molecule (which, upon transcription, yields an RNA molecule) operably linked to an RNA polymerase promoter, e.g., the promoter for T7 RNA polymerase or SP6 RNA polymerase. Such a construct may be referred to as a vector. Accordingly, also provided by this invention are nucleic acid molecules, e.g., DNA or cDNA, coding for the ribozymes of this invention. When the vector also contains an RNA polymerase promoter operably linked to the DNA molecule, the ribozyme can be produced in vitro upon incubation with the RNA polymerase and appropriate nucleotides. In a separate embodiment, the DNA may be inserted into an expression cassette (see, e.g., Cotten and Bimstiel (1989) *EMBO J* 8(12):3861–3866; Hempel et al. (1989) *Biochem.* 28: 4929–4933, etc.).

After synthesis, the ribozyme can be modified by ligation to a DNA molecule having the ability to stabilize the ribozyme and make it resistant to RNase. Alternatively, the ribozyme can be modified to the phosphothio analog for use in liposome delivery systems. This modification also renders the ribozyme resistant to endonuclease activity.

The ribozyme molecule also can be in a host prokaryotic or eukaryotic cell in culture or in the cells of an organism/patient. Appropriate prokaryotic and eukaryotic cells can be transfected with an appropriate transfer vector containing the DNA molecule encoding a ribozyme of this invention.

Alternatively, the ribozyme molecule, including nucleic acid molecules encoding the ribozyme, may be introduced into the host cell using traditional methods such as transformation using calcium phosphate precipitation (Dubensky et al. (1984) *Proc. Natl. Acad. Sci., USA*, 81: 7529–7533), direct microinjection of such nucleic acid molecules into intact target cells (Acsadi et al. (1991) *Nature* 352: 815818), and electroporation whereby cells suspended in a conducting solution are subjected to an intense electric field in order to transiently polarize the membrane, allowing entry of the nucleic acid molecules. Other procedures include the use of nucleic acid molecules linked to an inactive adenovirus (Cotton et al. (1990) *Proc. Natl. Acad. Sci., USA*, 89 :6094), lipofection (Felgner et al. (1989) *Proc. Natl. Acad. Sci. USA* 84: 7413–7417), microprojectile bombardment (Williams et al. (1991) *Proc. Natl. Acad. Sci., USA*, 88: 2726–2730), polycation compounds such as polylysine, receptor specific ligands, liposomes entrapping the nucleic acid molecules, spheroplast fusion whereby *E coli* containing the nucleic acid molecules are stripped of their outer cell walls and fused to animal cells using polyethylene glycol, viral transduction, (Cline et al., (1985) *Pharmac. Ther.* 29: 69; and Friedmann et al. (1989) *Science* 244: 1275), and DNA ligand (Wu et al (1989) *J. Biol. Chem.* 264: 16985–16987), as well as psoralen inactivated viruses such as Sendai or Adenovirus. In one preferred embodiment, the ribozyme is introduced into the host cell utilizing a lipid, a liposome or a retroviral vector.

When the DNA molecule is operatively linked to a promoter for RNA transcription, the RNA can be produced in the host cell when the host cell is grown under suitable conditions favoring transcription of the DNA molecule. The vector can be, but is not limited to, a plasmid, a virus, a retrotransposon or a cosmid. Examples of such vectors are disclosed in U.S. Pat. No. 5,166,320. Other representative vectors include, but are not limited to adenoviral vectors (e.g., WO 94/26914, WO 93/9191; Kolls et al. (1994) PNAS 91(1):215–219; Kass-Eisler et al., (1993) *Proc. Natl. Acad. Sci., USA*, 90(24): 11498–502, Guzman et al. (1993) *Circulation* 88(6): 2838–48, 1993; Guzman et al. (1993) *Cir. Res.* 73(6): 1202–1207, 1993; Zabner et al. (1993) *Cell* 75(2): 207–216; Li et al. (1993) *Hum Gene Ther.* 4(4): 403–409; Caillaud et al. (1993) *Eur. J Neurosci.* 5(10): 1287–1291), adeno-associated vector type 1 ("AAV-1") or adeno-associated vector type 2 ("AAV-2") (see WO 95/13365; Flotte et al. (1993) *Proc. Natl. Acad. Sci., USA*, 90(22) :10613–10617), retroviral vectors (e.g., EP 0 415 731; WO 90/07936; WO 91/02805; WO 94/03622; WO 93/25698; WO 93/25234; U.S. Pat. No. 5,219,740; WO 93/11230; WO 93/10218) and herpes viral vectors (e.g., U.S. Pat. No. 5,288,641). Methods of utilizing such vectors in gene therapy are well known in the art, see, for example, Larrick and Burck (1991) *Gene Therapy: Application of Molecular Biology*, Elsevier Science Publishing Co., Inc., New York, N.Y., and Kreigler (1990) *Gene Transfer and Expression: A Laboratory Manual*, W. H. Freeman and Company, New York.

To produce ribozymes in vivo utilizing vectors, the nucleotide sequences coding for ribozymes are preferably placed under the control of a strong promoter such as the lac, SV40 late, SV40 early, or lambda promoters. Ribozymes are then produced directly from the transfer vector in vivo. Suitable transfector vectors for in vivo expression are discussed below.

2) Catalytic DNA

In a manner analogous to ribozymes, DNAs are also capable of demonstrating catalytic (e.g. nuclease) activity.

While no such naturally-occurring DNAs are known, highly catalytic species have been developed by directed evolution and selection. Beginning with a population of $10^{14}$ DNAs containing 50 random nucleotides, successive rounds of selective amplification, enriched for individuals that best promote the $Pb^{2+}$-dependent cleavage of a target ribonucleoside 3'—O—P bond embedded within an otherwise all-DNA sequence. By the fifth round, the population as a whole carried out this reaction at a rate of 0.2 $min^{-1}$. Based on the sequence of 20 individuals isolated from this population, a simplified version of the catalytic domain that operates in an intermolecular context with a turnover rate of 1 $min^{-1}$ (see, e.g., Breaker and Joyce (1994) *Chem Biol* 4: 223–229.

In later work, using a similar strategy, a DNA enzyme was made that could cleave almost any targeted RNA substrate under simulated physiological conditions. The enzyme is comprised of a catalytic domain of 15 deoxynucleotides, flanked by two substrate-recognition domains of seven to eight deoxynucleotides each. The RNA substrate is bound through Watson-Crick base pairing and is cleaved at a particular phosphodiester located between an unpaired purine and a paired pyrimidine residue. Despite its small size, the DNA enzyme has a catalytic efficiency (kcat/Km) of approximately $10^9$ $M^{-1}$ $min^{-1}$ under multiple turnover conditions, exceeding that of any other known nucleic acid enzyme. By changing the sequence of the substrate-recognition domains, the DNA enzyme can be made to target different RNA substrates (Santoro and Joyce (1997) *Proc. Natl. Acad. Sci., USA*, 94(9): 4262–4266). Modifying the appropriate targeting sequences (e.g. as described by Santoro and Joyce, supra.) the DNA enzyme can easily be retargeted to VGLUT mRNA thereby acting like a ribozyme.

C) Knocking Out VGLUT

In another approach, VGLUT can be inhibited/downregulated simply by "knocking out" the gene.

D) VGLUT Knockout Animals.

In certain embodiments, this invention provides animals in which VGLUT glutamate transporter are "knocked out". Such animals can be heterozygous or homozygous for the knockout.

Typically this is accomplished by disrupting the VGLUT gene(s), the promoter regulating the VGLUT gene(s) or sequences between the endogenous promoter(s) and the gene(s). Such disruption can be specifically directed to VGLUT nucleic acids (e.g. VGLUT1, and/or VGLUT2, and/or VGLUT3) by homologous recombination where a "knockout construct" contains flanking sequences complementary to the domain to which the construct is targeted. Insertion of the knockout construct (e.g. into a VGLUT gene) results in disruption of that gene.

The phrases "disruption of the gene" and "gene disruption" refer to insertion of a nucleic acid sequence into one region of the native DNA sequence (usually one or more exons) and/or the promoter region of a gene so as to decrease or prevent expression of that gene in the cell as compared to the wild-type or naturally occurring sequence of the gene. By way of example, a nucleic acid construct can be prepared containing a DNA sequence encoding an antibiotic resistance gene which is inserted into the DNA sequence that is complementary to the DNA sequence (promoter and/or coding region) to be disrupted. When this nucleic acid construct is then transfected into a cell, the construct will integrate into the genomic DNA. Thus, the cell and its progeny will no longer express the gene or will express it at a decreased level, as the DNA is now disrupted by the antibiotic resistance gene.

Knockout constructs can be produced by standard methods known to those of skill in the art. The knockout construct can be chemically synthesized or assembled, e.g., using recombinant DNA methods. The DNA sequence to be used in producing the knockout construct is digested with a particular restriction enzyme selected to cut at a location(s) such that a new DNA sequence encoding a marker gene can be inserted in the proper position within this DNA sequence. The proper position for marker gene insertion is that which will serve to prevent expression of the native VGLUT gene; this position will depend on various factors such as the restriction sites in the sequence to be cut, and whether an exon sequence or a promoter sequence, or both is (are) to be interrupted (i.e., the precise location of insertion necessary to inhibit promoter function or to inhibit synthesis of the native exon). Preferably, the enzyme selected for cutting the DNA will generate a longer arm and a shorter arm, where the shorter arm is at least about 300 base pairs (bp). In some cases, it will be desirable to actually remove a portion or even all of one or more exons of the gene to be suppressed so as to keep the length of the knockout construct comparable to the original genomic sequence when the marker gene is inserted in the knockout construct. In these cases, the genomic DNA is cut with appropriate restriction endonucleases such that a fragment of the proper size can be removed.

The marker gene can be any nucleic acid sequence that is detectable and/or assayable, however typically it is an antibiotic resistance gene or other gene whose expression or presence in the genome can easily be detected. The marker gene is usually operably linked to its own promoter or to another strong promoter from any source that will be active or can easily be activated in the cell into which it is inserted; however, the marker gene need not have its own promoter attached as it may be transcribed using the promoter of the gene to be suppressed. In addition, the marker gene will normally have a polyA sequence attached to the 3' end of the gene; this sequence serves to terminate transcription of the gene. Preferred marker genes are any antibiotic resistance gene including, but not limited to neo (the neomycin resistance gene) and beta-gal (beta-galactosidase).

After the genomic DNA sequence has been digested with the appropriate restriction enzymes, the marker gene sequence is ligated into the genomic DNA sequence using methods well known to the skilled artisan (see, e.g., Berger and Kimmel, *Guide to Molecular Cloning Techniques, Methods in Enzymology* volume 152 Academic Press, Inc., San Diego, Calif.; Sambrook et al. (1989) *Molecular Cloning—A Laboratory Manual* (2nd ed.) Vol. 1–3, Cold Spring Harbor Laboratory, Cold Spring Harbor Press, NY; and *Current Protocols in Molecular Biology*, F. M. Ausubel et al., eds., Current Protocols, a joint venture between Greene Publishing Associates, Inc. and John Wiley & Sons, Inc., (1994) Supplement). The ends of the DNA fragments to be ligated are rendered compatible, e.g., by either cutting the fragments with enzymes that generate compatible ends, or by blunting the ends prior to ligation. Blunting is done using methods well known in the art, such as for example by the use of Klenow fragment (DNA polymerase I) to fill in sticky ends.

The production of knockout constructs and their use to produce knockout mice is well known to those of skill in the art (see, e.g., Dorfman et al. (1996) *Oncogene* 13: 925–931). The knockout constructs can be delivered to cells in vivo using gene therapy delivery vehicles (e.g. retroviruses, liposomes, lipids, dendrimers, etc.) as described above. Methods of knocking out genes are well described in the literature and essentially routine to those of skill in the art (see, e.g., Thomas et al. (1986) *Cell* 44(3): 419–428;

Thomas, et al. (1987) *Cell* 51(3): 503–512)1; Jasin and Berg (1988) *Genes & Development* 2: 1353–1363; Mansour, et al. (1988) *Nature* 336: 348–352; Brinster, et al. (1989) *Proc Natl Acad Sci* 86: 7087–7091; Capecchi (1989) *Trends in Genetics* 5(3): 70–76; Frohman and Martin (1989) *Cell* 56: 145–147; Hasty, et al. (1991) *Mol Cell Bio* 11(11): 5586–5591; Jeannotte, et al. (1991) *Mol Cell Biol*. 11(11): 5578–5585; and Mortensen, et al. (1992) *Mol Cell Biol*. 12(5): 2391–2395.

The use of homologous recombination to alter expression of endogenous genes is also described in detail in U.S. Pat. No. 5,272,071, WO 91/09955, WO 93/09222, WO 96/29411, WO 95/31560, and WO 91/12650.

Production of the knockout animals of this invention is not dependent on the availability of ES cells. In various embodiments, knockout animals of this invention can be produced using methods of somatic cell nuclear transfer. In preferred embodiments using such an approach, a somatic cell is obtained from the species in which the VGLUT gene is to be knocked out. The cell is transfected with a construct that introduces a disruption in the VGLUT gene (e.g. via heterologous recombination) as described herein. Cells harboring a knocked out VGLUT gene are selected as described herein. The nucleus of such cells harboring the knockout is then placed in an unfertilized enucleated egg (e.g., eggs from which the natural nuclei have been removed by microsurgery). Once the transfer is complete, the recipient eggs contained a complete set of genes, just as they would if they had been fertilized by sperm. The eggs are then cultured for a period before being implanted into a host mammal (of the same species that provided the egg) where they are carried to term, culminating in the berth of a transgenic animal comprising a nucleic acid construct containing one or more disrupted VGLUT genes.

The production of viable cloned mammals following nuclear transfer of cultured somatic cells has been reported for a wide variety of species including, but not limited to frogs (McKinnell (1962) *J. Hered*. 53, 199–207), calves (Kato et al. (1998) *Science* 262: 2095–2098), sheep (Campbell et al. (1996) *Nature* 380: 64–66), mice (Wakayamaand Yanagimachi (1999) *Nat. Genet*. 22: 127–128), goats (Baguisi et al. (1999) *Nat. Biotechnol*. 17: 456–461), monkeys (Meng et al. (1997) *Biol. Reprod*. 57: 454–459), and pigs (Bishop et al. (2000) *Nature Biotechnology* 18: 1055–1059). Nuclear transfer methods have also been used to produce clones of transgenic animals. Thus, for example, the production of transgenic goats carrying the human antithrobin III gene by somatic cell nuclear transfer has been reported (Baguisi et al. (1999) *Nature Biotechnology* 17: 456461).

Using methods of nuclear transfer as described in these and other references, cell nuclei derived from differentiated fetal or adult, mammalian cells are transplanted into enucleated mammalian oocytes of the same species as the donor nuclei. The nuclei are reprogrammed to direct the development of cloned embryos, which can then be transferred into recipient females to produce fetuses and offspring, or used to produce cultured inner cell mass (CICM) cells. The cloned embryos can also be combined with fertilized embryos to produce chimeric embryos, fetuses and/or offspring.

Somatic cell nuclear transfer also allows simplification of transgenic procedures by working with a differentiated cell source that can be clonally propagated. This eliminates the need to maintain the cells in an undifferentiated state, thus, genetic modifications, both random integration and gene targeting, are more easily accomplished. Also by combining nuclear transfer with the ability to modify and select for these cells in vitro, this procedure is more efficient than previous transgenic embryo techniques.

Nuclear transfer techniques or nuclear transplantation techniques are known in the literature. See, in particular, Campbell et al. (1995) *Theriogenology*, 43:181; Collas et al. (1994) *Mol. Report Dev*., 38:264–267; Keefer et al. (1994) *Biol. Reprod*., 50:935–939; Sims et al. (1993) *Proc. Natl. Acad. Sci., USA*, 90:6143–6147; WO 94/26884; WO 94/24274, WO 90/03432, U.S. Pat. Nos. 5,945,577, 4,944, 384, 5,057,420 and the like.

E) Intrabodies

In still another embodiment, VGLUT expression/activity is inhibited by transfecting the subject cell(s) (e.g., cells of the vascular endothelium) with a nucleic acid construct that expresses an intrabody. An intrabody is an intracellular antibody, in this case, capable of recognizing and binding to a VGLUT polypeptide. The intrabody is expressed by an "antibody cassette", containing a sufficient number of nucleotides coding for the portion of an antibody capable of binding to the target (VGLUT polypeptide) operably linked to a promoter that will permit expression of the antibody in the cell(s) of interest. The construct encoding the intrabody is delivered to the cell where the antibody is expressed intracellularly and binds to the target VGLUT, thereby disrupting the target from its normal action. This antibody is sometimes referred to as an "intrabody".

In one preferred embodiment, the "intrabody gene" (antibody) of the antibody cassette would utilize a cDNA, encoding heavy chain variable ($V_H$) and light chain variable ($V_L$) domains of an antibody which can be connected at the DNA level by an appropriate oligonucleotide as a bridge of the two variable domains, which on translation, form a single peptide (referred to as a single chain variable fragment, "sFv") capable of binding to a target such as an VGLUT protein. The intrabody gene preferably does not encode an operable secretory sequence and thus the expressed antibody remains within the cell.

Anti-VGLUT antibodies suitable for use/expression as intrabodies in the methods of this invention can be readily produced by a variety of methods. Such methods include, but are not limited to, traditional methods of raising "whole" polyclonal antibodies, which can be modified to form single chain antibodies, or screening of, e.g. phage display libraries to select for antibodies showing high specificity and/or avidity for VGLUT. Such screening methods are described above in some detail.

The antibody cassette is delivered to the cell by any of the known means. This discloses the use of a fusion protein comprising a target moiety and a binding moiety. The target moiety brings the vector to the cell, while the binding moiety carries the antibody cassette. Other methods include, for example, Miller (1992) *Nature* 357: 455–460; Anderson (1992) *Science* 256: 808–813; Wu, et al. (1988) *J. Biol. Chem*. 263: 14621–14624. For example, a cassette containing these (anti-VGLUT) antibody genes, such as the sFv gene, can be targeted to a particular cell by a number of techniques including, but not limited to the use of tissue-specific promoters, the use of tissue specific vectors, and the like. Methods of making and using intrabodies are described in detail in U.S. Pat. No. 6,004,940.

E) Small Organic Molecules

In still another embodiment, VGLUT expression and/or VGLUT protein activity can be inhibited by the use of small organic molecules. Such molecules include, but are not limited to molecules that specifically bind to the DNA comprising the VGLUT promoter and/or coding region, molecules that bind to and complex with VGLUT mRNA, molecules that inhibit the signaling pathway that results in VGLUT upregulation, and molecules that bind to and/or compete with VGLUT polypeptides. Small organic molecules effective at inhibiting VGLUT expression can be identified with routine screening using the methods described herein.

The methods of inhibiting VGLUT expression described above are meant to be illustrative and not limiting. In view of the teachings provided herein, other methods of inhibiting VGLUT will be known to those of skill in the art.

F) Modes of Administration

The mode of administration of the VGLUT blocking agent depends on the nature of the particular agent. Antisense molecules, catalytic RNAs (ribozymes), catalytic DNAs, small organic molecules, and other molecules (e.g. lipids, antibodies, etc.) used as VGLUT inhibitors may be formulated as pharmaceuticals (e.g. with suitable excipient) and delivered using standard pharmaceutical formulation and delivery methods as described below. Antisense molecules, catalytic RNAs (ribozymes), catalytic DNAs, and additionally, knockout constructs, and constructs encoding intrabodies can be delivered and (if necessary) expressed in target cells (e.g. vascular endothelial cells) using methods of gene therapy, e.g. as described below.

1) Pharmaceutical Administration.

In order to carry out the methods of the invention, one or more inhibitors of VGLUT expression (e.g. ribozymes, antibodies, antisense molecules, small organic molecules, etc.) are administered to an individual to ameliorate one or more symptoms of a neurological dysfunction (e.g. Alzheimers, ALS, stroke, epilepsy, etc.). While this invention is described generally with reference to human subjects, veterinary applications are contemplated within the scope of this invention.

Various inhibitors may be administered, if desired, in the form of salts, esters, amides, prodrugs, derivatives, and the like, provided the salt, ester, amide, prodrug or derivative is suitable pharmacologically, i.e., effective in the present method. Salts, esters, amides, prodrugs and other derivatives of the active agents may be prepared using standard procedures known to those skilled in the art of synthetic organic chemistry and described, for example, by March (1992) *Advanced Organic Chemistry; Reactions, Mechanisms and Structure*, 4th Ed. N.Y. Wiley-Interscience.

The VGLUT inhibitors and various derivatives and/or formulations thereof are useful for parenteral, topical, oral, or local administration, such as by aerosol or transdermally, for prophylactic and/or therapeutic treatment of coronary disease and/or rheumatoid arthritis. The pharmaceutical compositions can be administered in a variety of unit dosage forms depending upon the method of administration. Suitable unit dosage forms, include, but are not limited to powders, tablets, pills, capsules, lozenges, suppositories, etc.

The VGLUT inhibitors and various derivatives and/or formulations thereof are typically combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the active agents, or excipients or other stabilizers and/or buffers.

Other physiologically acceptable compounds include wetting agents, emulsifying agents, dispersing agents or preservatives which are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s). The excipients are preferably sterile and generally free of undesirable matter. These compositions may be sterilized by conventional, well known sterilization techniques.

The concentration of active agent(s) in the formulation can vary widely, and will be selected primarily based on fluid volumes, viscosities, body weight and the like in accordance with the particular mode of administration selected and the patient's needs.

In therapeutic applications, the compositions of this invention are administered to a patient suffering from a disease (e.g., atherosclerosis and/or associated conditions, and/or rheumatoid arthritis) in an amount sufficient to cure or at least partially arrest the disease and/or its symptoms (e.g. to reduce plaque formation, to reduce monocyte recruitment, etc.) An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the active agents of the formulations of this invention to effectively treat (ameliorate one or more symptoms) the patient.

In certain preferred embodiments, the VGLUT inhibitors are administered orally (e.g. via a tablet) or as an injectable in accordance with standard methods well known to those of skill in the art. In other preferred embodiments, the VGLUT inhibitors may also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient (s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

The foregoing formulations and administration methods are intended to be illustrative and not limiting. It will be appreciated that, using the teaching provided herein, other suitable formulations and modes of administration can be readily devised.

2) Gene Therapy.

As indicated above, molecules encoding and expressing heterologous VGLUT transporters, antisense molecules, catalytic RNAs (ribozymes), catalytic DNAs, and additionally, knockout constructs, and constructs encoding intrabodies can be delivered and transcribed and/or expressed in target cells (e.g. cancer cells) using methods of gene therapy. Thus, in certain preferred embodiments, the nucleic acids encoding knockout constructs, intrabodies, antisense molecules, catalytic RNAs or DNAs, etc. are cloned into gene therapy vectors that are competent to transfect cells (such as human or other mammalian cells) in vitro and/or in vivo.

Many approaches for introducing nucleic acids into cells in vivo, ex vivo and in vitro are known. These include lipid or liposome based gene delivery (WO 96/18372; WO 93/24640; Mannino and Gould-Fogerite (1988) *BioTechniques* 6(7): 682–691; Rose U.S. Pat No. 5,279,833; WO 91/06309; and Felgner et al. (1987) *Proc. Natl. Acad. Sci. USA* 84: 7413–7414) and replication-defective retroviral vectors harboring a therapeutic polynucleotide sequence as part of the retroviral genome (see, e.g., Miller et al. (1990) *Mol. Cell. Biol.* 10:4239 (1990); Kolberg (1992) *J. NIH Res.* 4: 43, and Cornetta et al. (1991) *Hum. Gene Ther.* 2: 215).

For a review of gene therapy procedures, see, e.g., Anderson, *Science* (1992) 256: 808–813; Nabel and Felgner (1993) *TIBTECH* 11: 211–217; Mitani and Caskey (1993) *TIBTECH* 11: 162–166; Mulligan (1993) *Science*, 926–932; Dillon (1993) *TIBTECH* 11: 167–175; Miller (1992) *Nature* 357: 455–460; Van Brunt (1988) *Biotechnology* 6(10): 1149–1154; Vigne (1995) *Restorative Neurology and Neuroscience* 8: 35–36; Kremer and Perricaudet (1995) *British Medical Bulletin* 51(1) 31–44; Haddada et al. (1995) in *Current Topics in Microbiology and Immunology*, Doerfler and Bohm (eds) Springer-Verlag, Heidelberg Germany; and Yu et al., (1994) *Gene Therapy*, 1:13–26.

Widely used retroviral vectors include those based upon murine leukemia virus (MuLV), gibbon ape leukemia virus (GaLV), Simian Immunodeficiency virus (SIV), human immunodeficiency virus (HIV), alphavirus, and combinations thereof (see, e.g., Buchscher et al. (1992) *J. Virol.* 66(5) 2731–2739; Johann et al. (1992) *J. Virol.* 66 (5):1635–1640 (1992); Sommerfelt et al., (1990) *Virol.* 176:58–59; Wilson et al. (1989) *J. Virol.* 63:2374–2378; Miller et al., *J. Virol.* 65:2220–2224 (1991); Wong-Staal et al., PCT/US94/05700, and Rosenburg and Fauci (1993) in *Fundamental Immunology*, Third Edition Paul (ed) Raven Press, Ltd., New York and the references therein, and Yu et al. (1994) *Gene Therapy*, supra; U.S. Pat. No. 6,008,535, and the like).

The vectors are optionally pseudotyped to extend the host range of the vector to cells which are not infected by the retrovirus corresponding to the vector. For example, the vesicular stomatitis virus envelope glycoprotein (VSV-G) has been used to construct VSV-G-pseudotyped HIV vectors which can infect hematopoietic stem cells (Naldini et al. (1996) *Science* 272:263, and Akkina et al. (1996) *J Virol* 70:2581).

Adeno-associated virus (AAV)-based vectors are also used to transduce cells with target nucleic acids, e.g., in the in vitro production of nucleic acids and peptides, and in in vivo and ex vivo gene therapy procedures. See, West et al. (1987) *Virology* 160:38–47; Carter et al. (1989) U.S. Pat. No. 4,797,368; Carter et al. WO 93/24641 (1993); Kotin (1994) *Human Gene Therapy* 5:793–801; Muzyczka (1994) *J. Clin. Invst.* 94:1351 for an overview of AAV vectors. Construction of recombinant AAV vectors are described in a number of publications, including Lebkowski, U.S. Pat. No. 5,173,414; Tratschin et al. (1985) *Mol. Cell. Biol.* 5(11):3251–3260; Tratschin, et al. (1984) *Mol. Cell. Biol.*, 4: 2072–2081; Hermonat and Muzyczka (1984) *Proc. Natl. Acad. Sci. USA*, 81: 6466–6470; McLaughlin et al. (1988) and Samulski et al. (1989) *J. Virol.*, 63:03822–3828. Cell lines that can be transformed by rAAV include those described in Lebkowski et al. (1988) *Mol. Cell. Biol.*, 8:3988–3996. Other suitable viral vectors include, but are not limited to, herpes virus, lentivirus, and vaccinia virus.

V. Kits

In still another embodiment, this invention provides kits for the practice of the methods of this invention. In certain embodiments the kits comprise a nucleic acid that encodes a VGLUT transporter (e.g. a VGLUT1, and/or a VGLUT2, and/or a VGLUT3 transporter) and/or an antibody that specifically binds to a VGLUT transporter, and/or a cell expressing an endogenous VGLUT transporter, and/or a cell transfected with a heterologous nucleic acid capable of expressing a VGLUT transporter. In certain embodiments, the kit comprises a cell and a vector suitable for transfecting the cell with a heterologous nucleic acid capable of expressing a VGLUT transporter. In certain embodiments, the kit comprises a nucleic acid probe that can specifically hybridize to a nucleic acid encoding a VGLUT transporter (e.g. a VGLUT1, and/or VGLUT2, and/or VGLUT3 mRNA). The probe can, optionally, be labeled with a detectable label, e.g., as described herein. In certain embodiments, the kit comprises a vector comprising an expression cassette that expresses a VGLUT transporter. In certain preferred embodiments, the vector is one that permits in vivo transfection of a cell. The kit can optionally include various transfection reagents, (e.g. cationic lipids, dendrimers, and the like).

The kits can optionally include any reagents and/or apparatus to facilitate practice of the methods described herein. Such reagents include, but are not limited to buffers, instrumentation (e.g. bandpass filter), reagents for detecting a signal from a detectable label, transfection reagents, cell lines, vectors, and the like.

In addition, the kits can include instructional materials containing directions (i.e., protocols) for the practice of the methods of this invention. Preferred instructional materials provide protocols for utilizing the kit contents for screening for agents that increase or decrease VGLUT glutamate transporter expression and/or activity, e.g. as described herein. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media can include addresses to internet sites that provide such instructional materials.

EXAMPLES

The following examples are offered to illustrate, but not to limit the claimed invention.

Example 1

Uptake of Glutamate into Synaptic Vesicles by an Inorganic Phosphate Transporter Previous work has identified two families of proteins that transport classical neurotransmitters into synaptic vesicles, but the protein responsible for vesicular transport of the principal excitatory transmitter glutamate has remained unknown. In this example, we demonstrate that a protein that is unrelated to any known neurotransmitter transporters and that was previously suggested to mediate the Na+-dependent uptake of inorganic phosphate across the plasma membrane transports glutamate into synaptic vesicles. In addition, we show that this vesicular glutamate transporter, VGLUT1, exhibits a conductance for chloride that is blocked by glutamate.

Synaptic transmission involves the regulated exocytotic release of neurotransmitter. Because most classical transmitters are synthesized in the cytoplasm, they require transport into the secretory compartment for exocytotic release, and synaptic vesicles exhibit multiple distinct transport activities (Schuldiner et al. (1995) *Physiol. Rev.* 75: 369; Liu and Edwards (1997) *Annu. Rev. Neurosci.* 20: 125). All of these active transport processes depend on the proton electrochemical gradient ($\Delta\mu_{H+}$) across the vesicle membrane generated by the vacuolar H+-dependent adenosine triphosphatase (H+-ATPase) (Forgac (2000) *J. Exp. Biol.* 203: 71) and involve the exchange of lumenal protons for cytoplasmic transmitter. In particular, the transport of monoamines and acetylcholine (ACh) depends primarily on the chemical component ($\Delta$pH) of $\Delta\mu_{H+}$ (Knoth et al. (1981) *Biochemistry* 20: 6625; Anderson et al. (1982) *Biochemistry* 21: 3037), whereas the transport of glutamate depends predominantly on the electrical component ($\Delta\Psi$) (Maycox et al. (1988) *J. Biol. Chem.*, 263: 15423; Carlson et al. (1889) *J. Biol. Chem.* 264: 7369). Accumulation of the inhibitory transmitters-aminobutyric acid (GABA) and glycine relies on both pH and $\Delta\Psi$ (Kish et al. (1989) *Proc. Natl. Acad. Sci., USA*, 86:3877; Hell et al. (1990) *J. Biol. Chem.* 265: 2111). Consistent with the observed differences in mechanism, the vesicular transporters for monoamines and ACh belong to a family of proteins distinct from the vesicular GABA transporter (VGAT) (Liu and Edwards (1997) *Annu. Rev. Neurosci.* 20: 125). VGAT shows greater dependence on $\Delta\Psi$ than do the vesicular monoamine and ACh transporters (McIntire et al. (1997) *Nature* 389: 870), suggesting that the vesicular glutamate transporter, which depends predominantly on $\Delta\Psi$, might belong to the same family of proteins defined by VGAT. Although several other proteins related to VGAT appear to have a role in the recycling of glutamate through glutamine at excitatory synapses (Chaudhry et al. (1999) *Cell* 99: 769; Varoqui et al. (2000) *J. Biol. Chem.* 275: 4049; Sugawara et al.(2000) *J. Biol. Chem.* 275: 16473; Reimer et al. (2000) *Proc. Natl. Acad. Sci., USA*, 97: 7715), none have been implicated in vesicular glutamate transport.

The brain-specific Na+-dependent inorganic phosphate transporter (BNPI) belongs to a family of proteins that use the inwardly directed Na+ gradient across the plasma membrane to cotransport inorganic phosphate (Pi). Originally identified as a sequence up-regulated by the exposure of cerebellar granule cells to subtoxic concentrations of N-methyl-D-aspartate, BNPI mediates the Na+-dependent accumulation of Pi in Xenopus oocytes (Ni et al. (1994) *Proc. Natl. Acad. Sci., USA*, 91: 5607). Additional work has implicated BNPI in adenosine 5'-triphosphate (ATP) production by neurons and protection against excitotoxic injury (16. Glinn et al. (1995) *J. Neurochem.* 65: 2358; Glinn et al. (1998) *J. Neurochem.* 70: 1850). However, BNPI is only expressed by glutamatergic neurons (Ni et al. (1995) *J. Neurosci.* 15: 5789), militating against a general metabolic role in all neuronal populations. In *Caenorhabditis elegans*, genetic screens for multiple behavioral defects have identified mutants in the BNPI ortholog eat-4 (Avery (1993) *Genetics* 133: 897; Berger et al. (1998) *J. Neurosci.* 18: 2871), and recent studies indicate a specific role for eat-4 in glutamatergic neurotransmission (Lee et al. (1999) *J. Neurosci.* 19: 159). The glutamatergic defect in eat-4 mutants appears to be presynaptic, consistent with the localization of BNPI to excitatory nerve terminals (Lee et al. (1999) *J. Neurosci.* 19: 159; Bellocchio et al. (1998) *J. Neurosci.* 18: 8648). The accumulation of cytoplasmic Pi mediated by BNPI may activate the phosphate-activated glutaminase responsible for biosynthesis of the bulk of glutamate released as a neurotransmitter (Bellocchio et al. (1998) *J. Neurosci.* 18: 8648; Hamberger et al. (1979) *Brain Res.* 168: 513; Ward et al. (1983) *J. Neurochem.* 40: 855; Curthoys and Watford (1995) *Annu. Rev. Nutr.* 15: 133). However, the family of proteins including BNPI/EAT-4 may have functions in addition to Pi transport.

BNPI shows sequence similarity to type I but not type II Na+/Pi cotransporters. In contrast to the type II transporters that exhibit robust Na+-dependent Pi uptake, the accumulation of Pi by type I transporters is less striking (Werner et al. *Proc. Natl. Acad. Sci., USA*, 88: 9608; Miyamoto et al. (1995) *Biochem. J.* 305: 81; Busch et al. (1996) *Proc. Natl. Acad. Sci., USA*, 93: 5347). Rather, the type I transporter NaPi-1 transports organic anions, including phenol red and penicillin G, with substantially higher apparent affinity than Pi (Busch et al. (1996) *Proc. Natl. Acad. Sci., USA*, 93: 5347). Human genetic studies have shown that mutations in another protein closely related to BNPI and NaPi-1 account for disorders of sialic acid storage (Verheijen et al. (1999) *Nature Genet.* 23: 462). In these conditions, sialic acid accumulates in lysosomes because of a defect in proton-driven export (Renlund et al. (1986) *Science* 232: 759; Mancini et al. (1989) *J. Biol. Chem.* 264: 15247; Tietze et al. (1989) *J. Biol. Chem.* 264: 15316; Mancini et al. (1992) *Proc. Natl. Acad. Sci., USA*, 89: 6609). Although the sialin protein (Verheijen et al. (1999) *Nature Genet.* 23: 462) has not been demonstrated to mediate sialic acid transport, these observations together with the report that NaPi-1 accumulates organic anions with high apparent affinity suggest that BNPI might also transport organic anions. Localization to glutamatergic nerve terminals raises the possibility that it transports glutamate. In addition, BNPI is localized to synaptic vesicles in the brain (Bellocchio et al. (1998) *J. Neurosci.* 18: 8648) and to intracellular membranes in transfected cells, suggesting a role for BNPI in the transport of glutamate into synaptic vesicles for regulated exocytotic release. To determine whether BNPI mediates the transport of glutamate into synaptic vesicles, we transfected the rat BNPI cDNA into rat pheochromocytoma PC12 cells, which lack detectable endogenous BNPI protein. The rat BNPI cDNA was stably expressed in PC12 cells, and immunofluorescence for BNPI was used to identify the most highly expressing cell clones. Membranes were prepared by homogenizing the washed cells in SH buffer [0.32 M sucrose and 10 mM Hepes-KOH (pH 7.4)] containing protease inhibitors and by pelleting the nuclei at 1000 g for 5 min and the heavier membranes at 27,000 g for 35 min. The supernatant containing lighter membranes was then pelleted at 210,000 g for 1 hour and resuspended in SH buffer with protease inhibitors at a final concentration of ~10 µg protein/µl.

We then prepared a population of light membranes, including synaptic-like microvesicles, from the transfected and untransfected cells (McIntire et al. (1997) *Nature* 389: 870) and tested their ability to accumulate 3H-glutamate in the presence of 4 mM chloride and ATP, conditions that optimize glutamate accumulation by native synaptic vesicles (Maycox et al. (1988) *J. Biol. Chem.*, 263: 15423; Carlson et al. (1889) *J. Biol. Chem.* 264: 7369). To initiate the transport reaction, we added 10 µl of membranes to 190 µl of SH buffer containing 4 mM KCl, 4 mM MgSO4, 4 mM ATP, and 50 µM 3H-glutamate, with other additions noted in the text and figure legends. The reaction mixture was incubated at 29° C. for varying times, and the uptake was terminated by rapid filtration, followed by immediate washes with 6 ml of cold 0.155 M potassium tartrate and 10 mM Hepes (pH 7.4). Background uptake was determined using membranes prepared from untransfected cells that were incubated for the same amount of time at the same temperature. Transport measurements were performed in duplicate with at least two different preparations of membranes. The Km was calculated by averaging the results of two separate determinations.

Membranes from the transfected cells exhibited an uptake of glutamate that was two to four times the uptake by membranes from untransfected cells (FIG. 2A), a signal very similar to that obtained for GABA transport by VGAT (McIntire et al. (1997) *Nature* 389: 870).

Figure 2B:
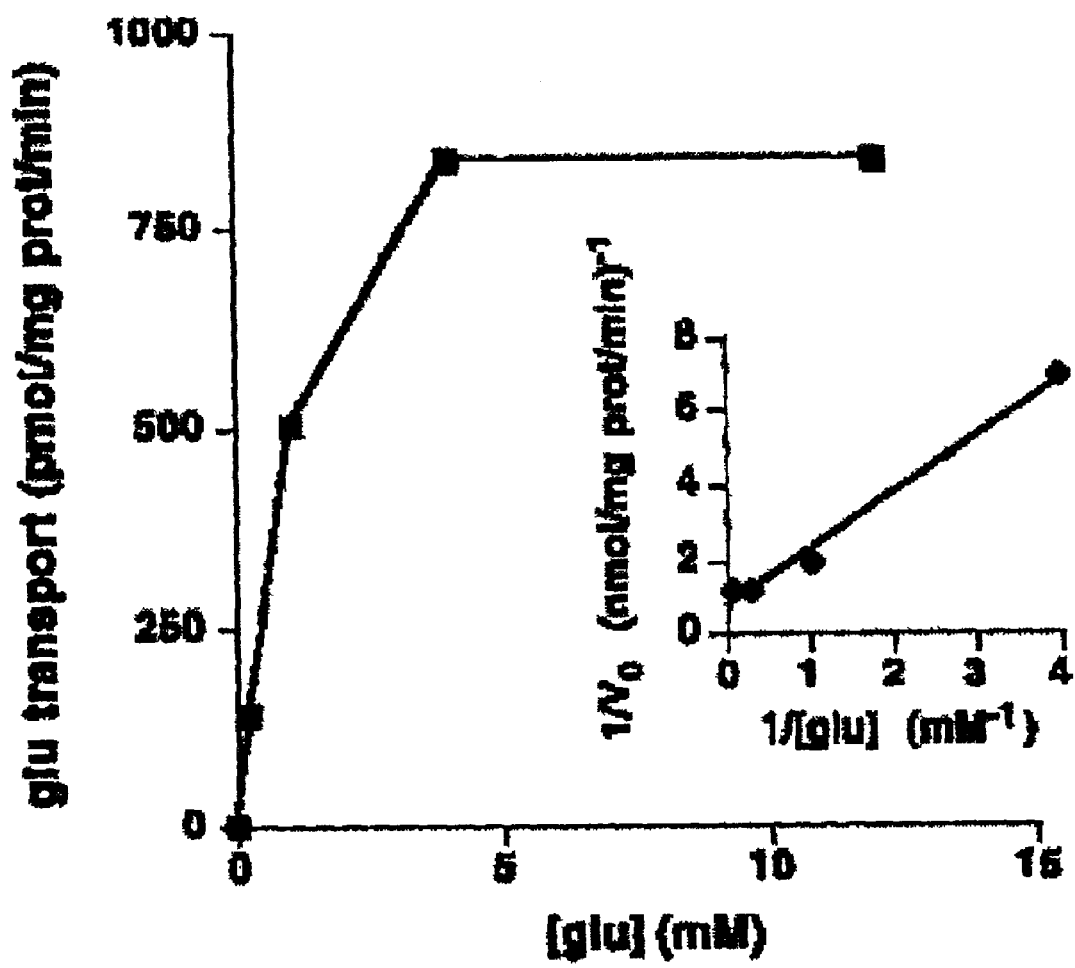
Figure 3:
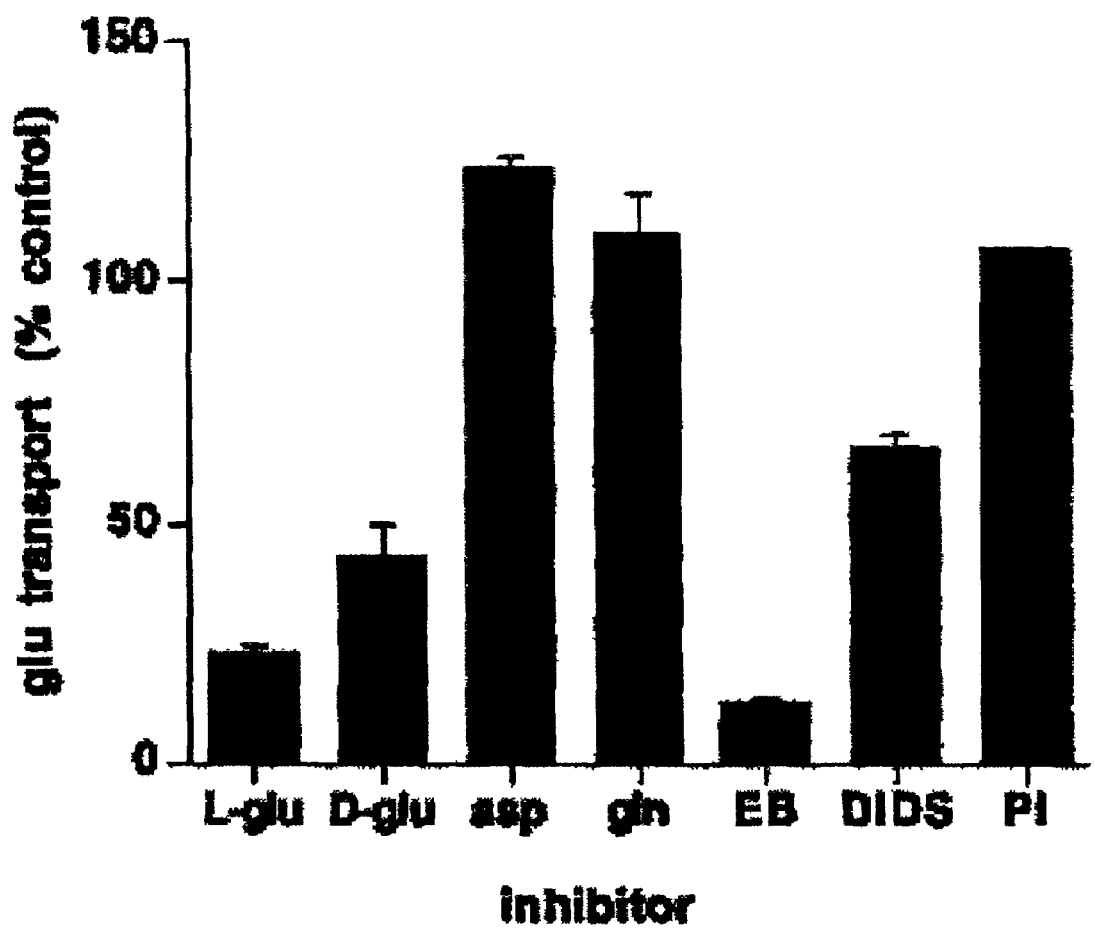
FIG. 3 illustrates inhibition of BNPI transport by amino acids and other compounds. L-Glutamate (L-glu), but not L-aspartate (asp) or L-glutamine (gln) (all 10 mM), markedly inhibits the uptake of $^3$H-glutamate at 5 min by membranes expressing BNPI. D-Glutamate (D-glu) (10 mM) partially inhibits the uptake. Evans blue (EB) (5 μM) also inhibits BNPI activity dramatically, whereas 1 μM DIDS blocks transport only partly, and 10 mM Pi has little effect. Uptake by membranes from untransfected PC12 cells (also for 5 min) was subtracted from that observed in the transfected cell membranes, and the results were normalized to uptake by transfected cell membranes in the absence of inhibitors. The compounds had no significant effect on the background uptake by untransfected cell membranes. The results represent the average from at least two experiments performed in duplicate, and the error bars represent the standard deviation.

Glutamate transport into synaptic vesicles exhibits a number of properties that distinguish it from glutamate uptake by other transport systems. First, in contrast to plasma membrane glutamate uptake (Amara and Kuhar (1993) *Annu. Rev. Neurosci.* 16: 73; Kanner (1993) *FEBS Lett.* 325: 95), the accumulation of glutamate in synaptic vesicles does not rely on a Na+ electrochemical gradient. Consistent with this, glutamate was transported by BNPI in the absence of Na+ (FIG. 2). Second, vesicular glutamate transport has a substantially lower apparent affinity ($K_m$ of ~1 mM) than the plasma membrane excitatory amino acid transporters ($K_m$ of ~10 to 100 µM). Glutamate transport by BNPI is saturated with a $K_m$ of ~2 mM (FIG. 2B), in the same range as transport by synaptic vesicles. The slightly lower apparent affinity relative to synaptic vesicles may reflect a reduced driving force for transport in the PC12 membranes. Third, plasma membrane glutamate transporters recognize both aspartate and glutamate as substrates, whereas vesicular glutamate transport does not recognize aspartate (Maycox et al. (1988) *J. Biol. Chem.*, 263: 15423; Carlson et al. (1889) *J. Biol. Chem.* 264: 7369). Although 10 mM L-glutamate inhibited the uptake of 3H-glutamate by membranes from BNPI-expressing cells, 10 mM L-aspartate did not (FIG. 3). D-Glutamate partially inhibited the transport of $^3$H-glutamate, and L-glutamine had no effect, also consistent with prior work (Naito and Ueda (1983) *J. Biol. Chem.* 258: 696). Fourth, low micromolar concentrations of the dye Evans blue inhibited the transport of glutamate into both synaptic vesicles (40) and membranes expressing BNPI (FIG. 3).

Figure 4A:
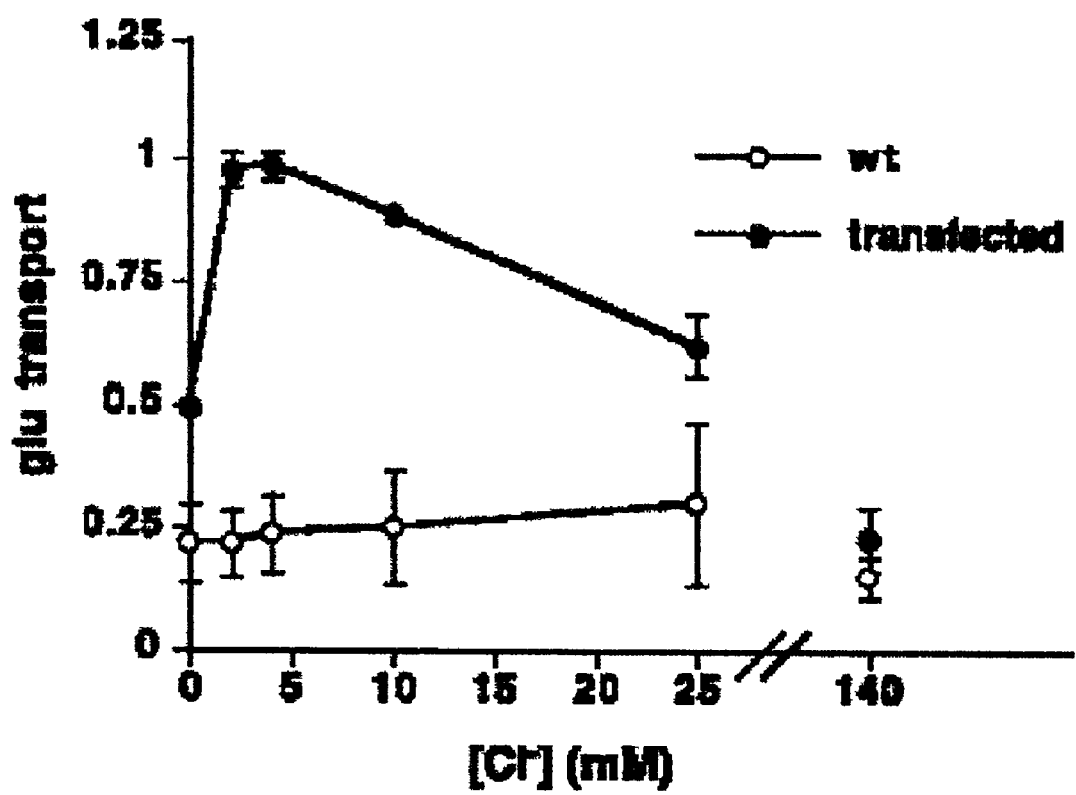
FIGS. 4A and 4B show the ionic dependence of transport by BNPI.

Vesicular glutamate transport has a biphasic dependence on chloride concentration that may reflect the presence of an anion binding site distinct from the site of substrate recognition (Hartinger and Jahn (1993) *J. Biol. Chem.* 268: 23122). Chloride concentrations of ~4 to 10 mM appear optimal for transport, with substantially lower activity detected at higher and lower levels (Maycox et al. (1988) *J. Biol. Chem.*, 263: 15423; Carlson et al. (1889) *J. Biol. Chem.* 264: 7369). Thus, we tested the chloride dependence of glutamate transport mediated by BNPI. Maximal uptake of $^3$H-glutamate by BNPI was conferred by 2 to 4 mM chloride, with much less activity detected at 0 and 25 mM (FIG. 4A). Variation in the chloride concentration, as well as other manipulations including the addition of L-glutamate and Evans blue, had little effect on the background glutamate uptake observed in membranes from untransfected cells (FIG. 4A). In addition, the anion transport blocker 4,4'-diisothiocyanatostilbene-2,2'-disulfonic acid (DIDS) inhibits glutamate transport by synaptic vesicles with a median inhibitory concentration of ~0.7 µM, apparently by interacting with the distinct chloride recognition site; here, 1 µM DIDS inhibited ~60% of the 3H-glutamate transport mediated by BNPI (FIG. 3). The dependence of BNPI on the proton electrochemical gradient also strongly resembled that observed for glutamate transport into synaptic vesicles.

Figure 4B:
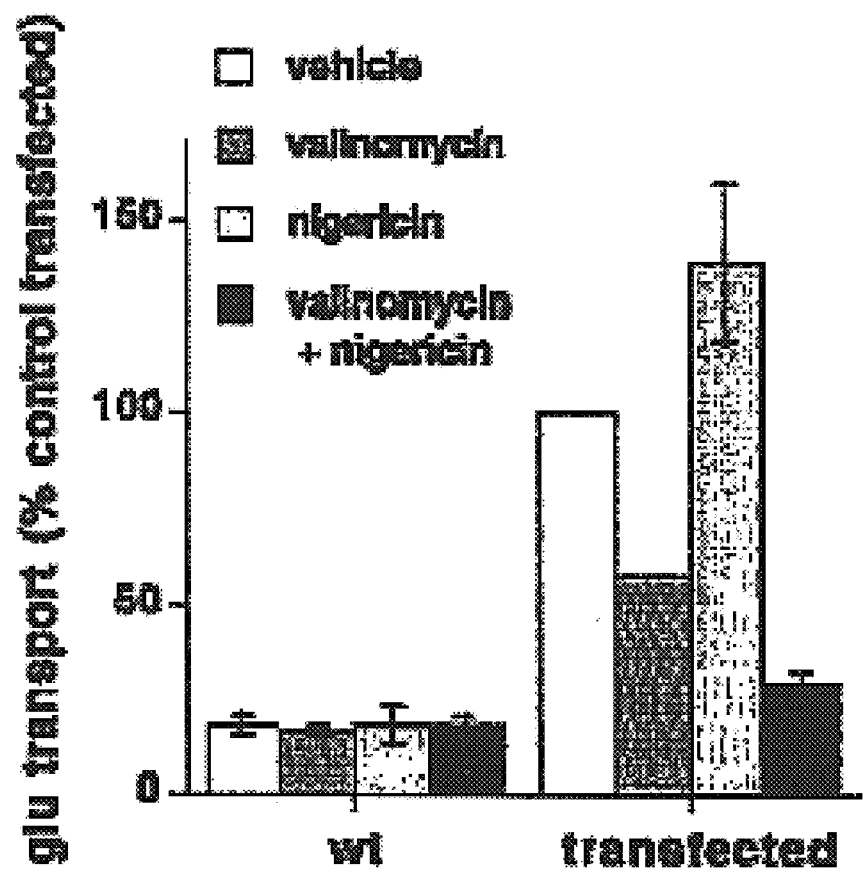

Glutamate transport into synaptic vesicles relies primarily on the electrical component $\Delta\Psi$ of the $\Delta_{\mu H+}$ across the vesicle membrane Maycox et al. (1988) *J. Biol. Chem.*, 263:15423; Carlson et al. (1889) *J. Biol. Chem.* 264: 7369; Moriyama and Yamamoto (1995) *J. Biol. Chem.* 270: 22314; Wolosker et al. (1996) *J. Biol. Chem.* 271: 11726). To assess the dependence of transport mediated by BNPI on $\Delta\Psi$, we used membranes preloaded with 4 mM KCl and the K+ ionophore valinomycin. With 4 mM KCl in the reaction solution as well as in the membranes, valinomycin dissipates (Wolosker et al. (1996) *J. Biol. Chem.* 271: 11726) and substantially reduces glutamate uptake by BNPI (FIG. 4B). The ionophore nigericin, which exchanges K+ for H+ and dissipates $\Delta$pH, increases both $\Delta\Psi$ and glutamate uptake by synaptic vesicles at low chloride concentrations and sub-saturating amounts of glutamate (Wolosker et al. (1996) *J. Biol. Chem.* 271: 11726; Tabb et al. (1992) *J. Biol. Chem.* 267: 15412). Under these same conditions, nigericin increased the uptake of 3H-glutamate by BNPI (FIG. 4B). The addition of both nigericin and valinomycin essentially abolished glutamate uptake by native synaptic vesicles and BNPI (FIG. 4B), presumably because the increase in $\Delta\Psi$ produced by nigericin is eliminated by valinomycin. The residual activity present in valinomycin that was abolished by the addition of nigericin also suggests that the transporter can use the outwardly directed $\Delta$pH to drive transport in the absence of $\Delta\Psi$.

Native synaptic vesicles acidify during glutamate uptake (Maycox et al. (1988) *J. Biol. Chem.*, 263: 15423). Glutamate presumably serves as a counterion for protons and dissipates $\Delta\Psi$, enabling the vacuolar H+-ATPase to generate a larger $\Delta$pH, but cotransport of H+ with glutamate remains an alternative possibility. To determine whether acidification also accompanies glutamate transport by BNPI, we used the quenching of acridine orange fluorescence to measure vesicle pH. Membranes (200 µg of protein) were diluted into 2 ml of 0.3 M sucrose and 10 mM tris-Mops (pH 7.4) containing 4 mM MgSO4 and 5 µM acridine orange and incubated at 37° C. with continuous stirring. Fluorescence was monitored with a Hitachi F4500 spectrofluorimeter at an excitation wavelength of 492 nm and emission of 530 nm. Separate measurements were made with at least three different membrane preparations for wild-type and transfected cells; representative tracings are shown in FIG. 5.

Figure 5D:
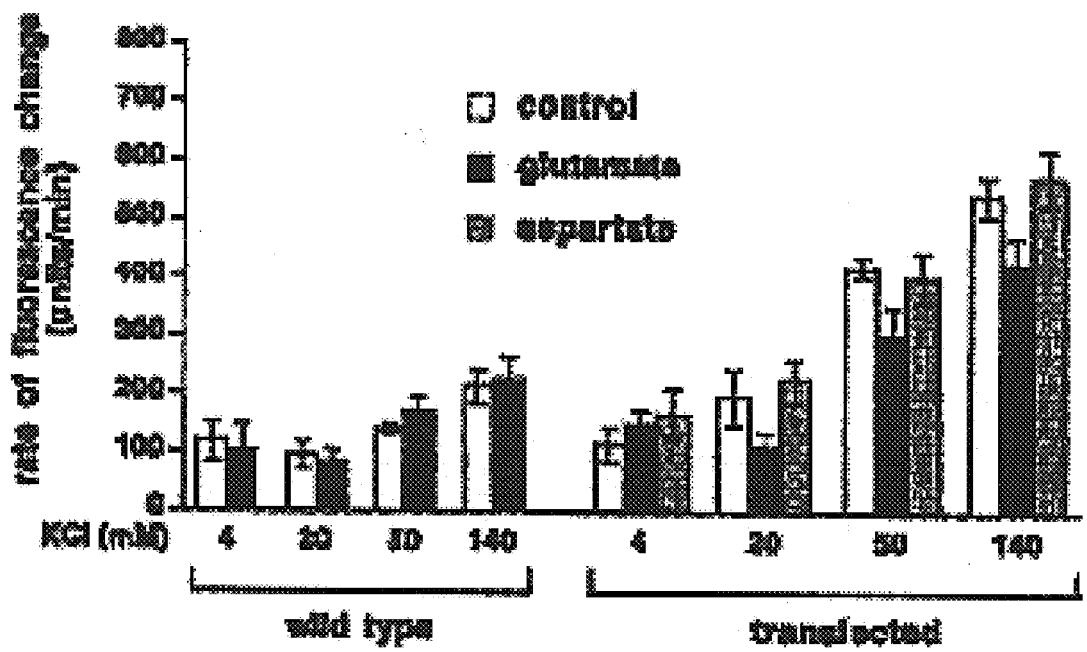

In the presence of ATP and 4 mM KCl, the addition of 10 mM glutamate reduced the lumenal pH of membranes expressing BNPI but not of membranes from untransfected cells (FIG. 5A). However, we also noted that 90 mM KCl produced acidification of the BNPI-expressing membranes that was considerably greater than that of the control membranes, suggesting that BNPI exhibits a conductance for chloride as well as transport activity for glutamate. To characterize further the chloride conductance, we examined the effect of a range of chloride concentrations on vesicle pH in the absence of glutamate. Membranes from multiple cell lines expressing BNPI all exhibited substantially greater acidification than wild-type membranes did, particularly at higher chloride concentrations (FIGS. 5, B and D). To assess the relation of the chloride conductance to glutamate transport, we pretreated the membranes with 10 mM glutamate and found that this decreased the acidification produced by chloride (FIGS. 5, C and D). Because the membranes evidently express chloride conductances in addition to BNPI, the increase in conductance due to BNPI appears large, and the inhibition by glutamate is substantial. The nontransported amino acid aspartate (10 mM) failed to reduce the acidification by chloride (FIGS. 5, C and D), supporting the relevance of the glutamate effect on chloride-induced acidification for glutamate transport. Further, glutamate had no effect on the acidification produced by chloride in nontransfected cell membranes (FIG. 5D), supporting the specificity of the interaction with BNPI.

BNPI transports glutamate with all of the functional characteristics previously reported for glutamate transport into native synaptic vesicles from the brain. It also localizes to synaptic vesicles (Bellocchio et al. (1998) *J. Neurosci.* 18: 8648), and the *C. elegans* mutation eat-4 reduces glutamate release (Lee et al. (1999) *J. Neurosci.* 19: 159). BNPI thus functions as a vesicular glutamate transporter, VGLUT1. Only a subset of glutamate neurons expresses VGLUT1 (Ni et al. (1995) *J. Neurosci.* 15: 5789; Bellocchio et al. (1998) *J. Neurosci.* 18: 8648), but a closely related sequence has recently been identified and appears to be expressed in brain regions that lack VGLUT1 (Aihara et al. (2000) *J. Neurochem.* 74: 2622). The two isoforms together may therefore account for the uptake of glutamate by synaptic vesicles from all glutamatergic neurons.

The structural similarity of VGLUT1 to sialin and NaPi-1 may reflect similarities in the ionic dependence of transport. The extrusion of sialic acid from lysosomes, which appears to be defective in sialic acid storage diseases, depends on cotransport with H+ (Renlund et al. (1986) *Science* 232: 759; Mancini et al. (1989) *J. Biol. Chem.* 264: 15247; Tietze et al. (1989) *J. Biol. Chem.* 264: 15316; Mancini et al. (1992) *Proc. Natl. Acad. Sci., USA*, 89: 6609), and vesicular glutamate transport may involve a proton exchange mechanism (Tabb et al. (1992) *J. Biol. Chem.* 267: 15412). The expression of NaPi-1 in Xenopus oocytes confers a large chloride conductance blocked by the organic anions that are recognized as substrates for transport (Busch et al. (1996) *Proc. Natl. Acad. Sci., USA*, 93: 5347). We found that the closely related VGLUT1 exhibits a substantial chloride conductance in addition to the unusual biphasic dependence on chloride previously reported for glutamate transport into synaptic vesicles. Glutamate blocks this chloride conductance, suggesting that the two anions compete for permeation. It remains unknown whether glutamate and chloride share a common pathway for permeation through VGLUT1, but a channel-like mode or anion exchange mechanism may enable the rapid filling necessary to keep up with the high rates of transmitter release and synaptic vesicle recycling observed at glutamatergic synapses.

The relation between glutamate and Pi transport by VGLUT1 remains unclear. High concentrations of Pi did not inhibit glutamate transport by VGLUT1 (FIG. 3). In addition, the related sialin protein apparently functions to transport sialic acid rather than Pi (Verheijen et al. (1999) *Nature Genet.* 23: 462). NaPi-1 also recognizes organic acids with higher affinity than Pi (Busch et al. (1996) *Proc. Natl. Acad. Sci., USA*, 93: 5347). Further, Pi transport does not correlate with other activities, such as the chloride conductance induced by NaPi-1 expression in Xenopus oocytes, and has properties similar to endogenous oocyte Pi uptake (Bröer et al. (1998) *J. Membr. Biol.* 164: 7). Nonetheless, previous work has demonstrated the Na+-dependent uptake of Pi by NaPi-1 and BNPI (Ni et al. (1994) *Proc. Natl. Acad. Sci., USA*, 91: 5607; V). VGLUT1 may thus function as both a phosphate transporter, presumably at the plasma membrane, and a glutamate transporter in synaptic vesicles. The localization of VGLUT1 to synaptic vesicles, the phenotype of the eat-4 mutant, and the biochemical evidence presented here, however, strongly suggest that vesicular glutamate transport is its primary role.

Example 2

The Expression of Vesicular Glutamate Transporters Defines Two Classes of Excitatory Synapse The quantal release of glutamate depends on its transport into synaptic vesicles. As demonstrated in example 1, a protein previously implicated in the uptake of inorganic phosphate across the plasma membrane catalyzes glutamate uptake by synaptic vesicles. However, only a subset of glutamate neurons express this vesicular glutamate transporter (VGLUT1). In this example, we show that excitatory neurons lacking VGLUT1 express a closely related protein that has also been implicated in phosphate transport. Like VGLUT1, this protein localizes to synaptic vesicles and functions as a vesicular glutamate transporter (VGLUT2). The complementary expression of VGLUT1 and 2 defines two distinct classes of excitatory synapse.

Results

DNPI more closely resembles VGLUT1 than other type I phosphate transporters such as NaPi-1 and sialin (FIG. 6), suggesting that it may also transport glutamate into synaptic vesicles. In addition, DNPI is expressed selectively in the nervous system (Aihara (2000) *J. Neurochem.* 74: 2622–2625) where it appears to have a distribution different from VGLUT1 (Hisano et al. (2000) *Mol. Brain Res.* 83: 34–43).

Complementary Expression by Excitatory Neurons

Figure 7:
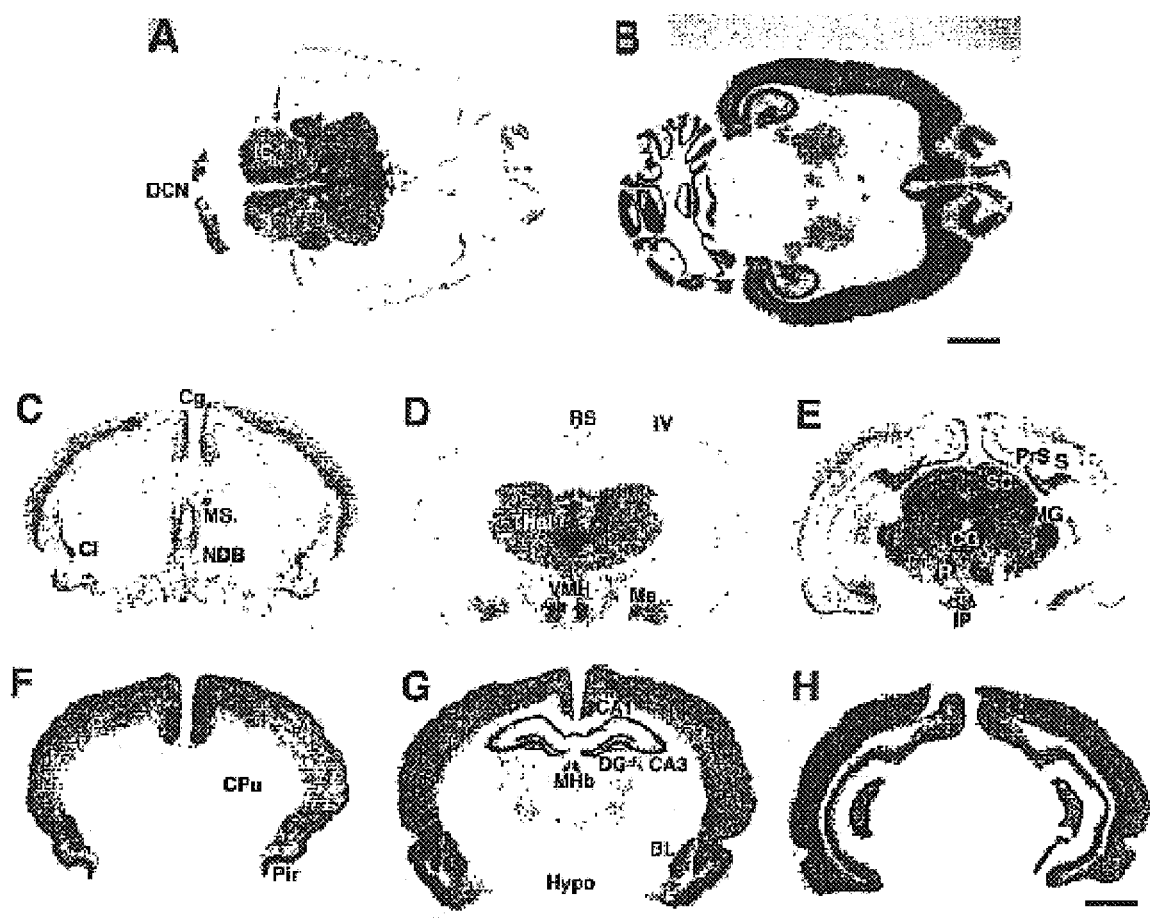
FIG. 7, panels A through H show differential expression of DNPI and VGLUT1 by in situ hybridization. Horizontal (Panels A and B) and coronal (Panels C–H) brain sections from 3-week old rats were hybridized with $^{35}$S-labeled antisense RNA probes derived from unique carboxy-terminal and 3'-untranslated regions of rat DNPI/VGLUT2 (A,C–E) or VGLUT1 (B,F–H) cDNAs and exposed to film for 3 days. The cortex, hippocampus and cerebellar cortex express predominantly VGLUT1 whereas the thalamus, brainstem and deep cerebellar nuclei (DCN) express predominantly DNPI. Within the cortex, DNPI is expressed predominantly by neurons in layer IV whereas VGLUT1 is expressed by layers II–VI. The caudate-putamen (CPu), containing largely inhibitory neurons, expresses neither sequence (Panels C and F). In addition, the medial septum (MS), nuclei of the diagonal band (NDB) and hypothalamus (Hypo) express only DNPI (Panel C). Within the hippocampus, DNPI occurs at low levels in the pyramidal cell layer relative to VGLUT1, but is slightly higher in CA1 and 2 than in other fields, and is undetectable in the dentate gyrus (Panels D and G). In contrast, VGLUT1 shows robust expression by pyramidal neurons and granule cells in all areas (Panel G). Numerous thalamic (Thal) and hypothalamic nuclei (such as the ventromedial nucleus, VMH) express DNPI but very little VGLUT1 (Panels D and G). In the amygdala, the medial nucleus (Me) hybridizes exclusively for DNPI whereas the lateral and basolateral (BL) nuclei hybridize more strongly for VGLUT1. Abbreviations not defined above: IC, inferior colliculi; CG, anterior cingulate cortex; Cl, claustrum; RS, retrospenial cortex; PrS, presubiculum; S, subiculum; SC, superior colliculus; MG, medial geniculate; CG, central gray; R, red nucleus; IP, interpeduncular nucleus; Pir, piriform cortex; MHb, medial habenula. Scale bars=2 mm (Panels A, B), 1.25 mm (Panels C–H).

To determine whether DNPI is expressed by excitatory neurons that do not express VGLUT1, we examined the distribution of the two transcripts in adjacent brain sections by in situ hybridization. The closely related sequences were distinguished using probes from the 3' end of the protein-coding regions (and part of the 3' untranslated regions), where the cDNAs are divergent. Further, longer probes containing more of the shared protein-coding sequence hybridized in a distribution identical to the shorter probes. The discrete patterns of hybridization observed also indicate essentially no cross-reactivity between the two sequences. On horizontal sections, the brainstem labels strongly for DNPI and very little if at all for VGLUT1 (FIG. 7, panels A and B). In the cerebellum, the cortex hybridizes to VGLUT1 but not to DNPI whereas the deep nuclei hybridize selectively to DNPI. Thus, the pattern of expression appears largely complementary. The analysis of coronal sections further shows that the septal nuclei, nuclei of the diagonal band, hypothalamus and the midbrain express DNPI but not VGLUT1 (FIG. 7, panels C–H).

Several brain regions express both DNPI and VGLUT1, but in most of these, one transcript predominates and the patterns of expression remain distinct. All cortical layers label strongly for VGLUT1 whereas only layer IV of frontal and parietal cortex and layers IV and VI of temporal cortex label for DNPI (FIG. 7). In the hippocampus, dentate gyrus granule cells contain only VGLUT1 mRNA (FIG. 7, panel G). Pyramidal neurons from CA1 through CA3 also express abundant VGLUT1, but lower levels of DNPI occur as well (FIG. 7D). CA1 in particular labels for DNPI more strongly than other hippocampal fields, but the subiculum and presubiculum contain abundant DNPI mRNA (FIG. 7, panel E).

The thalamus expresses much more DNPI than VGLUT1 (FIG. 7, panel D), but certain thalamic nuclei such as the medial habenula hybridize to VGLUT1 (FIG. 7). In the amygdala, the medial and central nuclei contain abundant mRNA for DNPI, and the lateral and basolateral nuclei for VGLUT1 (FIG. 7, panels D and G). Expression of the two transcripts thus appears largely segregated to distinct neuronal populations.

We have not detected any discrete population of excitatory neurons that do not express either VGLUT1 or DNPI. We have also not detected any expression of DNPI or VGLUT1 by non-glutamatergic neurons. The caudate-putamen, which contains largely inhibitory projection neurons and cholinergic interneurons, lacks hybridization signal for either sequence (FIG. 7, panels C and F). Similarly, Purkinje cells in the cerebellum and other inhibitory neurons in the cerebellar cortex and hippocampus do not express detectable levels of either transcript (data not shown). Further, monoamine cell groups in the substantia nigra, locus coeruleus and raphe nuclei, and motor nuclei in the brainstem do not express detectable DNPI or VGLUT1 transcripts.

Localization to Excitatory Synapses

Figure 6A:
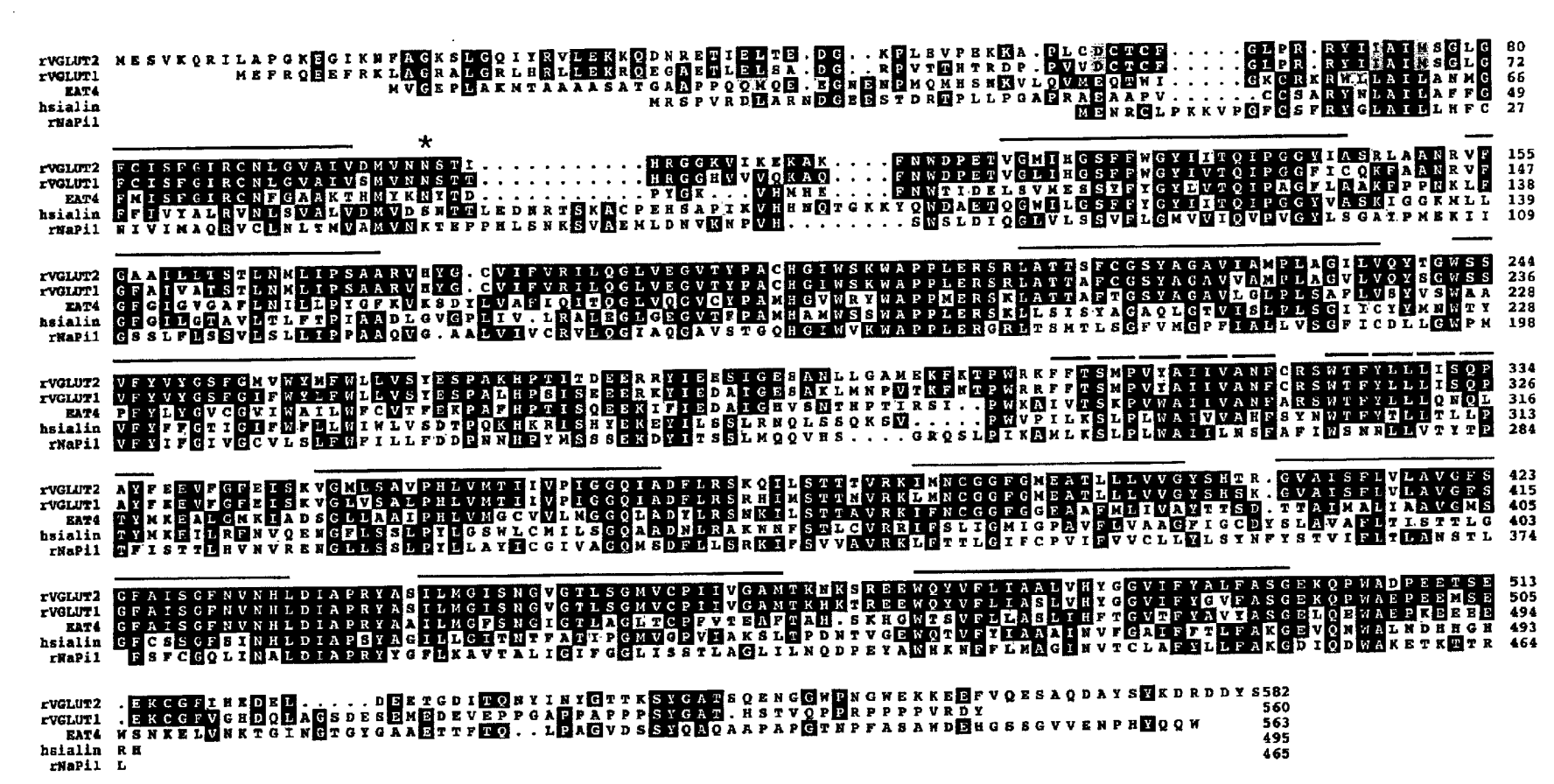
Figure 6B:
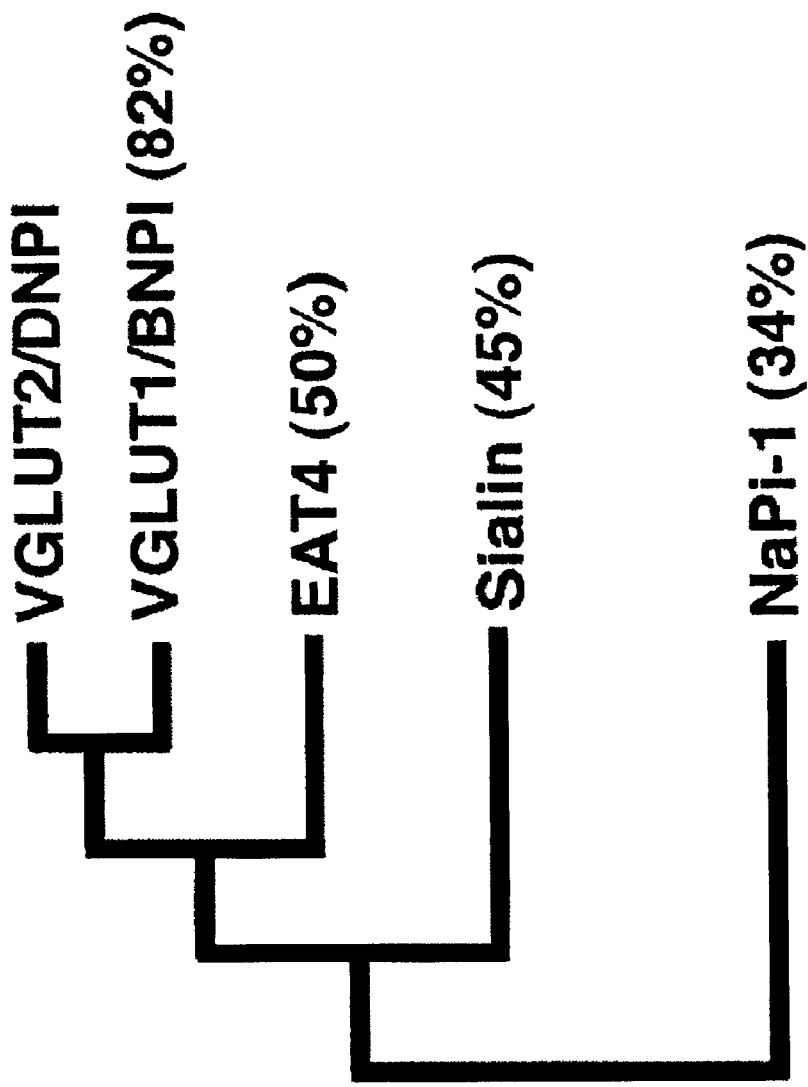

To determine whether DNPI localizes to excitatory synapses like VGLUT1 (Bellocchio et al. (1998) *J. Neurosci.* 18: 8648–8659), we raised an antibody to a bacterial fusion protein containing the cytoplasmic C-terminus of the rat protein. The domain used to produce the antisera shows very little similarity to the corresponding carboxy-terminal domain from VGLUT1, sialin or NaPi-1 (FIG. 6A and 6B). By western analysis, the antibody recognizes DNPI but not VGLUT1 stably expressed in PC12 cells. Nonetheless, to ensure specificity, we adsorbed both the DNPI antibody with the VGLUT1 fusion protein (Bellocchio et al. (1998) *J. Neurosci.* 18: 8648) and the VGLUT1 antibody with the DNPI fusion protein. The distinct patterns of immunostaining observed for each antibody indeed confirm the lack of cross-reactivity. In contrast to the detection of VGLUT mRNA in cell bodies, the VGLUT proteins localize to processes.

Figure 8:
FIG. 8, panels A through 8F illustrate complementary expression of VGLUT proteins in synaptic layers. Adjacent rat brain sections were immunostained using the peroxidase method for DNPI/VGLUT2 (panels A, C, and E) and VGLUT1 (panels B, D, and F). In all regions, the immunoreactivity for both proteins appears punctate and restricted to gray matter, suggesting expression at synapses. At the level of the caudate-putamen (CPu) and nucleus accumbens (NAc) (panels A and B), the striatum labels for both proteins, but DNPI clearly predominates in the ventral pallidum and nucleus of the diagonal band (NDB). In the cortex, DNPI localizes to layers IV and VI, and VGLUT1 to all layers. (Tu=olfactory tubercle, Pir=piriform cortex). At the level of the caudal diencephalon (CD), DNPI immunoreactivity is much more prominent than VGLUT1 in thalamic nuclei, particularly medial and intralaminar nuclei (MI), and in hypothalamic nuclei, especially the dorsomedial (DM) and lateral nuclei (LH). Sensory relay nuclei of the thalamus, including the ventroposteromedial nucleus (VPM), ventroposterolateral nucleus (VPL) and the lateral geniculate (LG) nucleus label for both proteins. However, these nuclei vary in the extent of labeling, with VPM and VPL nuclei more strongly immunoreactive for DNPI than the posterior (Po) nucleus and the dorsal lateral geniculate (dLG) more reactive for VGLUT1 than the ventral lateral geniculate (vLG). Both DNPI and VGLUT1 are found throughout the amygdaloid complex (Am). At the level of the midbrain (panels E and F), most brainstem structures lack VGLUT1 immunoreactivity whereas the midbrain shows widespread staining for DNPI in the superior colliculus (SC), central gray (CG), substantia nigra pars compacta (SNc) and substantia nigra pars reticulata (SNr). The mammillary nucleus (MM) and medial geniculate body (MG) contain both proteins. The presubiculum (PrS, notably layer III), but not the subiculum (S), strongly labels for DNPI, whereas VGLUT1 shows the opposite pattern of immunoreactivity. Distinct, complementary patterns of immunostaining are present in the hippocampus (see also FIG. 9). Although VGLUT1 immunoreactivity predominates, stratum lacunosum-moleculare (1 m) also contains DNPI. Preadsorption with the VGLUT2-GST fusion protein eliminated the immunoreactivity observed with DNPI antibody (see FIG. 9). Scale bar=1 mm (all panels).
Figure 8:
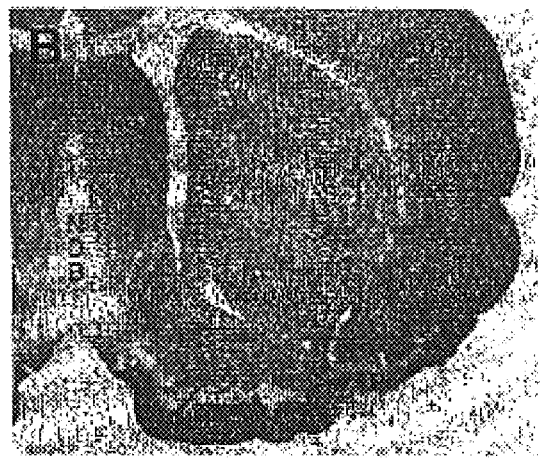
Figure 8:
Figure 8:
Figure 8:
Figure 8:

Although brain regions such as the caudate-putamen label with both antibodies, presumably due to the expression of DNPI and VGLUT1 by distinct afferents, the immunoreactivity in many other areas appears segregated (FIG. 8). The neocortex stains more strongly overall for VGLUT1 than DNPI, but layers IV and VI stain for DNPI and the VGLUT1 immunoreactivity appears less intense in these layers (FIG. 8, panels A and B). In addition, the piriform cortex stains more strongly for VGLUT1 than DNPI. The septal region also shows opposing gradients of labeling, with more VGLUT1 laterally and DNPI alone in the medial septum and nuclei of the diagonal band. At the level of the diencephalon, particular thalamic nuclei exhibit strong labeling for DNPI. FIG. 8, panel C shows that the midline, intralaminar and, to a lesser extent, lateral geniculate, ventroposterior medial and lateral nuclei stain more strongly for DNPI than the posterior nucleus. Conversely, the lateral nuclei stain more strongly for VGLUT1 than medial nuclei (FIG. 8, panel D). The hypothalamus also shows more immunoreactivity for DNPI than VGLUT1, but with discrete areas of increased VGLUT1 labeling such as the ventromedial (FIG. 8, panel D) and mammillary nuclei (FIG. 8, panel F). The amygdala stains almost equally with the two antibodies, with slight differences in pattern. At the level of the midbrain, the DNPI antibody produces widespread labeling, with VGLUT1 detectable only in the medial geniculate nucleus of the thalamus (FIG. 8, panels E and F). Layers I and III of the presubiculum stain strongly and selectively for DNPI, likely reflecting commissural afferents from neurons in the contralateral presubiculum (van Groen and Wyss (1990) *Brain Research* 518: 227–243) that express DNPI mRNA (FIG. 7, panel E). In contrast, layer II and the subiculum stain preferentially for VGLUT1. DNPI and VGLUT1 thus exhibit complementary patterns of protein as well as mRNA expression.

Figure 9:
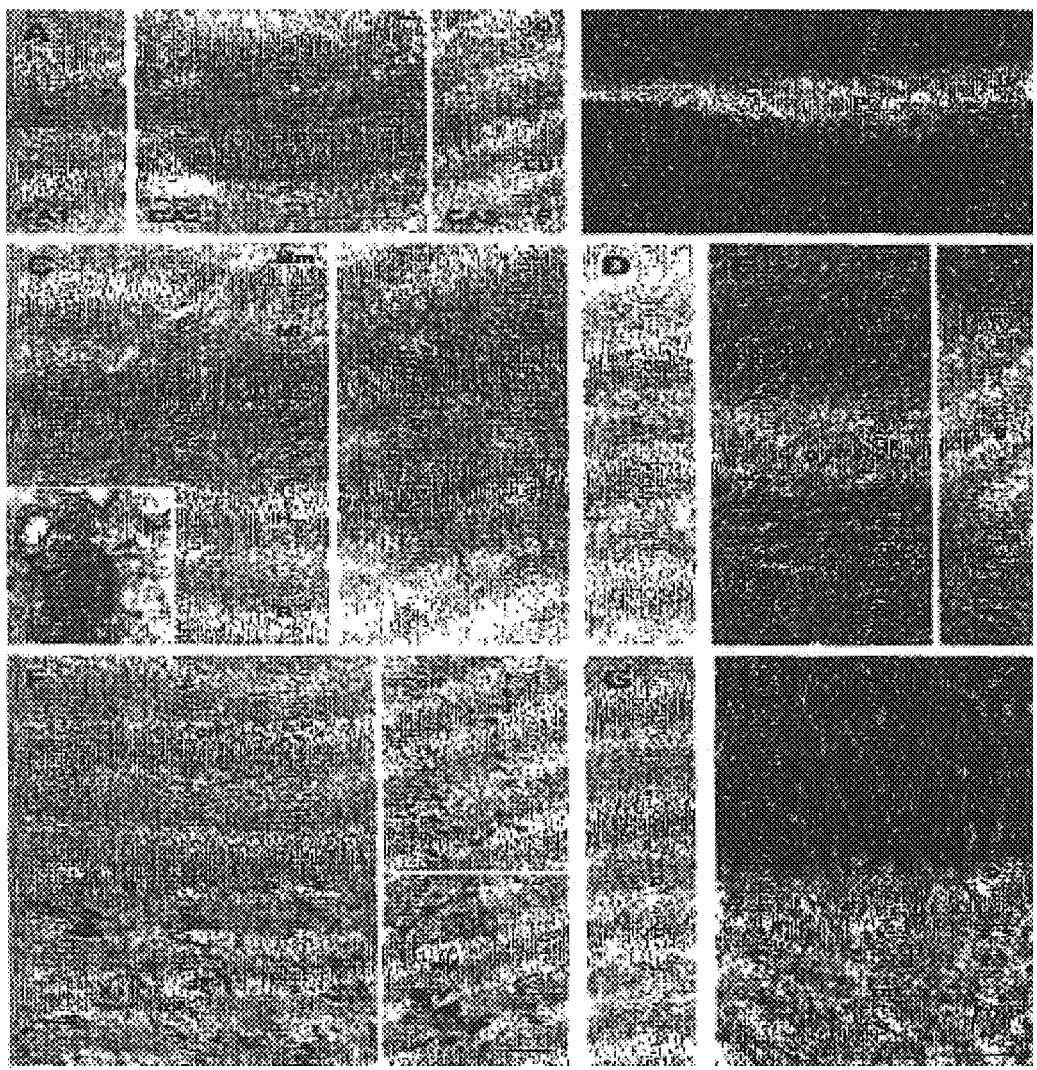
FIG. 9, panels A through G illustrate. complementary expression of VGLUT proteins in the hippocampus and cerebellar cortex. Panel A: In the hippocampus, DNPI/VGLUT2-immunoreactivity localizes selectively to nerve endings in the pyramidal layer (P) of CA2 (and immediately adjacent CA3), but not CA1 or CA3. Pyramidal cell bodies (p) are not immunoreactive. Panel B: VGLUT1, in contrast, localizes throughout CA1–3 in small puncta distributed uniformly in strata oriens (O) and radiatum (R) (representing the terminals of the Schaffer collateral system from CA3 pyramidal cells), and in large, mossy fiber boutons in stratum lucidum (LU), representing the terminals of the axons from dentate granule cells (Storm-Mathisen et al. (1983) *Nature* 301: 517–520). Panel C: In the dentate gyrus, DNPI localizes selectively to nerve endings in the granular layer (Gr), particularly in its superficial parts. Granule cell bodies (g) are unstained. Right panel: High magnification view of a different section under oil immersion. Inset: electron micrograph showing the synapse of an immunoreactive nerve terminal onto a dendrite in the granule cell layer; arrowheads indicate synaptic vesicles, open arrowheads point to synaptic site (Stanfield and Cowan (1984) Brain Res. 309: 299–307). Panels D and G: Preadsorption of DNPI serum with DNPI-GST fusion protein (20 μg/ml) abolishes the staining of nerve terminals. Panel E: VGLUT1 localizes to small puncta in all the other layers of the dentate gyrus, including puncta in the molecular layer (with the middle zone (Mm) containing terminals of the medial perforant path, and the inner zone (Mi) terminals of mossy cells in the hilus (H)), and large, mossy fiber boutons. (Stratum radiatum (R) of CA3 appears near the bottom of the main panel.) Right panel: High magnification view under oil immersion shows immunoreactive nerve endings in layers Mi and H. The distribution of DNPI/VGLUT2-immunoreactive boutons (A,C) conforms to the distribution of afferents from the supramammillary nucleus (Amaral, D. G., and Witter, M. P. (1995) Pp 443–495 In:. *The Rat Nervous System, Second Edition.*, G. Paxinos, ed. (San Diego: Academic Press)), whereas the distribution of VGLUT1-immunoreactive boutons (B,E) conforms to that of the main glutamate immunoreactive systems (Storm-Mathisen et al. supra.). Panel F: In the cerebellum, DNPI/VGLUT2 localizes to climbing fiber boutons (clf) in the molecular layer, and to mossy fiber boutons (mf) in the granule cell layer. Insets: high magnification view under oil immersion showing clf, and two different shapes of mf. Panel H: Dense VGLUT 1-immunoreactive puncta representing parallel fiber boutons fill the molecular layer, and show unstained structures in silhouette: Bergmann astroglia (b), Purkinje cell dendrites (d) and cell bodies (p), stellate intemeurons (s), and blood vessels (not indicated). In addition, VGLUT1 is expressed in mossy fiber boutons (mf). Sections were viewed by differential interference contrast (DIC) optics. Scale bar shown in A: A (all panels), C–E (main panels), 50 μm; B, 100 μm; C and E right panels, 20 μm; C inset, 0.3 μm. Scale bar in F–H, 30 μm; F insets, 10 μm.

Consistent with expression at synapses, DNPI localizes to punctate structures in the neuropil (FIG. 9). In the hippocampus, the pyramidal cell layer of CA2 shows puncta immunoreactive for DNPI whereas VGLUT1-positive puncta are distributed uniformly in stratum oriens and radiatum throughout CA1–3 (FIG. 9, panels A and B). Although CA1 and 3 do not generally contain DNPI immunoreactivity, stratum lacunosum-moleculare immunostains strongly for DNPI in the temporal fields of CA1 (FIG. 8, panel E), suggesting expression by afferents from the midline reuniens nucleus of the thalamus as well as the entorhinal cortex (Wouterlood et al. (1990) *J. Comp. Neurol.* 296: 179–203), both of which express DNPI mRNA (FIG. 7). In the dentate gyrus, DNPI again localizes specifically to nerve terminals in the granule cell layer with VGLUT1 in other layers (FIG. 9, panels C and E). Since the granule cell layer of the dentate gyrus shows no signal for DNPI by in situ hybridization (FIG. 7, panel D), this distribution suggests a presynaptic location. Supporting this possibility, cells in the hypothalamus that project to this layer (Amaral and Witter. (1995) Pp 443–495 In:. *The Rat Nervous System, Second Edition.*, G. Paxinos, ed. (San Diego: Academic Press)) strongly express DNPI mRNA. Further, immunoperoxidase staining shows DNPI expression in nerve terminals by electron microscopy (FIG. 9, panel C).

The molecular layer of the cerebellum contains immunoreactivity for DNPI as well as VGLUT1 (FIG. 9, panels F–H). Dendrites in this layer derive predominantly from inhibitory Purkinje cells or interneurons, which do not express either DNPI or VGLUT1 mRNA. DNPI-immunoreactive puncta in the molecular layer thus most likely represent expression at nerve terminals. In particular, the DNPI antibody labels climbing fibers (FIG. 9, panel F) derived from inferior olivary neurons that express DNPI transcripts. In contrast, the VGLUT1 antibody stains parallel fibers originating from granule cells that express VGLUT1 mRNA (FIG. 9, panel H). Thus, the two major classes of synaptic input onto Purkinje cells show complementary expression of DNPI and VGLUT1. Both DNPI and VGLUT1 also localize to mossy fiber terminals in the granular layer of the cerebellum (FIG. 9, panels F and H), consistent with the origin of mossy fibers from many different brain regions.

Localization to Synaptic Vesicles

Figure 10A:
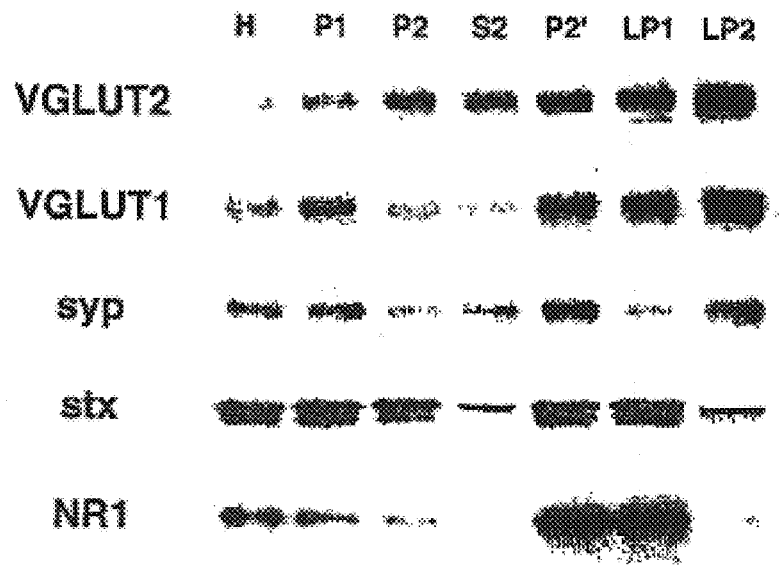
FIGS. 10A and 10B show that DNPI localizes to synaptic vesicles.

The expression of DNPI at synapses and in particular on nerve terminals suggests that it may localize to synaptic vesicles, similar to VGLUT1 (Bellocchio et al. (1998) *J. Neurosci.* 18: 8648–8659). We have therefore used biochemical fractionation of brain extracts to determine the subcellular location of DNPI. FIG. 10A shows progressive enrichment of the synaptic vesicle protein synaptophysin in the light membranes (fraction LP2) derived from hypotonic lysis of synaptosomes (Huttner et al. (1983) *J. Cell Biol.* 96: 1374–1388). Both DNPI and VGLUT1 show a similar enrichment in this fraction. In contrast, the plasma membrane protein syntaxin and a subunit of the NMDA receptor (NR1) sediment with heavy membranes released by synaptosome rupture (LP1). The localization of DNPI to LP2 thus supports specific expression on synaptic vesicles. However, relative to synaptophysin, DNPI and VGLUT1 were also detected in substantial amounts in LP1, consistent with expression on heavy membranes such as the plasma membrane in addition to synaptic vesicles (FIG. 10A). Further, DNPI shows greater localization than VGLUT1 to a population of crude membranes lighter than synaptosomes (S2).

Figure 10B:
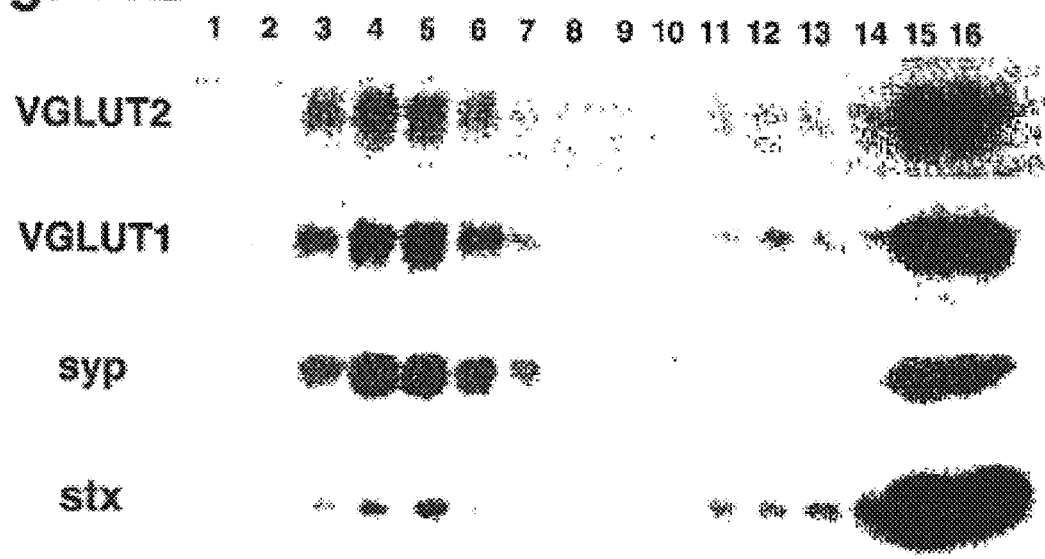

To confirm the expression of DNPI on synaptic vesicles, we have used velocity sedimentation through a glycerol gradient. This fractionation procedure separates synaptic vesicles from essentially all other membranes present in lysed synaptosomes (Clift-O'Grady et al. (1990) J. Cell Biol. 110: 1693–1703), and we find the anticipated peak of synaptophysin near the top of this gradient (FIG. 10B). Smaller amounts of synaptophysin reside in the pellet. Similarly, DNPI and VGLUT1 comigrate with synaptophysin at the top of this gradient, indicating expression on synaptic vesicles. In contrast, syntaxin appears at very low levels in these fractions relative to the bottom of the gradient, supporting expression at the plasma membrane. Although DNPI and VGLUT1 are clearly enriched in synaptic vesicles relative to syntaxin, the two related proteins also reside at higher levels on the bottom of the gradient than synaptophysin. Velocity sedimentation thus supports the results of differential centrifugation indicating expression of DNPI predominantly on synaptic vesicles, with lesser amounts on other membranes such as the plasma membrane.

Figure 11A:
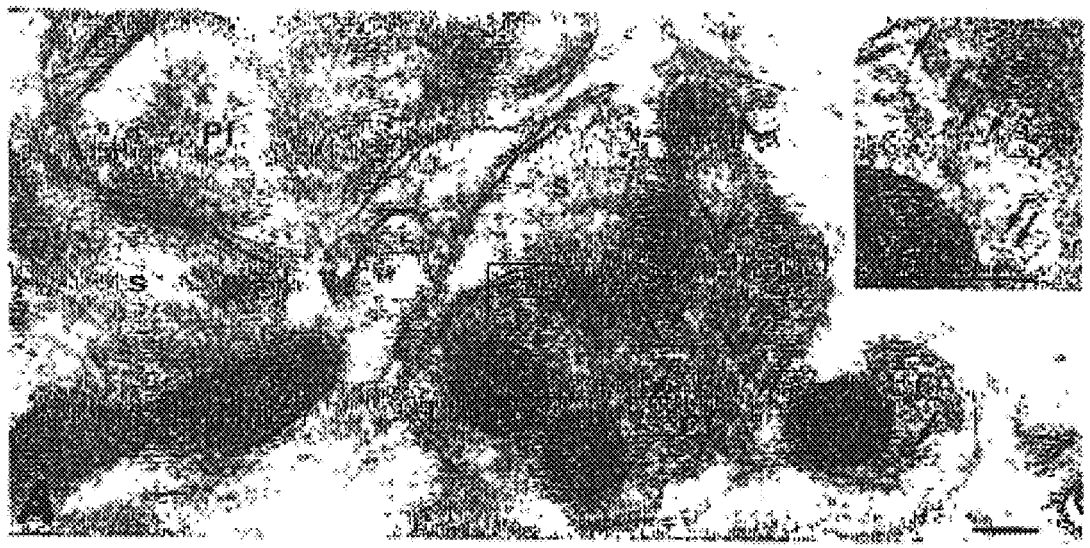
FIGS. 11A and 11B show that VGLUT1 and 2 localize to synaptic vesicles in distinct sets of excitatory nerve terminals.
Figure 11B:
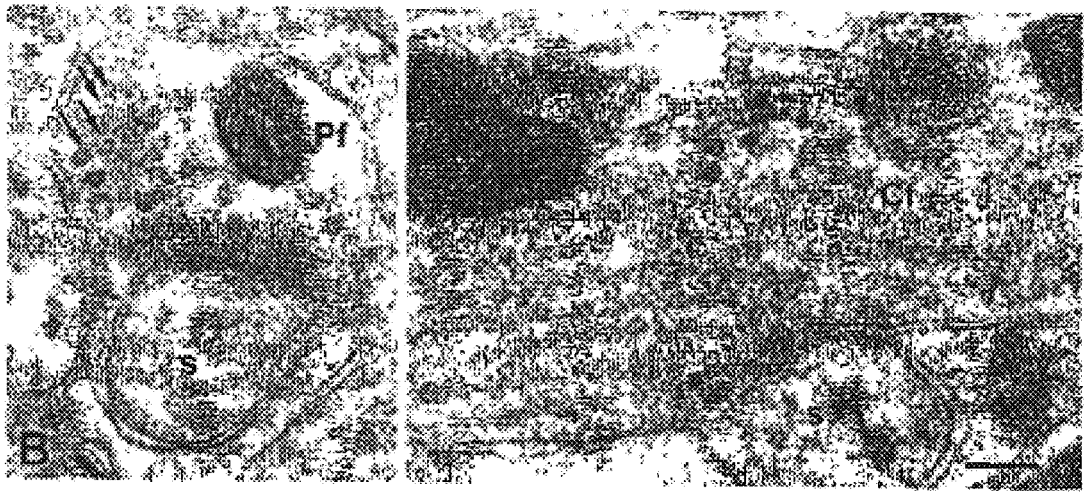

Immuno-electron microscopy confirms the biochemical analysis of DNPI localization. Labeling with gold particles in the molecular layer of the cerebellar cortex shows DNPI on the synaptic vesicles of climbing fiber boutons, with no labeling of parallel fibers (FIG. 11A). In contrast, VGLUT1 labels selectively the synaptic vesicles in parallel fibers but not those in climbing fibers (FIG. 11 B). The localization of DNPI to synaptic vesicles in specific excitatory nerve terminals suggested that DNPI might transport glutamate into synaptic vesicles, similar to VGLUT1 (see Example 1).

DNPI Transports Glutamate

Figure 12:
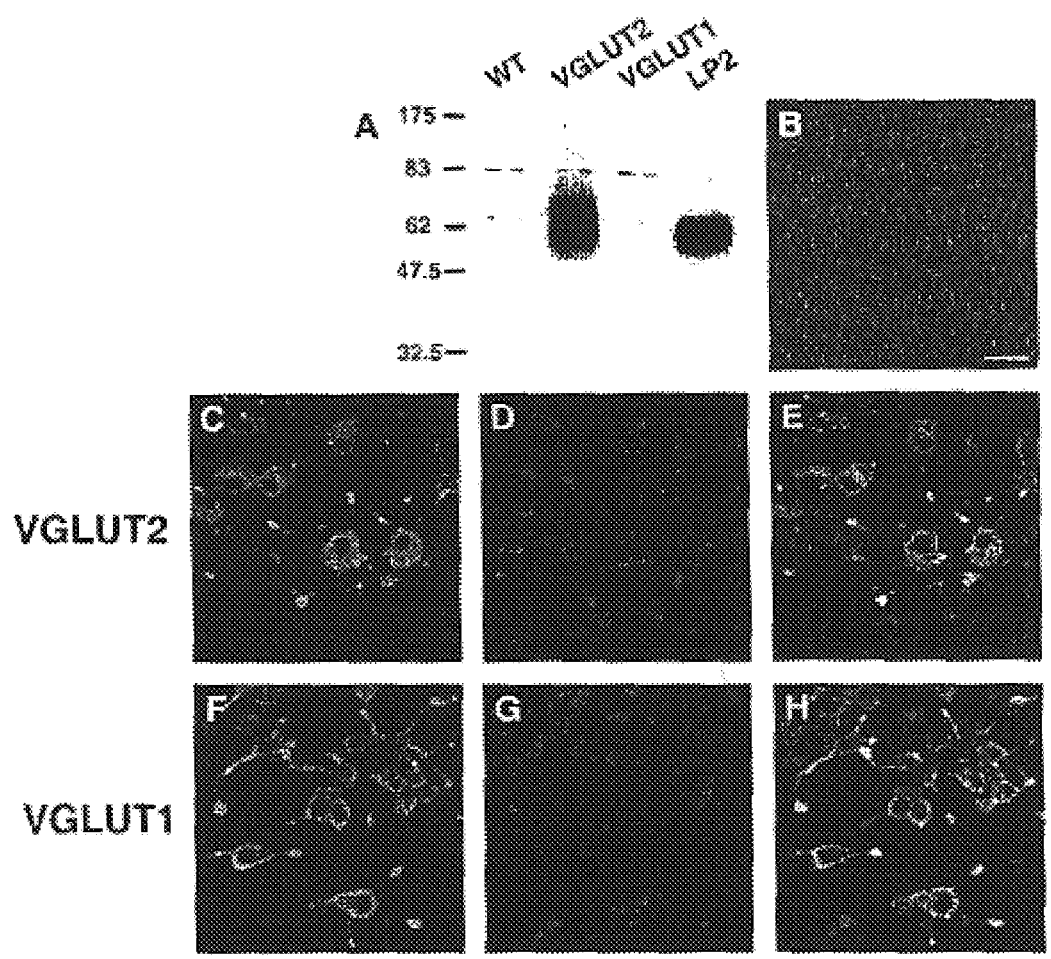
FIG. 12, panels A through H, illustrate heterologous expression of DNPI in PC12 Cells. Panel A: Western analysis of extracts prepared from untransfected (WT) PC12 cells, cells stably expressing DNPI/VGLUT2, VGLUT1 and the LP2 fraction of rat brain membranes shows that an antibody raised against the C-terminus of DNPI recognizes specifically DNPI. Panels B through H: Localization of DNPI/VGLUT2 and VGLUT1 in PC12 cells by confocal microscopy. Untransfected cells show no immunoreactivity for DNPI (panel B). Cells stably expressing DNPI and VGLUT1 were double stained with the appropriate antibody for transporter (panels C and F) and synaptophysin (panels D and G). Both DNPI and VGLUT1 colocalize with synaptophysin in processes (arrows) (overlay, panels E and H). However, they show different patterns of immunostaining within PC12 cell bodies. DNPI shows a more diffuse cytoplasmic location than VGLUT1, which has a peripheral somatic distribution (arrowheads). Scale bar=25 μm (panels E–H).

To determine whether DNPI transports glutamate into secretory vesicles, we used heterologous expression in rat pheochromocytoma PC12 cells, which exhibit no endogenous DNPI mRNA or immunoreactivity (FIGS. 12, panels A and 12B). We derived a series of transfected clones stably expressing DNPI, prepared a population of light membranes including synaptic-like microvesicles, and assayed their ability to accumulate $^3$H-glutamate. FIG. 13A shows that membranes prepared from cell clones 30 and 61 accumulate substantially more $^3$H-glutamate than untransfected cells. As anticipated, this activity does not require Na$^+$, distinguishing DNPI from plasma membrane glutamate transporters. FIG. 13B shows that the initial rate of glutamate uptake follows Michaelis-Menten kinetics and saturates with a Km 4.7±0.7 mM (n=3), slightly higher than that observed using native synaptic vesicles from the brain or VGLUT1 (Example 1, Bellocchio et al. (2000) Science 289: 957–960, Naito and Ueda (1983) J. Biol. Chem. 258: 696–699).

We also examined the substrate specificity and chloride dependence of glutamate uptake mediated by DNPI. 13C shows that L-glutamate, but not L- or D-aspartate, glycine or GABA (all 10 mM), markedly inhibits $^3$H-L-glutamate uptake by DNPI (FIG. 13C). D-glutamate and Evans Blue (4.5 $\mu$M) also inhibit uptake, as expected for a vesicular glutamate transporter (FIG. 13C), but Pi does not (data not shown). Like native synaptic vesicles and VGLUT1 (Example 1), DNPI exhibits a biphasic dependence on chloride with an optimum concentration in the same range, 2–10 mM (FIG. 13D) (Wolosker et al. (1996) J. Biol. Chem. 271, 11726–11731). In addition, dissipation of the electrical potential $\Delta\Psi$ across the vesicle membrane with the K$^+$ ionophore valinomycin inhibits $^3$H-glutamate uptake more than dissipation of the pH gradient with nigericin (FIG. 13E). DNPI thus also appears to depend on $\Delta\Psi$ to a greater extent than $\Delta$pH. However, it is clear that DNPI, like VGLUT1, depends on $\Delta$pH. Nigericin alone did not significantly reduce transport, but its addition to valinomycin essentially abolishes uptake. DNPI thus resembles VGLUT1 in transport activity.

In PC12 cells, the immunoreactivity for both DNPI and VGLUT1 is intracellular, and colocalizes with synaptophysin in processes (FIG. 12, panels C–H). However, we also observed a difference in the subcellular location of DNPI and VGLUT1. Within cell bodies, DNPI localizes diffusely throughout the cytoplasm (FIG. 12, panel C). In contrast, VGLUT1 has a more peripheral distribution, just beneath the plasma membrane (FIG. 12, panel F). We have observed this difference in multiple cell clones. Expressed in the same cells, DNPI and VGLUT1 thus appear to differ in trafficking, which may contribute to the differences in distribution observed by differential centrifugation.

Discussion

Although VGLUT1 catalyzes vesicular glutamate transport and is expressed by many excitatory neurons, many others do not express VGLUT1 (Bellocchio et al. (1998) J. Neurosci. 18: 8648–86591 Ni et al. (1994) Proc. Natl. Acad. Sci., USA, 91: 5607–5611). We now show that the closely related DNPI is expressed by excitatory neurons negative for VGLUT1. In addition, DNPI cofractionates by differential centrifugation with synaptic vesicle proteins synaptophysin and VGLUT1, cofractionates by velocity sedimentation through glycerol with synaptic vesicles, and localizes to synaptic vesicles by immunoelectron microscopy. Further, heterologous expression of DNPI confers Na$^+$-independent glutamate uptake with a Km ~5 mM and a biphasic dependence on chloride. Glutamate transport by DNPI also depends on $\Delta\Psi$ to a greater extent than $\Delta$pH. These properties resemble those previously observed for glutamate uptake by native synaptic vesicles from brain (Carlson et al. (1989) J. Biol. Chem. 264: 7369–7376; Maycox et al. (1988) J. Biol. Chem. 263: 15423–15428). Since DNPI resides on synaptic vesicles and catalyzes vesicular glutamate transport, we propose the alternative name VGLUT2.

The expression of VGLUT1 and 2 mRNA transcripts appears complementary. Unlike the isoforms of many other synaptic vesicle proteins which overlap extensively in distribution (Bajjalieh et al. (1993) Proc. Natl. Acad. Sci., USA, 90, 2150–2154; Fykse et al. (1993) J. Neurosci. 13: 4997–5000), the VGLUTs exhibit distinct, generally non-overlapping patterns of expression. Many neurons in the cortex express only VGLUT1 whereas most cells in the brainstem express only VGLUT2. In the cerebellum, the cortex expresses VGLUT1 and the deep nuclei VGLUT2. In other regions expressing both isoforms, one clearly predominates. Although most cortical layers express VGLUT1, neurons in layers IV and VI express VGLUT2. In addition, the thalamus expresses predominantly VGLUT2, but selected nuclei express low levels of VGLUT1. The complementary pattern of VGLUT1 and 2 expression appears to reflect segregated expression at the level of individual neurons. It remains to be determined whether there may also be cells that express both transcripts.

The expression of VGLUT1 and VGLUT2 accounts for the exocytotic release of glutamate by essentially all excitatory neurons. We have not observed any known population of excitatory neurons that does not express either isoform. In addition, non-glutamatergic cells do not express either VGLUT1 or 2. However, monoamine neurons have been reported to form glutamatergic autapses in culture, suggesting the expression of a vesicular glutamate transporter (Sulzer et al. (1998) *J. Neurosci.* 18: 4588–4602). Monoamine neurons may thus express a VGLUT isoform either transiently during development or after growth in vitro. Motor neurons have also been shown to exhibit quantal glutamate release after cytoplasmic loading with high concentrations of glutamate (Dan et al. (1994) *Neuron* 13: 909–917), but we have failed to detect either isoform in cranial motor nuclei. Further, we have not detected expression of VGLUT1 or 2 mRNA or protein by astrocytes, and considerable work has implicated glial cells in the exocytotic release of glutamate (Araque et al. (2000) *J. Neurosci.* 20: 666–673; Bezzi et al. (1998) *Nature* 391: 281–285; Newman and Zahs (1998) *J. Neurosci.* 18, 4022–4028). Glial cells may express VGLUT1 or VGLUT2, but at considerably lower levels that have eluded detection. Alternatively, cells not traditionally considered glutamatergic may express another, unidentified glutamate transporter.

The VGLUT proteins also appear segregated to distinct excitatory synapses. Layer IV of the cortex stains strongly for VGLUT2, consistent with the presence of afferents from thalamic nuclei expressing VGLUT2 mRNA. Layer VI also labels for VGLUT2, whereas other cortical layers stain more strongly for VGLUT1. In the thalamus, medial and intralaminar nuclei stain more heavily for VGLUT2, likely reflecting input from brainstem, hypothalamus and deep cerebellar nuclei (Cornwall and Phillipson (1988) *Neurosci.* 24: 1035–1049; Cornwall and Phillipson (1988) *Brain Res. Bull.* 21: 147–161) which express VGLUT2 mRNA. Lateral nuclei label more strongly for VGLUT1, presumably derived from cortical afferents. Strikingly complementary synaptic staining also occurs in the presubiculum, subiculum, hippocampus and cingulate cortex. Further, in the cerebellum, climbing fibers derived from the VGLUT2-positive inferior olive form synapses onto the same population of Purkinje cells contacted by parallel fibers derived from the VGLUT1-positive granule cells. Expression of the VGLUTs thus defines two populations of excitatory synapses.

Why do certain excitatory neurons express VGLUT1 and others VGLUT2? One possibility is that their distribution may simply reflect developmental history. In general, VGLUT1 appears expressed by structures derived from the telencephalon such as the cortex and hippocampus, and VGLUT2 by structures derived from the diencephalon and rhombencephalon. However, VGLUT1 also appears in the cerebellar cortex, a rhombencephalic structure, and VGLUT2 in layer IV of the cortex. Thus, the decision to express VGLUT1 or 2 does not coincide with an easily identifiable developmental event.

The complementary expression of VGLUT1 and VGLUT2 suggests distinct physiological roles in excitatory neurotransmission. However, we have not detected a clear difference in the characteristics of transport between the two isoforms. Both exhibit a similar apparent affinity for glutamate and a biphasic dependence on chloride. They both also rely predominantly on $\Delta\Psi$ but clearly depend on $\Delta pH$ as well, and both fail to recognize aspartate. VGLUT1 and 2 may thus differ in regulation rather than intrinsic transport activity.

The differential expression of VGLUT1 and VGLUT2 appears to correlate with one measurable property of synapses, the probability of transmitter release. In the cerebellum, climbing fiber synapses show an extremely high probability of release and express VGLUT2 whereas parallel fiber synapses onto the same population of Purkinje cells exhibit a lower probability of release and express VGLUT1 (Dittman and Regehr (1998) *J. Neurosci.* 18: 6147–6162). In the brainstem, sensory neurons required to relay information with high fidelity also express VGLUT2. Thalamocortical projections expressing VGLUT2 also show a higher probability of release than intracortical projections presumably expressing VGLUT1 (Gil et al. (1999) *Neuron* 23: 385–397). Hippocampal synapses, which generally express VGLUT1, show a variable but generally low probability of release (Hessler et al. (1993) *Nature* 366: 569–572; Rosenmund et al. (1993) *Science* 262: 754–757). Interestingly, the probability of transmitter release at CA1 synapses appears to decline during early postnatal development (Bolshakov and Siegelbaum (1995) *Science* 269: 1730–1734), and VGLUT1 expression upregulates dramatically during this time (Ni et al. (1995) *J. Neurosci.* 15: 5789–5799) whereas VGLUT2 remains constant (Aihara (2000) *J. Neurochem.* 74: 2622–2625). Thus, VGLUT2 appears to be expressed at synapses with a high release probability and VGLUT1 at synapses with lower probabilities of release.

How might the expression of VGLUT1 and VGLUT 2 contribute to differences in the probability of transmitter release? The results indicate that differences in trafficking may be responsible. Differential centrifugation of brain extracts shows the localization of VGLUT2 to a population of crude membranes lighter than synaptosomes. In addition, VGLUT2 has a more diffuse and VGLUT1 a more peripheral distribution in the cell bodies of PC12 cells. Even though both clearly localize to synaptic vesicles, the VGLUT proteins thus appear to differ in either the rate of internalization from the cell surface or their fate after endocytosis. The C-terminus of VGLUT1 indeed contains two polyproline motifs which are absent from VGLUT2, and the interaction of polyproline motifs in other proteins with proteins containing src homology 3 (SH3) domains has been shown to participate in synaptic vesicle recycling (Shupliakov et al. (1997) *Science* 276: 259–263). Differences in VGLUT expression may therefore contribute to the different release properties observed at different synapses.

Experimental Procedures

Molecular Cloning of DNPI/VGLUT2

A fragment of the mouse expressed sequence tag AI841371 was amplified by polymerase chain reaction (PCR) from mouse brain poly-A$^+$ mRNA and used to screen a rat brain cDNA library, resulting in the isolation of a partial cDNA clone (nucleotides 970–3982 of rat DNPI, accession number AAF76223). To reconstruct the full open reading frame, the missing segment was amplified from rat brain cDNA by PCR and ligated at a common HindIII site (nucleotide 1213). Sequence analysis on both strands confirmed the identity to rat DNPI (AAF76223).

In Situ Hybridization cDNA fragments corresponding to unique carboxy-terminal tail and 3' untranslated regions of the rat DNPI cDNA (nucleotides 2017–2358) and the rat BNPI cDNA (nucleotides 1644–2024) (31% nucleotide identity with <5 contiguous identical bases) were amplified by PCR and subcloned into the RNA expression plasmid pBluescriptII (Stratagene). $^{35}$S-labeled antisense and sense strand RNA probes were prepared by in vitro transcription of the linearized templates to a specific activity >$10^9$ cpm/$\mu$g. In situ hybridization was conducted as previously described (Fremeau et al. (1992) *Neuron* 8: 915–926) by post-fixation in 4% paraformaldehyde (PFA) of rat brain sections from 21 day old males (Sprague-Dawley) and hybridization to $^{35}$S-labeled single-stranded RNA probes in 50% formamide for 16–18 hours at 53° C. The sections were then treated with RNAse A (50 μg/ml for 60 min at 37° C.), washed at high stringency (0.1× SSC for 3 hours at 50° C.), exposed to BioMax MS film (Kodak) for 3 days, dipped in NTB2 nuclear track emulsion (Kodak) and exposed for 4–6 weeks.

Polyclonal Antibody Production

The pGEX bacterial expression system (Pharmacia Biotech) was used to produce a glutathione S-transferase (GST) fusion protein containing the carboxy-terminal 64 amino acids (residues 519–582) of rat DNPI. The 3', end of the protein-coding region (nucleotides 2017–2220) was amplified from the rat DNPI cDNA by PCR using primers (5'-GGG AAT TCA TTC ATG AAG ATG AAC TGG ATG AA-3', SEQ ID NO:10) and 5'-GGC TCG AGC TAG CTT CGT TAT GAA TAA TCA TC-3', SEQ ID NO:11) and subcloned into pGEX-5X-1 at EcoRI and XhoI sites. The fusion protein was produced in the XL1-Blue strain of *E. coil*, purified over glutathione-sepharose and used to generate polyclonal rabbit antisera (Quality Controlled Biochemicals).

Immunocytochemistry

Twenty-three day old Sprague-Dawley rats (Charles River) were anesthetized with pentobarbital, perfused with 4% PFA/PBS and the brains removed, post-fixed by immersion in 4% PFA/PBS overnight, equilibrated with 30% sucrose/PBS and frozen. Coronal sections (40 μm) were immunostained with the rabbit antibody to VGLUT2-GST after preadsorption with 20 μg/ml VGLUT1-GST. Adjacent sections were immunostained in parallel with rabbit anti-VGLUT1-GST antibody after preadsorption with 20 μg/ml VGLUT2-GST. The antibody deposits were visualized with biotinylated goat anti-rabbit secondary antibody, avidin-biotin-peroxidase (Vector) and $H_2O_2$/diaminobenzidine as described by Bellocchio et al. (1998) *J. Neurosci.* 18: 8648–8659, but without $NiSO_4$. Alternatively, brains of Wistar rats perfusion fixed with 4% PFA in 0.1 M sodium phosphate buffer pH 7.4 (or, for electron microscopy, with the addition of 0.5% glutaraldehyde) were sectioned sagittally at 40 μm by a Vibratome. The sections were processed for light and electron microscopic immunoperoxidase as described by Chaudhry et al. (1998) *J. Neurosci.* 18: 9733–9750, except that for light microscopy 0.5% Triton X-100 was included with the antibodies (prepared as above).

Post-embedding immunogold localization was performed generally as described by Chaudhry et al. (1995) *Neuron* 15: 711–720. Specifically, rats were perfused with 4% PFA+0.1% glutaraldehyde and brain tissue embedded by freeze-substitution in Lowicryl HM20. Ultrathin sections (70nm) mounted on Formvar coated nickel grids were etched on drops of fresh 1% $H_2O_2$ in ultrapure water for 0.5 h at room temperature in the dark, blocked with 5% normal goat serum+2% BSA in 0.05 M Tris-HCl pH7.6, 0.14 M NaCl, 0.01 % Triton X-100 (TBSX) for 1 h at room temperature, and incubated with the primary antibodies in the blocking solution overnight at 4° C. Anti-VGLUT1-GST was diluted 1:100, anti-VGLUT2-GST was diluted 1:500 and preadsorbed with 40 μg/ml of the other VGLUT-GST fusion protein. After rinsing in TBSX, the sections were incubated with goat anti-rabbit Fab-fragments coupled to 5 nm gold particles (British BioCell International, Cardiff, UK) diluted 1:20 in TBSX with 2% BSA for 90 min at room temperature. After rinsing, the sections were contrasted with uranyl acetate and lead citrate, and observed in a Philips CM10 electron microscope.

Subcellular Fractionation and Western Analysis

Synaptosomes were prepared from whole rat brain as described by Huttner et al. (1983) *J. Cell Biol.* 96: 1374–1388. Briefly, synaptosomes (P2) were purified by differential centrifugation and lysed by hypotonic shock to release synaptic vesicles. Heavy membranes (including the plasma membrane) were then sedimented at 33,000 g for 20 minutes (LP 1) and the supernatant (LS 1) sedimented at 251,000 g for 210 minutes to collect lighter membranes including synaptic vesicles (LP2).

Velocity sedimentation through glycerol was performed as described by Clift-O'Grady et al. (1990) *J. Cell Biol.* 110: 1693–1703. Briefly, lysed synaptosomes were sedimented through 5–25% glycerol at 195,600 g in an SW41 rotor (Beckman) for 1 hour at 4° C.

The fractions obtained by differential centrifugation or velocity sedimentation were assayed for protein content by the Bradford method (BioRad), separated by electrophoresis through SDS-acrylamide, electroblotted to nitrocellulose and immunostained as described by Bellocchio et al. (1998) *J. Neurosci.* 18: 8648–8659. VGLUT2 and VGLUT1 antibodies were used at a dilution of 1:2000 after adsorption with liver acetone powder (ICN) to reduce background. Synaptophysin was detected with a rabbit polyclonal antibody (Zymed) at 1:10,000, syntaxin with a mouse monoclonal antibody (Sigma) at 1:2000, and the NR1 subunit of the NMDA receptor (Chemicon) at 0.5 μg/ml. The immunoreactive deposits were detected by enhanced chemiluminescence (Pierce).

Heterologous Expression, Membrane Preparation and Transport Assay

PC12 cells were grown in Dulbecco's modified Eagle's medium containing 10% equine serum, 5% calf serum and transfected by electroporation with the rat DNPI/VGLUT2 cDNA subcloned in the pcDNA3 vector containing an RSV promoter (Krantz et al. (2000) *J. Cell Biol.* 149). Stable transformants were selected for resistance to the neomycin analog G418 (500 μg/ml) and screened by immunofluorescence with the DNPI antibody, resulting in the identification of two independent clones with more than 80% of the cells expressing DNPI.

For membrane preparation, untransfected and DNPI-expressing PC12 cells were grown on 15 cm plates, washed with calcium- and magnesium-free PBS, collected in 0.32 M sucrose/10 mM HEPES-KOH, pH 7.4 (SH buffer) containing protease inhibitors (2 μg/ml leupeptin, 1 μg/ml pepstatin, 1 μg/ml E64, 0.2 mM diisopropylfluorphosphate, 2 μg/ml aprotinin, and 1.25 mM MgEGTA), homogenized using a ball bearing device and the homogenate sedimented at 1000 g for 5 min to remove nuclei and debris. The supernatant was then sedimented at 27,000 g for 35 min to remove heavier membranes. The remaining light membranes including small synaptic-like microvesicles were then sedimented at 210,000 g for 1 hour. The pellet was resuspended in SH buffer with protease inhibitors at ~10 mg protein/ml.

To initiate the transport reaction, 20 μl membranes (~200 μg protein) were added to 180 μl SH buffer containing 4 mM KCl, 4 mM $MgSO_4$, 4 nM ATP, and 100 μM $^3H$-L-glutamate, with other additions noted in the text and figure legends. The reaction mixture was incubated at 29° C. for varying intervals, uptake was terminated by rapid filtration through Supor-200 membranes (Gelman) and the filters were washed rapidly four times with 1.5 ml cold 0.155 M potassium tartrate/10 mm HEPES-KOH, pH 7.4 before measuring the bound radioactivity by scintillation counting in 3 ml Cytoscint (ICN). Uptake specifically mediated by DNPI/VGLUT2 was determined by subtracting the background uptake of untransfected cell membranes from the uptake by transfected cell membranes. To examine the chloride dependence of transport, varying proportions of 0.14 M K gluconate and 0.14 M KCl were mixed in the standard reaction buffer (without sucrose) to vary the chloride concentration and maintain constant osmolarity. The ionophores nigericin and valinomycin used in FIG. 13E were prepared as 200× stock solutions in ethanol. The final ethanol concentration in the reaction mixture was 1%.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of screening for an agent that modulates the uptake of glutamate into a cell, said method comprising:
   i) contacting in vitro a cell comprising a VGLUT3 nucleic acid with a test agent; and
   ii) detecting expression or activity of said VGLUT3 where an increase or decrease in the expression or activity of said VGLUT3 as compared to a control indicates that said test agentmodulates the uptake of glutamate into the cell.

2. The method of claim 1, wherein said control is a negative control comprising contacting the cell at a lower concentration of said test agent or in the absence of said test agent.

3. The method of claim 2, wherein said lower concentration is the absence of said test agent.

4. The method of claim 1, wherein said cell is a somatic cell.

5. The method of claim 1, wherein said cell is an oocyte.

6. The method of claim 1, wherein said cell is a nerve cell.

7. The method of claim 1, wherein said cell is a vertebrate cell.

8. The method of claim 7, wherein said cell is a mammalian cell.

9. The method of claim 7, wherein said cell is a human cell.

10. The method of claim 1, wherein said detecting comprises detecting a VGLUT3 polypeptide.

11. The method of claim 10, wherein said detecting VGLUT3 polypeptide comprises a method selected from the group consisting of capillary electrophoresis, Western blot, mass spectroscopy, ELISA, immunochromatography, thin layer chromatography, and imxnunohistochemistry.

12. The method of claim 1, wherein said test agent is not an antibody.

13. The method of claim 1, wherein said test agent is not a nucleic acid.

14. The method of claim 1, wherein said test agent is not a protein.

15. The method of claim 1, wherein said test agent is a small organic molecule.

16. An isolated cell comprising a heterologous nucleic acid encoding a glutamate transporter wherein said glutamate transporter is VGLUT3.

17. The cell of claim 16, wherein said cell is a mammalian cell.

18. The cell of claim 16, wherein said cell is a somatic cell.

19. The cell of claim 16, wherein said cell is an oocyte or a nerve cell.

20. The cell of claim 16, wherein said cell transports glutamate via said glutamate transporter.

21. The cell of claim 16, wherein said cell is a pheochromocytoma PC12 cell.

* * * * *

SEQUENCE LISTING

```
<160> NUMBER OF SEQ ID NOS: 11

<210> SEQ ID NO 1
<211> LENGTH: 2607
<212> TYPE: DNA
<213> ORGANISM: Homo sapiens
<220> FEATURE:
<221> NAME/KEY: misc_feature
<223> OTHER INFORMATION: n is a, g, c, or t

<400> SEQUENCE: 1
tgtgctctaa agcccccatt caaaatgcca tttaacgcat ttgataccctt caaagaaaaa      60 attttgaaac ccgggaagga aggagtgaag aatgccgtag gagattcgct ggggatctta     120
caaagaaaac tcgatgggac caacgaggag ggagatgcca ttgagctgag tgaggaagga     180
aggcctgtgc agacatccag agcccgagcc cctgtgtgcg actgcagctg ctgtggcatc     240
cccaagcggt acatcatcgc tgtcatgagt ggcctgggat tctgcatttc ctttgggatt     300
cggtgcaacc ttggagtggc cattgtgaaa atggtcaaca atagcactgt gtatgtggat     360
gggaaaccgg aaatccagac agcacagttt aactgggatc cagagacggt gggaagggcg     420
aattctctta tccatggatc tttttttctgg ggttatattg tgacacaaat tcccggtggc     480
ttcatttcaa acaagtttgc tgctaacagg gtctttggag ctgccatctt cttgacgtca     540
accctgaaca tgttcatccc ttccgcggcc agggtgcatt acggctgtgt catgtgtgtg     600
aggattttgc agggtctggt ggagggtgtg acctacccag cctgccacgg gatgtggagt     660
aagtgggcac ctcccctgga gagaagtcgt ctagccacaa cctcttttg tggttcctat     720 gccggggcag tcgttgctat gccccttgca ggagtattgg tgcagtacat tggctgggcc     780 tctgccttt ataatttacgg gatgtttgga attatttggt acatgttttg gctgctgctg     840
caggcttatg agtgtccagc agttcaccca acaatatcca atgaagaacg gacctacata     900
gagacaagta taggagaagg cgccaacttg gccagtctga gcaaattcaa cacaccatgg     960
agaaggtttt tcacatcctt gcctgtctat gccattattg tggcaaactt ttgtagaagc    1020
tggaccttct atttgctctt aataagtcag cctgcttact ttgaagaggt cttttgggttt    1080 gcaataagta aggtgggtct cttgtcagct gtcccacaca tggtgatgac aatcgtggta    1140
cccattggag gacaactggc tgattattta agaagccgaa agattttgac cacaactgct    1200
gtcagaaaga tcatgaattg tggaggctttt ggcatggagg caaccttgct cctggtggtt    1260
gggttttccc ataccaaagg agtggctatc tccttcctgg tgcttgctgt aggattagt    1320 ggcttttgcaa tttcaggttt caatgtcaac cacctggaca ttgctccacg atatgccagc    1380
atcctcatgg ggatctcaaa tggcgtggga accctctctg gaatggtttg tccctcatt    1440 gttggtgcaa tgacaaagca caagacccgg gaagaatggc agaatgtgtt cctcatagca    1500
gccctggtgc actacagtgg agtcatcttc tacgggggtct ttgcttctgg ggaaaacag    1560 gactgggctg atccagagaa tctctctgag gagaaatgtg gaatcattga ccaagatgaa    1620
```

-continued

```
ttagccgagg aaacagaact caaccacgag gctttcgtaa gtcccagaaa gaagatgtct    1680
tatggagcca ccacccagaa ttgtgaggtc cagaagacgg atcggagaca acagagagaa    1740
tccgccttcg aggggagga gccattatcc taccagaatg aagaggactt ttcagaaaca     1800
tcttaacgtg catcttcccc tcagcttaca accagaagtc tccacaccca ttgcttttcc    1860
cataccttgg ccttccaggg ggccaaatca caggaaggg ggagactaaa tcaacaacag     1920
agaagaaaaa tgccttctta caaagatggg cgtatggatc ttggtctcag ttaattagat    1980
agttgatcat atttttttg ggggggcaa ttgggcattg gctgttgagc cttctctcaa      2040
aagaacaatt tattcaggaa gaaatggcta aagaataag gagtggcttg ttgctcaaat     2100
aaacactgaa gaaatccctc tttggtctgg agaagagtac atggtggttg ccaccccatc    2160
tccaaggata tccatgtaga ggacaatctc tgcaacctaa tgaagggaat cactcatggg    2220
ggcccttggt tgtgccaggt gctttatgaa cattcttatt taactcccac accctaatat    2280
agttattgta cccattttac aactaagaac attaaatgac taggttggcc cacccaaggt    2340
tgtcctctca gagccaaagc tgagactggc agatgaccag gagttttagg aaggaaggaa    2400
ggaaggaagg aaggaaggaa ggaaggaagg aaggaaggaa ggaagggttc agttgagtgt    2460
agggtcattt tcaatgacaa aaacaaaaac tggaatcagt tggtttgtgg gtaattccat    2520
gtttggtcaa gggtgtgtgc atgcaaacgt gtatgtgcgt gtgtgtgtgt ttgtgtgttt    2580
gngtgtnagn nngnatnana anaaaan                                        2607
```

<210> SEQ ID NO 2
<211> LENGTH: 2607
<212> TYPE: DNA
<213> ORGANISM: Homo sapiens
<220> FEATURE:
<221> NAME/KEY: misc_feature
<223> OTHER INFORMATION: n is a, c, g, or t

<400> SEQUENCE: 2

```
acacgagatt tcgggggtaa gttttacggt aaattgcgta aactatggaa gtttcttttt    60 taaactttg ggcccttcct tcctcacttc ttacggcatc ctctaagcga ccctagaat     120 gtttcttttg agctaccctg gttgctcctc cctctacggt aactcgactc actccttcct   180
tccggacacg tctgtaggtc tcgggctcgg ggacacacgc tgacgtcgac gacaccgtag   240
gggttcgcca tgtagtagcg acagtactca ccggaccta agacgtaaag gaaaccctaa    300
gccacgttgg aacctcaccg gtaacacctt taccagttgt tatcgtgaca catacaccta   360 cccctttggcc tttaggtctg tcgtgtcaaa ttgaccctag gtctctgcca cccttcccgc   420
ttaagagaat aggtacctag aaaaaagacc ccaatataac actgtgttta agggccaccg    480
aagtaaagtt tgttcaaacg acgattgtcc cagaaacctc gacggtagaa gaactgcagt    540
tgggacttgt acaagtaggg aaggcgccgg tcccacgtaa tgccgacaca gtacacacac    600
tcctaaaacg tcccagacca cctcccacac tggatgggtc ggacggtgcc ctacacctca   660
ttcacccgtg gagggacct ctcttcagca gatcggtgtt ggagaaaaac accaaggata    720
cggccccgtc agcaacgata cggggaacgt cctcataacc acgtcatgta accgacccgg    780
agacggaaaa tataaatgcc ctacaaacct taataaacca tgtacaaaac cgacgacgac    840
gtccgaatac tcacaggtcg tcaagtgggt tgttataggt tacttcttgc ctggatgtat    900
ctctgttcat atcctcttcc gcggttgaac cggtcagact cgtttaagtt gtgtggtacc    960
tcttccaaaa agtgtaggaa cggacagata cggtaataac accgtttgaa aacatcttcg    1020
```

```
acctggaaga taaacgagaa ttattcagtc ggacgaatga aacttctcca gaaacccaaa   1080
cgttattcat tccacccaga gaacagtcga cagggtgtgt accactactg ttagcaccat   1140
gggtaacctc ctgttgaccg actaataaat tcttcggctt tctaaaactg gtgttgacga   1200
cagtctttct agtacttaac acctccgaaa ccgtacctcc gttggaacga ggaccaccaa   1260
cccaaaaggg tatggtttcc tcaccgatag aggaaggacc acgaacgaca tcctaaatca   1320
ccgaaacgtt aaagtccaaa gttacagttg gtggacctgt aacgaggtgc tatacggtcg   1380
taggagtacc cctagagttt accgcaccct tgggagagac cttaccaaac aggggagtaa   1440
caaccacgtt actgtttcgt gttctgggcc cttcttaccg tcttacacaa ggagtatcgt   1500
cgggaccacg tgatgtcacc tcagtagaag atgccccaga aacgaagacc ccttttgtc   1560 ctgacccgac taggtctctt agagagactc ctctttacac cttagtaact ggttctactt   1620
aatcggctcc tttgtcttga gttggtgctc cgaaagcatt cagggtcttt cttctacaga   1680 ataccgtcggt ggtgggtctt aacactccag gtcttctgcc tagcctctgt tgtctctctt   1740
aggcggaagc tcccctcct cggtaatagg atggtcttac ttctcctgaa agtctttgt   1800 agaattgcac gtagaagggg agtcgaatgt tggtcttcag aggtgtgggt aacgaaaagg   1860
gtatggaacc ggaaggtccc ccggtttagt gtcctttccc cctctgattt agttgttgtc   1920
tcttcttttt acggaagaat gtttctaccc gcataccag aaccagagtc aattaatcta   1980
tcaactagta taaaaaaac ccccccgtt aacccgtaac cgacaactcg aagagagtt   2040 ttcttgttaa ataagtcctt cttaccgat cttcttattc ctcaccgaac aacgagttta   2100
tttgtgactt ctttagggag aaaccagacc tcttctcatg taccaccaac ggtggggtag   2160
aggttcctat agtacatct cctgttagag acgttggatt acttcccta gtgagtaccc   2220 ccgggaacca acacggtcca cgaaatactt gtaagaataa attgagggtg tgggattata   2280
tcaataacat gggtaaaatg ttgattcttg taatttactg atccaaccgg gtgggttcca   2340
acaggagagt ctcggtttcg actctgaccg tctactggtc ctcaaaatcc ttccttcctt   2400
ccttccttcc ttccttcctt ccttccttcc ttccttcctt cctccaag tcaactcaca   2460 tcccagtaaa agttactgtt tttgttttg accttagtca accaaacacc cattaaggta   2520
caaaccagtt cccacacacg tacgtttgca catacacgca cacacacaca aacacacaaa   2580
cncacantcn nncntantnt tnttttn                                      2607
```

<210> SEQ ID NO 3
<211> LENGTH: 850
<212> TYPE: PRT
<213> ORGANISM: Homo sapiens

<400> SEQUENCE: 3

```
Cys Ala Leu Lys Pro Pro Phe Lys Met Pro Phe Asn Ala Phe Asp Thr
1               5                  10                  15

Phe Lys Glu Lys Ile Leu Lys Pro Gly Lys Glu Gly Val Lys Asn Ala
            20                  25                  30

Val Gly Asp Ser Leu Gly Ile Leu Gln Arg Lys Leu Asp Gly Thr Asn
        35                  40                  45

Glu Glu Gly Asp Ala Ile Glu Leu Ser Glu Glu Gly Arg Pro Val Gln
    50                  55                  60

Thr Ser Arg Ala Arg Ala Pro Val Cys Asp Cys Ser Cys Gly Ile
65                  70                  75                  80

Pro Lys Arg Tyr Ile Ile Ala Val Met Ser Gly Leu Gly Phe Cys Ile
```

```
                    85                  90                  95
Ser Phe Gly Ile Arg Cys Asn Leu Gly Val Ala Ile Val Glu Met Val
               100                 105                 110

Asn Asn Ser Thr Val Tyr Val Asp Gly Lys Pro Glu Ile Gln Thr Ala
               115                 120                 125

Gln Phe Asn Trp Asp Pro Glu Thr Val Gly Arg Ala Asn Ser Leu Ile
               130                 135                 140

His Gly Ser Phe Phe Trp Gly Tyr Ile Val Thr Gln Ile Pro Gly Gly
145                           150                 155                 160

Phe Ile Ser Asn Lys Phe Ala Ala Asn Arg Val Phe Gly Ala Ala Ile
               165                 170                 175

Phe Leu Thr Ser Thr Leu Asn Met Phe Ile Pro Ser Ala Ala Arg Val
               180                 185                 190

His Tyr Gly Cys Val Met Cys Val Arg Ile Leu Gln Gly Leu Val Glu
               195                 200                 205

Gly Val Thr Tyr Pro Ala Cys His Gly Met Trp Ser Lys Trp Ala Pro
               210                 215                 220

Pro Leu Glu Arg Ser Arg Leu Ala Thr Thr Ser Phe Cys Gly Ser Tyr
225                           230                 235                 240

Ala Gly Ala Val Val Ala Met Pro Leu Ala Gly Val Leu Val Gln Tyr
               245                 250                 255

Ile Gly Trp Ala Ser Ala Phe Tyr Ile Tyr Gly Met Phe Gly Ile Ile
               260                 265                 270

Trp Tyr Met Phe Trp Leu Leu Leu Gln Ala Tyr Glu Cys Pro Ala Val
               275                 280                 285

His Pro Thr Ile Ser Asn Glu Glu Arg Thr Tyr Ile Glu Thr Ser Ile
               290                 295                 300

Gly Glu Gly Ala Asn Leu Ala Ser Leu Ser Lys Phe Asn Thr Pro Trp
305                           310                 315                 320

Arg Arg Phe Phe Thr Ser Leu Pro Val Tyr Ala Ile Ile Val Ala Asn
               325                 330                 335

Phe Cys Arg Ser Trp Thr Phe Tyr Leu Leu Leu Ile Ser Gln Pro Ala
               340                 345                 350

Tyr Phe Glu Glu Val Phe Gly Phe Ala Ile Ser Lys Val Gly Leu Leu
               355                 360                 365

Ser Ala Val Pro His Met Val Met Thr Ile Val Val Pro Ile Gly Gly
               370                 375                 380

Gln Leu Ala Asp Tyr Leu Arg Ser Arg Lys Ile Leu Thr Thr Thr Ala
385                           390                 395                 400

Val Arg Lys Ile Met Asn Cys Gly Gly Phe Gly Met Glu Ala Thr Leu
               405                 410                 415

Leu Leu Val Val Gly Phe Ser His Thr Lys Gly Val Ala Ile Ser Phe
               420                 425                 430

Leu Val Leu Ala Val Gly Phe Ser Gly Phe Ala Ile Ser Gly Phe Asn
               435                 440                 445

Val Asn His Leu Asp Ile Ala Pro Arg Tyr Ala Ser Ile Leu Met Gly
               450                 455                 460

Ile Ser Asn Gly Val Gly Thr Leu Ser Gly Met Val Cys Pro Leu Ile
465                           470                 475                 480

Val Gly Ala Met Thr Lys His Lys Thr Arg Glu Glu Trp Gln Asn Val
               485                 490                 495

Phe Leu Ile Ala Ala Leu Val His Tyr Ser Gly Val Ile Phe Tyr Gly
               500                 505                 510
```

```
Val Phe Ala Ser Gly Glu Lys Gln Asp Trp Ala Asp Pro Glu Asn Leu
            515                 520                 525

Ser Glu Glu Lys Cys Gly Ile Ile Asp Gln Asp Glu Leu Ala Glu Glu
        530                 535                 540

Thr Glu Leu Asn His Glu Ala Phe Val Ser Pro Arg Lys Lys Met Ser
545                 550                 555                 560

Tyr Gly Ala Thr Thr Gln Asn Cys Glu Val Gln Lys Thr Asp Arg Arg
                565                 570                 575

Gln Gln Arg Glu Ser Ala Phe Glu Gly Glu Pro Leu Ser Tyr Gln
            580                 585                 590

Asn Glu Glu Asp Phe Ser Glu Thr Ser Arg Ala Ser Ser Pro Gln Leu
                595                 600                 605

Thr Thr Arg Ser Leu His Thr His Cys Phe Ser His Thr Leu Ala Phe
            610                 615                 620

Gln Gly Ala Lys Ser Gln Glu Arg Gly Arg Leu Asn Gln Gln Gln Arg
625                 630                 635                 640

Arg Lys Met Pro Ser Tyr Lys Asp Gly Arg Met Asp Leu Gly Leu Ser
                645                 650                 655

Leu Asp Ser Ser Tyr Phe Phe Trp Gly Gly Gln Leu Gly Ile Gly Cys
                660                 665                 670

Ala Phe Ser Gln Lys Asn Asn Leu Phe Arg Lys Lys Trp Leu Glu Glu
            675                 680                 685

Gly Val Ala Cys Cys Ser Asn Lys His Arg Asn Pro Ser Leu Val Trp
            690                 695                 700

Arg Arg Val His Gly Gly Cys His Pro Ile Ser Lys Asp Ile His Val
705                 710                 715                 720

Glu Asp Asn Leu Cys Asn Leu Met Lys Gly Ile Thr His Gly Gly Pro
                725                 730                 735

Trp Leu Cys Gln Val Leu Tyr Glu His Ser Tyr Leu Thr Pro Thr Pro
                740                 745                 750

Tyr Ser Tyr Cys Thr His Phe Thr Thr Lys Asn Ile Lys Leu Gly Trp
            755                 760                 765

Pro Thr Gln Gly Cys Pro Leu Arg Ala Lys Ala Glu Thr Gly Arg Pro
            770                 775                 780

Gly Val Leu Gly Arg Lys Glu Gly Arg Lys Glu Gly Arg Lys Glu Gly
785                 790                 795                 800

Arg Lys Glu Gly Arg Lys Gly Ser Val Glu Cys Arg Val Ile Phe Asn
                805                 810                 815

Asp Lys Asn Lys Asn Trp Asn Gln Leu Val Cys Gly Phe His Val Trp
            820                 825                 830

Ser Arg Val Cys Ala Cys Lys Arg Val Cys Ala Cys Val Cys
            835                 840                 845

Val Phe
    850

<210> SEQ ID NO 4
<211> LENGTH: 582
<212> TYPE: PRT
<213> ORGANISM: Rattus rattus

<400> SEQUENCE: 4

Met Glu Ser Val Lys Gln Arg Ile Leu Ala Pro Gly Lys Glu Gly Ile
1               5                   10                  15

Lys Asn Phe Ala Gly Lys Ser Leu Gly Gln Ile Tyr Arg Val Leu Glu
```

-continued

```
               20                  25                  30
Lys Lys Gln Asp Asn Arg Glu Thr Ile Glu Leu Thr Glu Asp Gly Lys
         35                  40                  45
Pro Leu Glu Val Pro Glu Lys Lys Ala Pro Leu Cys Asp Cys Thr Cys
     50                  55                  60
Phe Gly Leu Pro Arg Arg Tyr Ile Ile Ala Ile Met Ser Gly Leu Gly
 65                  70                  75                  80
Phe Cys Ile Ser Phe Gly Ile Arg Cys Asn Leu Gly Val Ala Ile Val
                 85                  90                  95
Asp Met Val Asn Asn Ser Thr Ile His Arg Gly Gly Lys Val Ile Lys
             100                 105                 110
Glu Lys Ala Lys Phe Asn Trp Asp Pro Glu Thr Val Gly Met Ile His
         115                 120                 125
Gly Ser Phe Phe Trp Gly Tyr Ile Ile Thr Gln Ile Pro Gly Gly Tyr
     130                 135                 140
Ile Ala Ser Arg Leu Ala Ala Asn Arg Val Phe Gly Ala Ala Ile Leu
145                 150                 155                 160
Leu Thr Ser Thr Leu Asn Met Leu Ile Pro Ser Ala Ala Arg Val His
                 165                 170                 175
Tyr Gly Cys Val Ile Phe Val Arg Ile Leu Gln Gly Leu Val Glu Gly
             180                 185                 190
Val Thr Tyr Pro Ala Cys His Gly Ile Trp Ser Lys Trp Ala Pro Pro
         195                 200                 205
Leu Glu Arg Ser Arg Leu Ala Thr Thr Ser Phe Cys Gly Ser Tyr Ala
     210                 215                 220
Gly Ala Val Ile Ala Met Pro Leu Ala Gly Ile Leu Val Gln Tyr Thr
225                 230                 235                 240
Gly Trp Ser Ser Val Phe Tyr Val Tyr Gly Ser Phe Gly Met Val Trp
                 245                 250                 255
Tyr Met Phe Trp Leu Leu Val Ser Tyr Glu Ser Pro Ala Lys His Pro
             260                 265                 270
Thr Ile Thr Asp Glu Glu Arg Arg Tyr Ile Glu Glu Ser Ile Gly Glu
         275                 280                 285
Ser Ala Asn Leu Leu Gly Ala Met Glu Lys Phe Lys Thr Pro Trp Arg
     290                 295                 300
Lys Phe Phe Thr Ser Met Pro Val Tyr Ala Ile Ile Val Ala Asn Phe
305                 310                 315                 320
Cys Arg Ser Trp Thr Phe Tyr Leu Leu Leu Ile Ser Gln Pro Ala Tyr
                 325                 330                 335
Phe Glu Glu Val Phe Gly Phe Glu Ile Ser Lys Val Gly Met Leu Ser
             340                 345                 350
Ala Val Pro His Leu Val Met Thr Ile Ile Val Pro Ile Gly Gly Gln
         355                 360                 365
Ile Ala Asp Phe Leu Arg Ser Lys Gln Ile Leu Ser Thr Thr Thr Val
     370                 375                 380
Arg Lys Ile Met Asn Cys Gly Gly Phe Gly Met Glu Ala Thr Leu Leu
385                 390                 395                 400
Leu Val Val Gly Tyr Ser His Thr Arg Gly Val Ala Ile Ser Phe Leu
                 405                 410                 415
Val Leu Ala Val Gly Phe Ser Gly Phe Ala Ile Ser Gly Phe Asn Val
             420                 425                 430
Asn His Leu Asp Ile Ala Pro Arg Tyr Ala Ser Ile Leu Met Gly Ile
         435                 440                 445
```

-continued

```
Ser Asn Gly Val Gly Thr Leu Ser Gly Met Val Cys Pro Ile Ile Val
    450                 455                 460
Gly Ala Met Thr Lys Asn Lys Ser Arg Glu Glu Trp Gln Tyr Val Phe
465                 470                 475                 480
Leu Ile Ala Ala Leu Val His Tyr Gly Gly Val Ile Phe Tyr Ala Leu
                485                 490                 495
Phe Ala Ser Gly Glu Lys Gln Pro Trp Ala Asp Pro Glu Glu Thr Ser
            500                 505                 510
Glu Glu Lys Cys Gly Phe Ile His Glu Asp Glu Leu Asp Glu Glu Thr
            515                 520                 525
Gly Asp Ile Thr Gln Asn Tyr Ile Asn Tyr Gly Thr Thr Lys Ser Tyr
    530                 535                 540
Gly Ala Thr Ser Gln Glu Asn Gly Gly Trp Pro Asn Gly Trp Glu Lys
545                 550                 555                 560
Lys Glu Glu Phe Val Gln Glu Ser Ala Gln Asp Ala Tyr Ser Tyr Lys
                565                 570                 575
Asp Arg Asp Asp Tyr Ser
            580

<210> SEQ ID NO 5
<211> LENGTH: 560
<212> TYPE: PRT
<213> ORGANISM: Rattus rattus

<400> SEQUENCE: 5

Met Glu Phe Arg Gln Glu Glu Phe Arg Lys Leu Ala Gly Arg Ala Leu
1               5                   10                  15
Gly Arg Leu His Arg Leu Leu Glu Lys Arg Gln Glu Gly Ala Glu Thr
            20                  25                  30
Leu Glu Leu Ser Ala Asp Gly Arg Pro Val Thr Thr His Thr Arg Asp
        35                  40                  45
Pro Pro Val Val Asp Cys Thr Cys Phe Gly Leu Pro Arg Arg Tyr Ile
    50                  55                  60
Ile Ala Ile Met Ser Gly Leu Gly Phe Cys Ile Ser Phe Gly Ile Arg
65                  70                  75                  80
Cys Asn Leu Gly Val Ala Ile Val Ser Met Val Asn Asn Ser Thr Thr
                85                  90                  95
His Arg Gly Gly His Val Val Gln Lys Ala Gln Phe Asn Trp Asp
            100                 105                 110
Pro Glu Thr Val Gly Leu Ile His Gly Ser Phe Phe Trp Gly Tyr Ile
        115                 120                 125
Val Thr Gln Ile Pro Gly Gly Phe Ile Cys Gln Lys Phe Ala Ala Asn
    130                 135                 140
Arg Val Phe Gly Phe Ala Ile Val Ala Thr Ser Thr Leu Asn Met Leu
145                 150                 155                 160
Ile Pro Ser Ala Ala Arg Val His Tyr Gly Cys Val Ile Phe Val Arg
                165                 170                 175
Ile Leu Gln Gly Leu Val Glu Gly Val Thr Tyr Pro Ala Cys His Gly
            180                 185                 190
Ile Trp Ser Lys Trp Ala Pro Pro Leu Glu Arg Ser Arg Leu Ala Thr
        195                 200                 205
Thr Ala Phe Cys Gly Ser Tyr Ala Gly Ala Val Val Ala Met Pro Leu
    210                 215                 220
Ala Gly Val Leu Val Gln Tyr Ser Gly Trp Ser Ser Val Phe Tyr Val
```

-continued

```
                225                 230                 235                 240
Tyr Gly Ser Phe Gly Ile Phe Trp Tyr Leu Phe Trp Leu Leu Val Ser
                    245                 250                 255
Tyr Glu Ser Pro Ala Leu His Pro Ser Ile Ser Glu Glu Arg Lys
            260                 265                 270
Tyr Ile Glu Asp Ala Ile Gly Glu Ser Ala Lys Leu Met Asn Pro Val
            275                 280                 285
Thr Lys Phe Asn Thr Pro Trp Arg Arg Phe Phe Thr Ser Met Pro Val
        290                 295                 300
Tyr Ala Ile Ile Val Ala Asn Phe Cys Arg Ser Trp Thr Phe Tyr Leu
305                 310                 315                 320
Leu Leu Ile Ser Gln Pro Ala Tyr Phe Glu Glu Val Phe Gly Phe Glu
                    325                 330                 335
Ile Ser Lys Val Gly Leu Val Ser Ala Leu Pro His Leu Val Met Thr
                340                 345                 350
Ile Ile Val Pro Ile Gly Gly Gln Ile Ala Asp Phe Leu Arg Ser Arg
                355                 360                 365
His Ile Met Ser Thr Thr Asn Val Arg Lys Leu Met Asn Cys Gly Gly
    370                 375                 380
Phe Gly Met Glu Ala Thr Leu Leu Leu Val Val Gly Tyr Ser His Ser
385                 390                 395                 400
Lys Gly Val Ala Ile Ser Phe Leu Val Leu Ala Val Gly Phe Ser Gly
                405                 410                 415
Phe Ala Ile Ser Gly Phe Asn Val Asn His Leu Asp Ile Ala Pro Arg
                420                 425                 430
Tyr Ala Ser Ile Leu Met Gly Ile Ser Asn Gly Val Gly Thr Leu Ser
                435                 440                 445
Gly Met Val Cys Pro Ile Ile Val Gly Ala Met Thr Lys His Lys Thr
        450                 455                 460
Arg Glu Glu Trp Gln Tyr Val Phe Leu Ile Ala Ser Leu Val His Tyr
465                 470                 475                 480
Gly Gly Val Ile Phe Tyr Gly Val Phe Ala Ser Gly Glu Lys Gln Pro
                485                 490                 495
Trp Ala Glu Pro Glu Glu Met Ser Glu Glu Lys Cys Gly Phe Val Gly
            500                 505                 510
His Asp Gln Leu Ala Gly Ser Asp Glu Ser Glu Met Glu Asp Glu Val
        515                 520                 525
Glu Pro Pro Gly Ala Pro Ala Pro Pro Ser Tyr Gly Ala Thr
    530                 535                 540
His Ser Thr Val Gln Pro Pro Arg Pro Pro Pro Val Arg Asp Tyr
545                 550                 555                 560
```

<210> SEQ ID NO 6
<211> LENGTH: 563
<212> TYPE: PRT
<213> ORGANISM: Caenorhabditis elegans

<400> SEQUENCE: 6

```
Met Val Gly Glu Pro Leu Ala Lys Met Thr Ala Ala Ala Ser Ala
1               5                   10                  15
Thr Gly Ala Ala Pro Pro Gln Gln Met Gln Glu Glu Gly Asn Glu Asn
            20                  25                  30
Pro Met Gln Met His Ser Asn Lys Val Leu Gln Val Met Glu Gln Thr
        35                  40                  45
```

```
Trp Ile Gly Lys Cys Arg Lys Arg Trp Leu Leu Ala Ile Leu Ala Asn
 50                  55                  60

Met Gly Phe Met Ile Ser Phe Gly Ile Arg Cys Asn Phe Gly Ala Ala
 65                  70                  75                  80

Lys Thr His Met Tyr Lys Asn Tyr Thr Asp Pro Tyr Gly Lys Val His
                 85                  90                  95

Met His Glu Phe Asn Trp Thr Ile Asp Glu Leu Ser Val Met Glu Ser
            100                 105                 110

Ser Tyr Phe Tyr Gly Tyr Leu Val Thr Gln Ile Pro Ala Gly Phe Leu
        115                 120                 125

Ala Ala Lys Phe Pro Pro Asn Lys Leu Phe Gly Phe Gly Ile Gly Val
130                 135                 140

Gly Ala Phe Leu Asn Ile Leu Leu Pro Tyr Gly Phe Lys Val Lys Ser
145                 150                 155                 160

Asp Tyr Leu Val Ala Phe Ile Gln Ile Thr Gln Gly Leu Val Gln Gly
                165                 170                 175

Val Cys Tyr Pro Ala Met His Gly Val Trp Arg Tyr Trp Ala Pro Pro
            180                 185                 190

Met Glu Arg Ser Lys Leu Ala Thr Thr Ala Phe Thr Gly Ser Tyr Ala
        195                 200                 205

Gly Ala Val Leu Gly Leu Pro Leu Ser Ala Phe Leu Val Ser Tyr Val
210                 215                 220

Ser Trp Ala Ala Pro Phe Tyr Leu Tyr Gly Val Cys Gly Val Ile Trp
225                 230                 235                 240

Ala Ile Leu Trp Phe Cys Val Thr Phe Glu Lys Pro Ala Phe His Pro
                245                 250                 255

Thr Ile Ser Gln Glu Glu Lys Ile Phe Ile Glu Asp Ala Ile Gly His
            260                 265                 270

Val Ser Asn Thr His Pro Thr Ile Arg Ser Ile Pro Trp Lys Ala Ile
        275                 280                 285

Val Thr Ser Lys Pro Val Trp Ala Ile Ile Val Ala Asn Phe Ala Arg
290                 295                 300

Ser Trp Thr Phe Tyr Leu Leu Leu Gln Asn Gln Leu Thr Tyr Met Lys
305                 310                 315                 320

Glu Ala Leu Gly Met Lys Ile Ala Asp Ser Gly Leu Leu Ala Ala Ile
                325                 330                 335

Pro His Leu Val Met Gly Cys Val Val Leu Met Gly Gly Gln Leu Ala
            340                 345                 350

Asp Tyr Leu Arg Ser Asn Lys Ile Leu Ser Thr Thr Ala Val Arg Lys
        355                 360                 365

Ile Phe Asn Cys Gly Gly Phe Gly Gly Glu Ala Ala Phe Met Leu Ile
370                 375                 380

Val Ala Tyr Thr Thr Ser Asp Thr Thr Ala Ile Met Ala Leu Ile Ala
385                 390                 395                 400

Ala Val Gly Met Ser Gly Phe Ala Ile Ser Gly Phe Asn Val Asn His
                405                 410                 415

Leu Asp Ile Ala Pro Arg Tyr Ala Ala Ile Leu Met Gly Phe Ser Asn
            420                 425                 430

Gly Ile Gly Thr Leu Ala Gly Leu Thr Cys Pro Phe Val Thr Glu Ala
        435                 440                 445

Phe Thr Ala His Ser Lys His Gly Trp Thr Ser Val Phe Leu Leu Ala
450                 455                 460

Ser Leu Ile His Phe Thr Gly Val Thr Phe Tyr Ala Val Tyr Ala Ser
```

-continued

```
               465                 470                 475                 480
        Gly Glu Leu Gln Glu Trp Ala Glu Pro Lys Glu Glu Glu Trp Ser
                        485                 490                 495

Asn Lys Glu Leu Val Asn Lys Thr Gly Ile Asn Gly Thr Gly Tyr Gly
                        500                 505                 510

Ala Ala Glu Thr Thr Phe Thr Gln Leu Pro Ala Gly Val Asp Ser Ser
                        515                 520                 525

Tyr Gln Ala Gln Ala Ala Pro Ala Pro Gly Thr Asn Pro Phe Ala Ser
                        530                 535                 540

Ala Trp Asp Glu His Gly Ser Ser Gly Val Val Glu Asn Pro His Tyr
        545                 550                 555                 560

Gln Gln Trp

<210> SEQ ID NO 7
<211> LENGTH: 495
<212> TYPE: PRT
<213> ORGANISM: Homo sapiens

<400> SEQUENCE: 7

Met Arg Ser Pro Val Arg Asp Leu Ala Arg Asn Asp Gly Glu Glu Ser
1               5                   10                  15

Thr Asp Arg Thr Pro Leu Leu Pro Gly Ala Pro Arg Ala Glu Ala Ala
                20                  25                  30

Pro Val Cys Cys Ser Ala Arg Tyr Asn Leu Ala Ile Leu Ala Phe Phe
            35                  40                  45

Gly Phe Phe Ile Val Tyr Ala Leu Arg Val Asn Leu Ser Val Ala Leu
        50                  55                  60

Val Asp Met Val Asp Ser Asn Thr Thr Leu Glu Asp Asn Arg Thr Ser
65                  70                  75                  80

Lys Ala Cys Pro Glu His Ser Ala Pro Ile Lys Val His His Asn Gln
                85                  90                  95

Thr Gly Lys Lys Tyr Gln Trp Asp Ala Glu Thr Gln Gly Trp Ile Leu
                100                 105                 110

Gly Ser Phe Phe Tyr Gly Tyr Ile Ile Thr Gln Ile Pro Gly Gly Tyr
            115                 120                 125

Val Ala Ser Lys Ile Gly Gly Lys Met Leu Leu Gly Phe Gly Ile Leu
        130                 135                 140

Gly Thr Ala Val Leu Thr Leu Phe Thr Pro Ile Ala Ala Asp Leu Gly
145                 150                 155                 160

Val Gly Pro Leu Ile Val Leu Arg Ala Leu Glu Gly Leu Gly Glu Gly
                165                 170                 175

Val Thr Phe Pro Ala Met His Ala Met Trp Ser Ser Trp Ala Pro Pro
            180                 185                 190

Leu Glu Arg Ser Lys Leu Leu Ser Ile Ser Tyr Ala Gly Ala Gln Leu
        195                 200                 205

Gly Thr Val Ile Ser Leu Pro Leu Ser Gly Ile Ile Cys Tyr Tyr Met
        210                 215                 220

Asn Trp Thr Tyr Val Phe Tyr Phe Phe Gly Thr Ile Gly Ile Phe Trp
225                 230                 235                 240

Phe Leu Leu Trp Ile Trp Leu Val Ser Asp Thr Pro Gln Lys His Lys
                245                 250                 255

Arg Ile Ser His Tyr Glu Lys Glu Tyr Ile Leu Ser Ser Leu Arg Asn
            260                 265                 270

Gln Leu Ser Ser Gln Lys Ser Val Pro Trp Val Pro Ile Leu Lys Ser
```

-continued

```
            275                 280                 285
Leu Pro Leu Trp Ala Ile Val Ala His Phe Ser Tyr Asn Trp Thr
    290                 295                 300
Phe Tyr Thr Leu Leu Thr Leu Leu Pro Thr Tyr Met Lys Glu Ile Leu
305                 310                 315                 320
Arg Phe Asn Val Gln Glu Asn Gly Phe Leu Ser Ser Leu Pro Tyr Leu
                325                 330                 335
Gly Ser Trp Leu Cys Met Ile Leu Ser Gly Gln Ala Ala Asp Asn Leu
                340                 345                 350
Arg Ala Lys Trp Asn Phe Ser Thr Leu Cys Val Arg Arg Ile Phe Ser
                355                 360                 365
Leu Ile Gly Met Ile Gly Pro Ala Val Phe Leu Val Ala Ala Gly Phe
    370                 375                 380
Ile Gly Cys Asp Tyr Ser Leu Ala Val Ala Phe Leu Thr Ile Ser Thr
385                 390                 395                 400
Thr Leu Gly Gly Phe Cys Ser Ser Gly Phe Ser Ile Asn His Leu Asp
                405                 410                 415
Ile Ala Pro Ser Tyr Ala Gly Ile Leu Leu Gly Ile Thr Asn Thr Phe
                420                 425                 430
Ala Thr Ile Pro Gly Met Val Gly Pro Val Ile Ala Lys Ser Leu Thr
                435                 440                 445
Pro Asp Asn Thr Val Gly Glu Trp Gln Thr Val Phe Tyr Ile Ala Ala
    450                 455                 460
Ala Ile Asn Val Phe Gly Ala Ile Phe Phe Thr Leu Phe Ala Lys Gly
465                 470                 475                 480
Glu Val Gln Asn Trp Ala Leu Asn Asp His His Gly His Arg His
                485                 490                 495

<210> SEQ ID NO 8
<211> LENGTH: 465
<212> TYPE: PRT
<213> ORGANISM: Rattus norvegicus

<400> SEQUENCE: 8

Met Glu Asn Arg Cys Leu Pro Lys Lys Val Pro Gly Phe Cys Ser Phe
1               5                   10                  15
Arg Tyr Gly Leu Ala Ile Leu Leu His Phe Cys Asn Ile Val Ile Met
            20                  25                  30
Ala Gln Arg Val Cys Leu Asn Leu Thr Met Val Ala Met Val Asn Lys
        35                  40                  45
Thr Glu Pro Pro His Leu Ser Asn Lys Ser Val Ala Glu Met Leu Asp
    50                  55                  60
Asn Val Lys Asn Pro Val His Ser Trp Ser Leu Asp Ile Gln Gly Leu
65                  70                  75                  80
Val Leu Ser Ser Val Phe Leu Gly Met Val Ile Gln Val Pro Val
                85                  90                  95
Gly Tyr Leu Ser Gly Ala Tyr Pro Met Glu Lys Ile Ile Gly Ser Ser
            100                 105                 110
Leu Phe Leu Ser Ser Val Leu Ser Leu Leu Ile Pro Ala Ala Gln
            115                 120                 125
Val Gly Ala Ala Leu Val Ile Val Cys Arg Val Leu Gln Gly Ile Ala
        130                 135                 140
Gln Gly Ala Val Ser Thr Gly Gln His Gly Ile Trp Val Lys Trp Ala
145                 150                 155                 160
```

```
Pro Pro Leu Glu Arg Gly Arg Leu Thr Ser Met Thr Leu Ser Gly Phe
            165                 170                 175
Val Met Gly Pro Phe Ile Ala Leu Leu Val Ser Gly Phe Ile Cys Asp
            180                 185                 190
Leu Leu Gly Trp Pro Met Val Phe Tyr Ile Phe Gly Ile Val Gly Cys
            195                 200                 205
Val Leu Ser Leu Phe Trp Phe Ile Leu Leu Phe Asp Asp Pro Asn Asn
210                 215                 220
His Pro Tyr Met Ser Ser Ser Glu Lys Asp Tyr Ile Thr Ser Ser Leu
225                 230                 235                 240
Met Gln Gln Val His Ser Gly Arg Gln Ser Leu Pro Ile Lys Ala Met
            245                 250                 255
Leu Lys Ser Leu Pro Leu Trp Ala Ile Ile Leu Asn Ser Phe Ala Phe
            260                 265                 270
Ile Trp Ser Asn Asn Leu Leu Val Thr Tyr Thr Pro Thr Phe Ile Ser
            275                 280                 285
Thr Thr Leu His Val Asn Val Arg Glu Asn Gly Leu Leu Ser Ser Leu
            290                 295                 300
Pro Tyr Leu Leu Ala Tyr Ile Cys Gly Ile Val Ala Gly Gln Met Ser
305                 310                 315                 320
Asp Phe Leu Leu Ser Arg Lys Ile Phe Ser Val Val Ala Val Arg Lys
            325                 330                 335
Leu Phe Thr Thr Leu Gly Ile Phe Cys Pro Val Ile Phe Val Val Cys
            340                 345                 350
Leu Leu Tyr Leu Ser Tyr Asn Phe Tyr Ser Thr Val Ile Phe Leu Thr
            355                 360                 365
Leu Ala Asn Ser Thr Leu Ser Phe Ser Phe Cys Gly Gln Leu Ile Asn
            370                 375                 380
Ala Leu Asp Ile Ala Pro Arg Tyr Tyr Gly Phe Leu Lys Ala Val Thr
385                 390                 395                 400
Ala Leu Ile Gly Ile Phe Gly Gly Leu Ile Ser Ser Thr Leu Ala Gly
            405                 410                 415
Leu Ile Leu Asn Gln Asp Pro Glu Tyr Ala Trp His Lys Asn Phe Phe
            420                 425                 430
Leu Met Ala Gly Ile Asn Val Thr Cys Leu Ala Phe Tyr Leu Leu Phe
            435                 440                 445
Ala Lys Gly Asp Ile Gln Asp Trp Ala Lys Glu Thr Lys Thr Thr Arg
    450                 455                 460
Leu
465

<210> SEQ ID NO 9
<211> LENGTH: 14
<212> TYPE: RNA
<213> ORGANISM: Artificial Sequence
<220> FEATURE:
<223> OTHER INFORMATION: hairpin ribozyme
<220> FEATURE:
<221> NAME/KEY: misc_feature
<222> LOCATION: (4)..(4)
<223> OTHER INFORMATION: b is g, c, or u
<220> FEATURE:
<221> NAME/KEY: misc_feature
<222> LOCATION: (9)..(14)
<223> OTHER INFORMATION: b is g, c, or u
<220> FEATURE:
<221> NAME/KEY: misc_feature
<222> LOCATION: (1)..(3)
<223> OTHER INFORMATION: n is a, g, c, or u
```

-continued

```
<220> FEATURE:
<221> NAME/KEY: misc_feature
<222> LOCATION: (5)..(5)
<223> OTHER INFORMATION: n is a, g, c, or u

<400> SEQUENCE: 9
nnnbngucnn nnnn                                                            14

<210> SEQ ID NO 10
<211> LENGTH: 32
<212> TYPE: DNA
<213> ORGANISM: Artificial Sequence
<220> FEATURE:
<223> OTHER INFORMATION: PCR primer

<400> SEQUENCE: 10
gggaattcat tcatgaagat gaactggatg aa                                        32

<210> SEQ ID NO 11
<211> LENGTH: 32
<212> TYPE: DNA
<213> ORGANISM: Artificial Sequence
<220> FEATURE:
<223> OTHER INFORMATION: PCR primer

<400> SEQUENCE: 11
ggctcgagct agcttcgtta tgaataatca tc                                        32
```